US008216572B2

(12) United States Patent
Goldenberg et al.

(10) Patent No.: US 8,216,572 B2
(45) Date of Patent: *Jul. 10, 2012

(54) ANTIBODY THERAPY

(75) Inventors: David M. Goldenberg, Mendham, NJ (US); Hans J. Hansen, Picayune, MS (US)

(73) Assignee: Immunomedics, Inc., Morris Plains, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/245,330

(22) Filed: Sep. 26, 2011

(65) Prior Publication Data

US 2012/0039797 A1 Feb. 16, 2012

Related U.S. Application Data

(60) Division of application No. 13/030,204, filed on Feb. 18, 2011, now Pat. No. 8,062,636, which is a division of application No. 12/639,298, filed on Dec. 16, 2009, now Pat. No. 7,919,090, which is a division of application No. 11/932,530, filed on Oct. 31, 2007, now Pat. No. 7,662,378, which is a continuation of application No. 10/680,734, filed on Oct. 8, 2003, now Pat. No. 7,803,372, which is a continuation-in-part of application No. PCT/US02/32307, filed on Oct. 11, 2002.

(60) Provisional application No. 60/467,161, filed on May 2, 2003, provisional application No. 60/416,531, filed on Oct. 8, 2002.

(51) Int. Cl.
*A61K 39/395* (2006.01)

(52) U.S. Cl. .................................... 424/130.1

(58) Field of Classification Search .................. None
See application file for complete search history.

(56) References Cited

U.S. PATENT DOCUMENTS

| | | | |
|---|---|---|---|
| 4,818,709 A | 4/1989 | Primus et al. |
| 4,970,071 A | 11/1990 | McMichael |
| 5,081,235 A | 1/1992 | Shivery et al. |
| 5,530,101 A | 6/1996 | Queen et al. |
| 5,843,708 A | 12/1998 | Hardman et al. |
| 5,874,540 A | 2/1999 | Hansen et al. |
| 5,877,293 A | 3/1999 | Adair et al. |
| 6,077,499 A | 6/2000 | Griffiths et al. |
| 7,011,812 B1 | 3/2006 | Griffiths et al. |
| 2004/0001825 A1 | 1/2004 | Govindan et al. |
| 2004/0043030 A1 | 3/2004 | Griffiths et al. |
| 2005/0222392 A1 | 10/2005 | Carter et al. |
| 2006/0160766 A1 | 7/2006 | Cheung |

FOREIGN PATENT DOCUMENTS

| | | |
|---|---|---|
| EP | 0239400 | 9/1987 |
| EP | 0323805 | 7/1989 |
| EP | 0323806 | 7/1989 |
| WO | 91/01990 | 2/1991 |
| WO | 92/01059 | 1/1992 |
| WO | 92/11018 | 7/1992 |
| WO | 95/15769 | 6/1995 |
| WO | 96/01126 | 1/1996 |
| WO | 96/08506 | 3/1996 |
| WO | 96/11013 | 4/1996 |

OTHER PUBLICATIONS

Stein et al Cancer 94:51-61 (2002).*
Blumenthal et al Cancer Res. 54:142-51 (1994).*
Beckman et al., "Antibody Constructs in Cancer Therapy", Cancer 109:170-179 (2007).
Begent et al., "Clinical Evidence of Efficient Tumor Targeting Based on Single-Chain Fv Antibody Selected from a Combinatorial Library", Nat. Med. 2:979-984 (1996).
Berenbaum, M., "Synergy, additivism and antagonism in immunosuppresion", Clin. exp. Immunol. (1997) 28, 1-18.
Berenbaum, M., "What is Synergy?", Pharmacol. Rev. 41:93-141 (1989).
Blumenthal et al., "Comparison of Equitoxic Radioimmunotherapy and Chemotherapy in the Treatment of Human Colonic Cancer Xenografts", Cancer Res., 54:142-151 (1994).
Blumenthal et al., "Targeted therapy of athymic mice bearing GW-39 human colonic cancer micrometastases with 131I-labeled monoclonal antibodies", Cancer Res. 52(21):6036-44 (1992).
Blumenthal et al., "Carcinoembryonic antigen antibody inhibits lung metastasis and augments chemotherapy in a human colonic carcinoma xenograft", Cancer Immunol. Immunother. 54(4):315-27 (2005).
Casset et al., "A peptide mimetic of an anti-CD74 monoclonal antibody by rational design", Biochem. Biophys. Research Comm. 307:198-205 (2003).
Dennis, C. "Off by a Whisker", Nature 442:739-741 (2006).
Dillman, R., "Antibodies as cytotoxic therapy", J Clin Oncol. Jul. 1994;12(7):1497-515.
Groninger et al., "Vincristine Induced Apoptosis in Acute Lymphoblastic Leukaemia Cells: A Mitochondrial Controlled Pathway Regulated by Reactive Oxygen Species?" Abstract, Int. J. Oncol. 21:1339-45 (2002).
Hansen et al., "Characterization of Second-Generation Monoclonal Antibodies Against Carcinoembryonic Antigen", Cancer 71:3478-3485 (1993).
Juweid et al., "Radioimmunotherapy of medullary thyroid cancer with iodine-131-labeled anti-CEA antibodies", J. Nucl. Med. 37(6):905-11 (1996).
Juweid et al., "Radioimmunotherapy of patients with small-volume tumors using iodine-131-labeled anti-CEA monoclonal antibody NP-4 F(ab')2", J Nucl Med. 37(9):1504-10 (1996).
Juweid et al., "Phase I/II Trial of 131I-MN-14 F(ab)2 Anti-Carcinoembryonic Antigen Monoclonal Antibody in the Treatment of Patients with Metastatic Medullary Thyroid Carcinoma", Cancer 85(8):1828-1842 (1999).
Losman et al., "Mimicry of a Carcinoembryonic Antigen Epitope by a Rat Monoclonal Anti-Idiotype Antibody", Int. J. Cancer 56:580-584 (1994).
MacCallum et al., "Antibody-antigen Interactions: Contact Analysis and Binding Site Topography", J. Mol. Biol. 262:732-745 (1996).

(Continued)

Primary Examiner — Sheela J Huff
(74) Attorney, Agent, or Firm — Richard A. Nakashima

(57) ABSTRACT

The present invention provides a composition comprising naked humanized, chimeric, and human anti-CEA antibodies and a therapeutic agent, which is useful for treatment of CEA expressing cancers and other diseases, and methods of use in treatment using this composition.

19 Claims, 31 Drawing Sheets

OTHER PUBLICATIONS

Mani et al., "Novel Combinations with Oxaliplatin" Abstract, Oncol. 14:52-8 (2000).

Mayer et al., "Radioimmunoguided Surgery in Colorectal Cancer Using a Genetically Engineered Anti-CEA Single-Chain Fv Antibody", Clin. Can. Res. 6:1711-1719 (2000).

Muyldermans et al., "Sequence and structure of VH Domain from naturally occurring camel heavy chain immunoglobulins lacking light chains", Protein Eng. 7(9):1129-35 (1994).

Nap et al., "Specificity and Affinity of Monoclonal Antibodies against Carcinoembryonic Antigen", Can. Res. 52:2329-2339 (1992).

Neumaier et al., "Cloning of the Genes for T84.66, an Antibody that has a High Specificity and Affinity for Carcinoembryonic Antigen, and Expression of Chimeric Human/Mouse T84.66 Genes in Myeloma and Chinese Hamster Ovary Cells", Can. Res. 50:2128-2134 (1990).

Nowak et al., "Induction of Tumor Cell Apoptosis in Vivo Increases Tumor Antigen Cross-Presentation, Cross-Priming Rather than Cross-Tolerizing Host Tumor-Specific CD8 T Cells", J. Immunol. 170:4905-13 (2003).

Pascalis et al., "Grafting of "Abbreviated" Complementarity-Determining Regions Containing Specificity-Determining Residues Essential for Ligand Contact to Engineer a Less Immunogenetic Humanized Monoclonal Antibody", J. Immunol. 169:3076-3084 (2002).

Paul, W. (ed.), Fundamental Immunology, Raven Press, NY, 1993, p. 242.

Perez et al., "A Multivalent Recombinant Antibody Fragment Specific for Carcinoembryonic Antigen", Biotechnol. Appl. Biochem. 43:39-48 (2006).

Primus et al., "Immunological heterogeneity of carcinoembryonic antigen: antigenic determinants on carcinoembryonic antigen distinguished by monoclonal antibodies", Cancer Res. 43(2):686-692 (1983).

Queen et al., "A humanized antibody that binds to the interleukin 2 receptor", Proc. Natl. Acad. Sci. USA 86:10029-10033 (1989).

Ray et al., "Apoptosis Induction of Prostate Cancer Cells and Xenografts by Combined Treatment with Apo2 Ligand/Tumor Necrosis Factor-related Apoptosis-inducing Ligand and CPT-11", Can. Res. 63:4713-23 (2003).

Riechmann et al., "Reshaping human antibodies for therapy", Nature 332(6162):323-7 (1988).

Rigas et al., "Selective Induction of Colon Cancer Cell Apoptosis by 5-Flourouracil in Humans", Abstract, Cancer Invest. 20:657-65 (2002).

Senba et al., "Tumor Growth Suppression by a Mouse/Human Chimeric Anti-CEA Antibody and Lymphokine-Activated Killer Cells in Vitro and in SCID Mouse Xenograft Model", Anticancer Research 18:17-24 (1998).

Sharkey et al., "Murine Monoclonal Antibodies against Carcinoembryonic Antigen: Immunological, Pharmacokinetic, and Targeting Properties in Humans", Cancer Res. 50:2823-2831 (1990).

Sharkey et al., "Clinical evaluation of tumor targeting with a high-affinity, anticarcinoembryonic-antigen-specific, murine monoclonal antibody, MN-14", Cancer 71(6):2082-96 (1993).

Sharkey et al., "Comparison of Tumor Targeting in Nude Mice by Murine Monoclonal Antibodies Directed against Different Human Colorectal Cancer Antigens", Cancer Res. (Suppl.) 50:828-834 (1990).

Sharkey et al., "Evaluation of a complementarity-determining region-grafted (humanized) anti-carcinoembryonic antigen monoclonal antibody in preclinical and clinical studies", Cancer Res. 55(23 Suppl):5935s-5945s (1995).

Shibuya et al., "Induction of Apoptosis and/or Necrosis Following Exposure to Antitumour Agents in a Melanoma Cell Line, Probably Through Modulation of Bcl-2 Family Proteins", Abstract, Melanoma Res. 13:457-64 (2003).

Simoes-Wust et al., "Bcl-2/bcl-xL Bispecific Antisense Treatment Sensitizes Breast Carcinoma Cells to Doxorubicin, Paclitaxel and Cyclophosphamide", Abstract, Breast Cancer Res. 76:157-66 (2002).

Stein et al., "Combining Radioimmunotherapy and Chemotherapy for Treatment of Medullary Thyroid Carcinoma", Cancer 94:51-61 (2002).

Stein et al., "A humanized monoclonal antibody to carcinoembryonic antigen, labetuzumab, inhibits tumor growth and sensitizes human medullary thyroid cancer xenografts to dacarbazine chemotherapy", Mol. Cancer Ther. 3 (12):1559-64 (2004).

Tallarida, R., "Drug Synergism and Dose-Effect Data Analysis", Ed. Chapman & Hall (2000), pp. 1-13; 57-71.

Tsang et al., "Reactive Oxygen Species Mediate Doxorubicin Induced p53-Independent Apoptosis", Life Sci. 73:2047-58 (2003).

Ueno et al., "SN-38 Induces Cell Cycle Arrest and Apoptosis in Human Testicular Cancer", Eur. Urol. 42:390-7 (2002).

Vajdos et al., "Comprehensive Functional Maps of the Antigen-binding Site of an Anti-ErbB2 Antibody Obtained with Shotgun Scanning Mutagenesis", J. Mol. Biol. 320:415-428 (2002).

Verhoeyen et al., "Reshaping human antibodies: grafting an antilysozyme activity", Science 239(4847):1534-6 (1987).

Voskoglou-Nomikos et al., "Clinical Predictive Value of the in Vitro Cell Line, Human Xenograft, and Mouse Allograft Preclinical Cancer Models", Clin. Can. Res. 9:4227-4239 (2003).

Wong et al., "A Phase I Radioimmunotherapy Trial Evaluating 90Yttrium-labeled Anti-Carcinoembryonic Antigen (CEA) Chimeric T84.66 in Patients with Metastatic CEA-producing Malignancies", Clin. Can. Res. 6:3855-3863 (2000).

Wong et al., "A Phase I Trial of 90Y-Anti-Carcinoembryonic Antigen Chimeric T84.66 Radioimmunotherapy with 5-Fluorouracil in Patients with Metastatic Colorectal Cancer", Clin. Can. Res. 9:5842-5852 (2003).

Wong et al., "Pilot Trial Evaluating an 123I-Labeled 80-Kilodalton Engineered Anticarcinoembryonic Antigen Antibody Fragment (cT84.66 Minibody) in Patients with Colorectal Cancer", Clin. Can. Res. 10:5014-5021 (2004).

Wu et al., "Humanization of a Murine Monoclonal Antibody by Simultaneous Optimization of Framework and CDR Residues", J. Mol. Biol. 294:151-162 (1999).

* cited by examiner

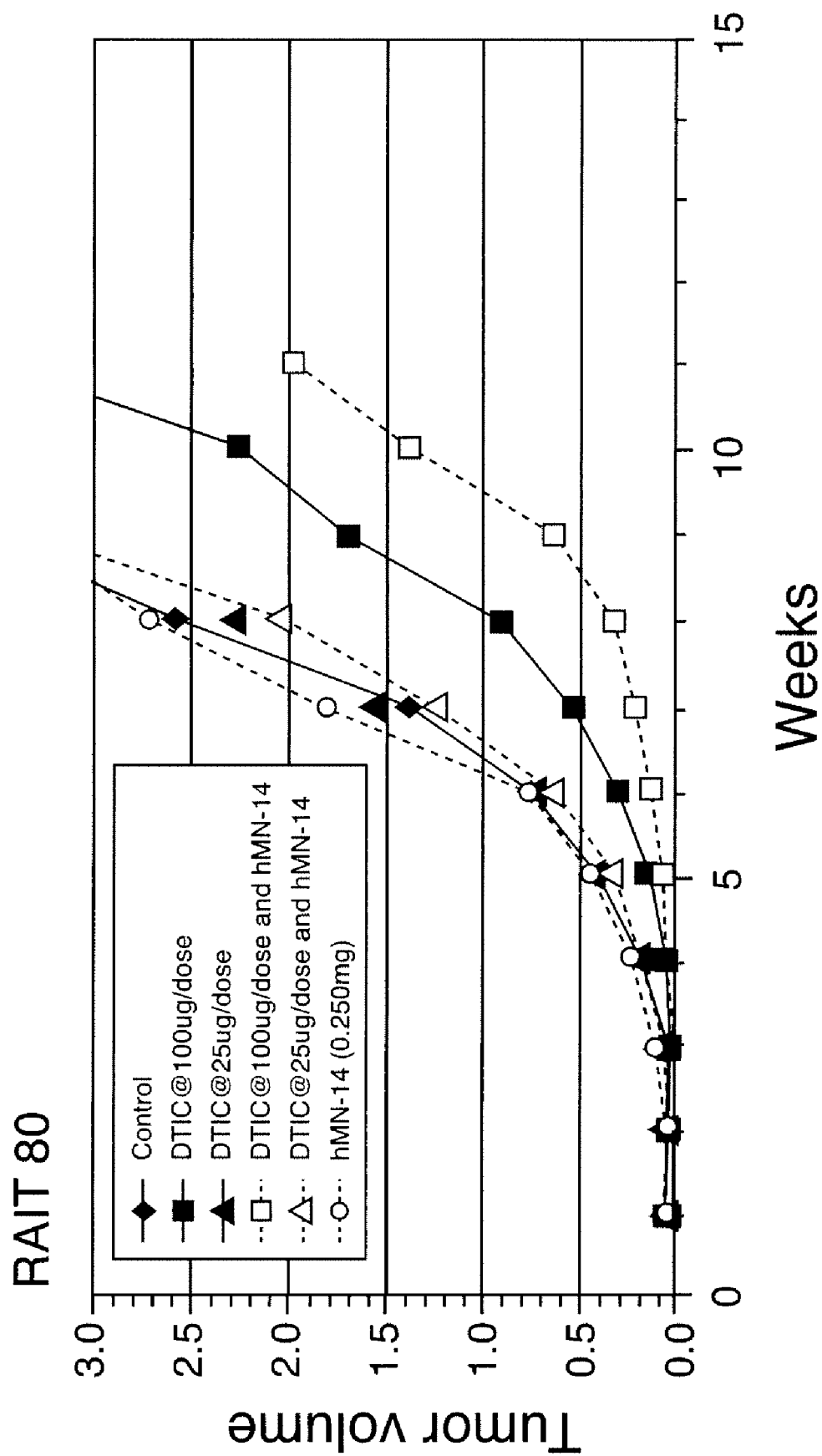

Figure 8

Effect of hMN-14 dose

Legend:
- ◆ untreated
- ■ 0.125 mg
- — 0.250 mg
- ● 0.50 mg
- ☐ 1.0 mg
- △ 2.0 mg X-axis: Days (0–100)
Y-axis: Mean Tumor Volume (cm$^3$) (0–5)

```
                    H A    XAHTHM          P    HHEAS  M                BXBNMDDB  E
                    I L    HVPANN          L    AACPC  N                IHALBPPI  C
                    N U    OAHQFL          E    EERYR  L                NOMAONNN  O
                    3 1    111111          1    13211  1                12141211  K

GAGGTGAAGCTTCTCGAGTCTGGAGGTGGCCTGGTGCAGTCTGGAGGATCCCTGAAACTC
----+----|----+----|----+----|----+----|----+----|----+----|    +60
 e  v  k  l  l  e  s  g  g  g  l  v  q  s  g  g  s  l  k  l

F    MD     THBTMH     F                        ANAFH     NEB
                  N    SD     FNBANN     O                        VLSOP     LCS
                  U    TE     IFVQLF     K                        AAUKA     ARA
                  H    21     111113     1                        24112     42J

CTCCACTTCGAAGAGCTCGGAGTCCTAAGCTAAAATGATGTATAACCTACTCAACCCAGGCCGTCCGA
----+----|----+----|----+----|----+----|----+----|----+----|    +120
 s  c  a  a  s  g  f  d  f  t  y  w  m  s  w  v  r  q  a

TCCTGTGCAGCCTCAGGATTCGATTTTACTACATATTGGATGAGTTGGGTCCGGGCAGGCT
----+----|----+----|----+----|----+----|----+----|----+----|

SASB     SHHRM      F                                    R       M
EPCS     TAAMA      O                                    S       S
CYRA     UEEAE      K                                    A       E
111J     11311      1                                    1       1

CCAGGGAAAGGCCTAGAATGGATTGGAGAAATTCATCCAGATAGCAGTACGATTAACTAT
----+----|----+----|----+----|----+----|----+----|----+----|    +180
 p  g  k  g  l  e  w  i  g  e  i  h  p  d  s  s  t  i  n  y

GGTCCCTTTCCGGATCTTACCTAACCTCTTTAAGTAGGTCTATCGTCATGCTAATTGATA
----+----|----+----|----+----|----+----|----+----|----+----|
```

```
                      FR1                      24  27 30        CDR1    FR2                      48
         EVKLLESGGGLVQSGGSLKLSCAASGFDFT         TYWMS   WVRQAPGKGLEWIG
Murine   EVKLLESGGGLVQSGGSLKLSCAASGFDFT         TYWMS   WVRQAPGKGLEWIG
NEWMVh   -Q-Q---------RPSQT-S-T-TV--ST-S        -----   -----P--R-----
NMHuVh   -Q-Q---------RPSQT-S-T-T------         -----   -----P--R-----
NMHUVhTLY -Q-Q---------RPSQT-S-T-T------        -----   -----P--R-----
NMHUVhkRSE -Q-Q---------RPSQT-S-T-T------       -----   -----P--R-----
NMHUVhkFIVS -Q-Q---------RPSQT-S-T-T------      -----   -----P--R-----
KOLVh    ---Q-V-------V--P-R---SS---I-S         -----   --------------
KLHuVh   ---Q-V-------V--P-R---SS------         -----   --------------
KLHuVhAIG ---Q-V-------V--P-R---S-------         -----   ------------VA
KLHuVhAIGA ---Q-V-------V--P-R---S-------        -----   ------------VA
KLHuVhAIGAY ---Q-V-------V--P-R---S-------       -----   --------------
```

Figure 14B

|  | CDR2 | | FR3 | |
|---|---|---|---|---|
|  |  | 66      71   74  77 79    82                94 |
| Murine | EIHPDSSTINYAPSLKD | KFIVSRDNAKNTLYLQMSKVRSEDTALYYCAS |
| NEWMVh | ----------------- | RVTMLV-TS---QFS-RL-S-TAA---V----R |
| NMHuVh | ----------------- | RVTML--TS---QFS-RL-S-TAA---V----- |
| NMHUVhTLY | ----------------- | RVTML--TS-----RL-S-TAA---V----- |
| NMHUVhKRSE | ----------------- | RVTML--TS---QFS-RL-------V----- |
| NMHUVhKFIVS | ----------------- | -------TS---QFS-RL-S-TAA---V----- |
| KOLVh | ----------------- | R-TI----S----F----DSL-P----GV-F--R |
| KLHuVh | ----------------- | R-TI----S----F----DSL-P----GV-F--- |
| KLHuVhAIG | ----------------- | R-TI----S----F----DSL-P----GV-F--- |
| KLHuVhAIGA | ----------------- | R-TI---------F----DSL-P----GV-F--- |
| KLHuVhAIGAY | ----------------- | R-TI--------------DSL-P----GV-F--- |

Lung Model: 5% GW-39 suspension

Increased expression of CEA antigen on tumor cells correlates with improved efficacy of anti-CEA (hMN14) antibody in animal models

Figure 22A

```
             1                    10                   20                   30                40
REI  Vκ      DIQLTQSPSSLSASVGDRVTITC QASQDIIKYLNWYQQKP
MN14 Vκ      E..........HKMM.T....... S....K....VGTSVA.....R.
hMN14 Vκ     ....................... ....K....VGTSVA.......

50                   60                   70                80
REI  Vκ      GKAPKLLIY EASNLQA GVPSRFSGSGSGTDFTFTISSLQP
MN14 Vκ      ........ QS..... WT.TRHT .T.V....L..TNV.S
hMN14 Vκ     ........ ...... WT.TRHT .........TNV.S 90                   100                  107
REI  Vκ      EDIATYYC QQYQSLPYT FGQGTKVEIK
MN14 Vκ      ........ .L.D.F... YRS...G...L....
hMN14 Vκ     ........ ......... YRS.........
```

Figure 22B

```
              1                    10                  20                  30              40
KOL  V_H      EVQLVESGGGVVQPGRSLRLSCSSSGFIFSSYAMYWVRQA
MN14 V_H      ..K.L......L..S.G...K...AA...D.TT.W.S...
hMN14 V_H     ................A....D.TT.W.S...

50 52ABC            60                 70
              PGKGLEWVAIWDDGSDQHYADSVKGRFTISRDNSKNTLF
KOL  V_H
MN14 V_H      ........IGE.HP.S.TIN.P.L.DK.IV....A....Y
hMN14 V_H     ........IGE.HP.S.TIN.P.L.D........A....

80 82ABC             90                  100 ABCDEFGHI
KOL  V_H      LQMDSLRPEDTGVYFCARDGGHGFCSSASCFGPDY
MN14 V_H      ...SKV.S....AL.Y...SLYFGPWF-----A.
hMN14 V_H     ...................SLYFGPWF-----A.

103         110   113
KOL  V_H      WGQGTPVTVSS
MN14 V_H      ...........A
hMN14 V_H     ............
```

Figure 23A

```
         PvuII
GACATCCAGCTGACCCAGAGCCCAAGCAGCCCTGAGCGTGGGTGACAGAGTGACCATCACCTGTAAGGCCAGTCAGGATGTGGGT    90
1                          10                        20                        30
 D  I  Q  L  T  Q  S  P  S  S  L  S  A  S  V  G  D  R  V  T  I  T  C  K  A  S  Q  D  V  G
                                                                         CDR1

ACTTCTGTAGCCTGGTACCAGCAGAAGCCAGGTAAGGCTCCAAAGCTGATCTACTGGACATCCACCCGGCACACTGGTGTGCCAAGC   180
                     40                        50                        60
 T  S  V  A  W  Y  Q  Q  K  P  G  K  A  P  K  L  I  Y  W  T  S  T  R  H  T  G  V  P  S
         CDR2                                      CDR2

AGATTCAGCGGTAGCGGTAGCGGTACCGACTTCACCTTCACCATCAGCAGCCTCCAGCCAGAGGACATCGCCACCTACTACTGCCAGCAA   270
                         70                        80                        90
 R  F  S  G  S  G  S  G  T  D  F  T  F  T  I  S  S  L  Q  P  E  D  I  A  T  Y  Y  C  Q  Q

TATAGCCTCTATCGGTCGTTCGGCCAAGGGACCAAGGTGGAAATCAAA                                            338
        94 96              100                 107
 Y  S  L  Y  R  S  F  G  Q  G  T  K  V  E  I  K
    CDR3
```

Figure 23B

```
GAGGTCCAACTGGTGGAGAGCGGTGGAGGTGTTGTGCAACTGGCCGGTCCCTGCGCCTGCTCCGCATCTGGCTTCGATTTCACCACATAT
TGGATGAGTTGGGTGAGACAGGCCACCTGGAAAAGGTCTTGAGTGGATTGGAGAAATTCATCCAGATAGCAGTACGATTAACTATGCGCCGTCTCTA
AAGGATAGATTTACAAATATCGCGAGACAACGCCAAGAACACATTGTTCCTGCAAATGGACAGCCTGAGACCCGAAGACACCGGGGTCTATTTTTGT
                                                                      BstEII
GCAAGCCTTTACTTCGGCTTCCCCCTGGTTTGCTTATTGGGGCCAAGGGACCCCGGTCACCGTCTCCTCA

E V Q L V E S G G G V V Q L P G R S L R L S C S A S G F D F T
T Y W M S W V R Q A P G K G L E W I G  E I H P D S S T I N Y
—————                                  ————————————————————
CDR1                                    CDR2
A P S L K D R F T I S R D N A K N T L F L Q M D S L R P E D
—————
T G V Y F C A S L Y F G F P W F A Y W G Q G T P V T V S S
              ———————————————————
              CDR3
```

ANTIBODY THERAPY

RELATED APPLICATIONS

This application is a divisional of U.S. application Ser. No. 13/030,204, filed Feb. 18, 2011, which was a divisional of U.S. application Ser. No. 12/639,298 (now U.S. Pat. No. 7,919,090), filed Dec. 16, 2009, which was a divisional U.S. application Ser. No. 11/932,530 (now U.S. Pat. No. 7,662,378), filed Oct. 31, 2007, which was a continuation of U.S. application Ser. No. 10/680,734 (now U.S. Pat. No. 7,803,372), filed Oct. 8, 2003, which claimed the benefit under 35 U.S.C. 119(e) of U.S. Provisional Application No. 60/467,161, filed May 2, 2003. This application also claims priority to International Application No. PCT/US02/32307, filed Oct. 11, 2002, which in turn claimed the benefit under 35 U.S.C. 119(e) of U.S. Provisional Application No. 60/416,531, filed Oct. 8, 2002.

BACKGROUND OF THE INVENTION

A. Field of the Invention

The invention relates to methods of treating cancers that express carcinoembryonic antigen ("CEA"), particularly medullary thyroid cancer (MTC), non-medullary thyroid cancers (non-MTC), colorectal cancers, hepatocellular carcinoma, gastric cancer, lung cancer, breast cancer and other cancers, in which CEA is expressed, by administering an immunological reagent comprising an antibody in combination with at least one other therapeutic agent, such as another antibody, a chemotherapeutic agent, a radioactive agent, an antisense oligonucleotide, an immunomodulator, an immunoconjugate or a combination thereof. The invention further relates to pharmaceutical compositions comprising the immunological reagent and at least one therapeutic agent in an unconjugated form. In particular, the invention relates to methods of treating cancers that express CEA by administering, prior to, with or after administering the therapeutic agent, a Class III anti-carcinoembryonic antigen ("anti-CEA") monoclonal antibody ("MAb"), particularly a MAb, that has the binding affinity characteristics and specificities of corresponding murine Class III anti-CEA MAb, and more particularly humanized, chimeric or human MAbs, that possess more of the antigenic and effector properties of a human antibody. Particularly useful MAbs in the method of treatment are humanized MAbs in which the complementarity-determining regions ("CDRs") of an anti-CEA murine MAb are grafted into the framework regions of a human antibody.

B. Background

CEA is an oncofetal antigen commonly expressed in a number of epithelial cancers, most commonly those arising in the colon but also in the breast, lung, pancreas, thyroid (medullary type) and ovary (Goldenberg et al., *J. Natl. Cancer Inst.* 57:11-22 (1976), Shively, et al., *Crit. Rev. Oncol. Hematol.* 2:355-399 (1985)). CEA was originally thought to be a tumor-specific antigen of colorectal cancer (Gold et al., *J. Exper. Med.,* 122:467 (1965)). However, it was later found to be present in a diverse number of carcinomas, benign tumors, and diseased tissues, as well as in normal human colon (Shively et al., *Crit. Rev. Oncol. Hematol.,* 2:355 (1985); von Kleist et al., *Proc. Natl. Acad. Sci. USA.,* 69:2492 (1972)). CEA has been shown to mediate cell-cell adhesion through homotypic and heterotypic interactions, which in turn have implicated a role for CEA in various aspects of tumorigenesis.

Medullary thyroid cancer (MTC) confined to the thyroid gland is potentially curable by total thyroidectomy and central lymph node dissection. However, disease recurs in approximately 50% of these patients. In addition, the prognosis of patients with unresectable disease or distant metastases is poor, less than 30% survive 10 years (Rossi et al., *Amer. J. Surgery,* 139:554 (1980); Samaan et al., *J. Clin. Endocrinol. Metab.,* 67:801 (1988); Schroder et al., *Cancer,* 61:806 (1988). These patients are left with few therapeutic choices (*Principles and Practice of Oncology*, DeVita, Hellman and Rosenberg (eds.), New York: JB Lippincott Co. 1333-1435 (1989); Cance et al., *Current Problems Surgery,* 22:1 (1985)). Chemotherapy has been of little value and radiation therapy may only be used to control local disease (Cance et al.; Tubiana et al., *Cancer,* 55:2062 (1985)). Thus, new therapeutic modalities are needed to control this disease.

A useful approach to cancer therapy and diagnosis involves the use of targeting antibodies to deliver therapeutic and diagnostic agents directly to the site of a malignancy. Over the past decade, a wide variety of tumor-specific antibodies and antibody fragments have been developed, as have methods to conjugate the antibodies to therapeutic agents, such as drugs, toxins, radionuclides, immunomodulators, such as cytokines or other agents, and to administer the conjugates to patients that target the tumor. However, patients treated with drugs or radionuclides complexed with murine monoclonal antibodies (which have been the most commonly used targeting antibodies for humans) develop circulating human anti-mouse antibodies (HAMAs) and sometimes a generalized immediate type-III hypersensitivity reaction to the antibody moiety of the conjugate. But these problems have been minimized by making these murine antibodies less immunogenic by a number of different methods, which include making humanized, chimeric or human antibodies, by chemically modifying the targeting antibody, such as by conjugating to polyethylene glycol to the targeting antibody (PEGylation), or by characterizing the situs of antigenicity in an antibody and then removing it; e.g., Fab', F(ab)$_2$ and other antibody fragments have been used in place of whole IgG. In addition, attempts have been made to reduce the adverse effects of HAMA by plasmaphoretically removing HAMA from blood. Immunosuppressive techniques also have been used to ameliorate the adverse effect of the foreign antibody sufficiently to permit multiple treatments with the targeting agent.

Regardless of these treatment advances, there still exists a need to provide more effective methods of treating CEA-expressing cancers. The present invention provides an effective therapy utilizing anti-CEA antibodies, such as a Class III anti-CEA MAb, the murine MN-14 MAb as defined in U.S. Pat. No. 5,874,540 and Hansen et al., Cancer, 71:3478 (1993), and a Class III anti-CEA MAb, the chimeric and humanized MN-14 MAbs as also defined in U.S. Pat. No. 5,874,540, and the NP-4 as defined in U.S. Pat. No. 4,818,709 by Primus et al., for example, all incorporated herein in their entirety by reference. Preferably, the Class III anti-CEA MAb is humanized, and used in combination with a therapeutic agent, particularly a chemotherapeutic agent, to yield an effective therapeutic treatment for CEA expressing cancers with minimal toxicity. Additionally, other anti-CEA antibodies, such Class II MAbs, for example, MN-6 (see Hansen et al., above, and NP-3 (se U.S. Pat. No. 4,818,709), and Class I MAbs, such MN-3 and MN-15 (see also Hansen et al., above) provide effective methods of treating CEA expressing cancers. Further, the separate administration of these two components provides enhanced results and the versatility and the flexibility to tailor individual treatment methods.

SUMMARY OF THE INVENTION

Contemplated in the present invention are compositions and methods of treating medullary and non-medullary thyroid carcinomas.

The first embodiment of the present invention is a composition comprising at least one anti-CEA monoclonal antibody (MAb) or fragment thereof, which is preferably a Class III anti-CEA MAb or fragment, and at least one therapeutic agent. Preferably, the antibody fragment is selected from the group consisting of F(ab')$_2$, Fab', Fab, Fv and scFv. Also preferred, the Class III anti-CEA MAb or fragment thereof is humanized, and wherein the humanized MAb retains substantially the Class III anti-CEA binding specificity of a murine Class III anti-CEA MAb. Also preferred, the Class III anti-CEA MAb or fragment thereof is a chimeric MAb, and wherein the chimeric MAb retains substantially the Class III anti-CEA binding specificity of murine Class III anti-CEA MAb. Still preferred, the Class III anti-CEA MAb or fragment thereof is a fully human MAb, and wherein said fully human MAb retains substantially the Class III anti-CEA binding specificity of murine Class III anti-CEA MAb. Other preferred anti-CEA Mabs for this purpose include Class II Mabs or fragments thereof, that are not CD66a-d cross-reactive which are discussed in greater detail herein. Another embodiment includes Class II anti-CEA Mabs or fragments thereof, that may react with CD66a, b and d but not CD66c or Class I Mabs or fragments thereof, that react with CD66a, b, or d as well as CD66c (by definition a Class I Mab binds with CD66c).

In one embodiment of the present invention, the Class III anti-CEA monoclonal antibody or fragment thereof is preferably a MN-14 antibody or fragment thereof. More preferably, the MN-14 monoclonal antibody or fragment thereof comprises the complementarity-determining regions (CDRs) of a murine MN-14 monoclonal antibody, wherein the CDRs of the light chain variable region of the MN-14 antibody comprises CDR1 comprising the amino acid sequence KASQDVGTSVA (SEQ ID NO: 20); CDR2 comprising the amino acid sequence WTSTRHT (SEQ ID NO: 21); and CDR3 comprising the amino acid sequence QQYSLYRS (SEQ ID NO: 22); and the CDRs of the heavy chain variable region of the Class III anti-CEA antibody comprises CDR1 comprising TYWMS (SEQ ID NO: 23); CDR2 comprising EIHPDSSTINYAPSLKD (SEQ ID NO: 24); and CDR3 comprising LYFGFPWFAY (SEQ ID NO: 25). Also preferred, the MN-14 monoclonal antibody reacts with CEA and is unreactive with normal cross-reactive antigen (NCA) and meconium antigen (MA). Most preferably, the MN-14 monoclonal antibody or fragment thereof is a humanized, chimerized or fully human MN-14 antibody or fragment thereof.

In a preferred embodiment, the framework regions (FRs) of the light and heavy chain variable regions of the humanized MN-14 antibody or fragment thereof comprise at least one amino acid substituted from the corresponding FRs of a murine MN-14 monoclonal antibody. Specifically, the humanized MN-14 antibody or fragment thereof preferably comprises at least one amino acid from the corresponding FR of the murine MN-14 antibody is selected from the group consisting of amino acid residue 24 (A), 28 (D), 30 (T), 48 (I), 49 (G), 74 (A) and 94 (S) of the murine heavy chain variable region (KLHuVhAIGA) of FIG. 14A-C. Likewise, the humanized MN-14 antibody or fragment thereof may also comprise at least one amino acid from said corresponding FR of the murine MN-14 light chain variable region. Still preferred, the humanized MN-14 antibody or fragment thereof comprises the light chain variable region as set forth in FIG. 13A, and the heavy chain variable region set forth in FIG. 14A-C designated as KLHuVhAIGA.

In the first embodiment of the present invention, the therapeutic agent is selected from the group consisting of a naked antibody, a cytotoxic agent, a drug, a radionuclide, an immunomodulator, a photoactive therapeutic agent, an immunoconjugate, a hormone, or a combination thereof, optionally formulated in a pharmaceutically acceptable vehicle. It is also contemplated herein that the therapeutic agent is not dacarbazine (DTIC).

The second embodiment of the present invention describes a method for treating medullary as well as non-medullary thyroid carcinoma comprising administering to a subject, either concurrently or sequentially, a therapeutically effective amount a Class III anti-CEA monoclonal antibody or fragment thereof and at least one therapeutic agent, and optionally formulated in a pharmaceutically acceptable vehicle. Preferably, the antibody fragment is selected from the group consisting of F(ab')$_2$, Fab', Fab, Fv and scFv. Also preferred, the Class III anti-CEA MAb or fragment thereof is humanized, wherein said humanized MAb retains substantially the Class III anti-CEA binding specificity of a murine Class III anti-CEA MAb. It is also contemplated that the Class III anti-CEA MAb or fragment thereof is a chimeric MAb, and wherein said chimeric MAb retains substantially the Class III anti-CEA binding specificity of murine Class III anti-CEA MAb.

In a preferred embodiment, the Class III anti-CEA monoclonal antibody or fragment thereof is a MN-14 antibody or fragment thereof. Preferably, the MN-14 monoclonal antibody or fragment thereof comprises the complementarity-determining regions (CDRs) of a murine MN-14 monoclonal antibody, wherein the CDRs of the light chain variable region of said MN-14 antibody comprises CDR1 comprising the amino acid sequence KASQDVGTSVA (SEQ ID NO: 20); CDR2 comprising the amino acid sequence WTSTRHT (SEQ ID NO: 21); and CDR3 comprising the amino acid sequence QQYSLYRS (SEQ ID NO: 22); and the CDRs of the heavy chain variable region of said Class III anti-CEA antibody comprises CDR1 comprising TYWMS (SEQ ID NO: 23); CDR2 comprising EIHPDSSTINYAPSLKD (SEQ ID NO: 24); and CDR3 comprising LYFGFPWFAY (SEQ ID NO: 25). Also preferred, the MN-14 monoclonal antibody is humanized, chimerized or fully human, and reacts with CEA and is unreactive with normal cross-reactive antigen (NCA) and meconium antigen. Also preferred, the MN-14 antibody or fragment thereof is administered in a dosage of 100 to 600 milligrams protein per dose per injection. Most preferably, the MN-14 antibody or fragment thereof is administered in a dosage of 300-400 milligrams protein per dose per injection.

In the methods of the instant invention, the framework regions (FRs) of the light and heavy chain variable regions of said humanized MN-14 antibody or fragment thereof preferably comprise at least one amino acid substituted from the corresponding FRs of a murine MN-14 monoclonal antibody. More preferred, the humanized MN-14 antibody or fragment thereof comprising at least one amino acid from said corresponding FR of said murine MN-14 antibody is selected from the group consisting of amino acid residue 24, 28, 30, 48, 49, 74 and 94 of the murine heavy chain variable region of FIG. 14A-C, as noted above. Also preferred, the humanized MN-14 antibody or fragment thereof comprising at least one amino acid from said corresponding FR of said murine MN-14 light chain variable region. Most preferably, the humanized MN-14 antibody or fragment thereof comprises the light chain variable region as set forth in FIG. 13A (middle sequence) or FIG. 22A (hMN-14) or FIG. 23A and the heavy chain variable region set forth in FIG. 14A-C designated as KLHuVhAIGA or FIG. 22B (hMn-14) or FIG. 23B.

The methods of the instant invention may further comprise administering to a subject, either concurrently or sequentially, a therapeutically effective amount of a second humanized, chimeric, human or murine monoclonal antibody or fragment thereof selected from the group consisting of a monoclonal antibody or fragment thereof reactive with EGP-1, EGP-2 (e.g., 17-1A), IL-6, insulin-like growth factor-1, MUC-1, MUC-2, MUC-3, MUC-4, PAM-4, KC4, TAG-72, EGFR, HER2/neu, BrE3, Le-Y, A3, A33, Ep-CAM, AFP, Tn, Thomson-Friedenreich antigens, tumor necrosis antigens, VEGF, placenta growth factor (P1GF) or other tumor angiogenesis antigens, Ga 733, tenascin, fibronectin and a combination thereof. Similarly, the methods may comprise administering to a subject, either concurrently or sequentially, a therapeutically effective amount of a second humanized, chimeric, human or murine monoclonal antibody or fragment thereof selected from the group consisting of a Class I or Class II or Class III anti-CEA monoclonal antibody or fragment thereof as described above. Preferably, the second antibody or fragment thereof is either naked or conjugated to a therapeutic agent.

In a preferred embodiment of the methods described herein, the therapeutic agent is selected from the group consisting of a naked antibody, cytotoxic agent, a drug, a radionuclide, an immunomodulator, a photoactive therapeutic agent, an immunoconjugate of a CEA or non-CEA antibody, a hormone, or a combination thereof, optionally formulated in a pharmaceutically acceptable vehicle. It is also contemplated that the therapeutic agent is not dacarbazine (DTIC).

Preferably, the therapeutic agent is a cytotoxic agent selected from the group consisting of a drug or a toxin. For example, it is contemplated that the drug possesses the pharmaceutical property selected from the group consisting of antimitotic, alkylating, antimetabolite, antiangiogenic, apoptotic, alkaloid, COX-2, and antibiotic agents and combinations thereof. Preferably, the drug is selected from the group consisting of nitrogen mustards, ethylenimine derivatives, alkyl sulfonates, nitrosoureas, triazenes, folic acid analogs, anthracyclines, taxanes, COX-2 inhibitors, pyrimidine analogs, purine analogs, antimetabolites, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, oxaliplatin, doxorubicins and their analogs, and a combination thereof.

When the therapeutic agent is a microbial, plant or animal toxin, the agent can be selected from the group consisting of ricin, abrin, alpha toxin, saporin, ribonuclease (RNase), DNase I, Staphylococcal enterotoxin-A, pokeweed antiviral protein, gelonin, diphtherin toxin, *Pseudomonas* exotoxin, and *Pseudomonas* endotoxin.

It is also contemplated in the methods of the instant invention that the therapeutic agent is an immunomodulator is selected from the group consisting of a cytokine, a stem cell growth factor, a lymphotoxin, a hematopoietic factor, a colony stimulating factor (CSF), an interferon (IFN), a stem cell growth factor, erythropoietin, thrombopoietin and a combination thereof. Preferably, the lymphotoxin is tumor necrosis factor (TNF), said hematopoietic factor is an interleukin (IL), said colony stimulating factor is granulocyte-colony stimulating factor (G-CSF) or granulocyte macrophage-colony stimulating factor (GM-CSF)), said interferon is interferons-α, -β or -γ, and said stem cell growth factor is designated "S1 factor". Also preferred, the immunomodulator comprises IL-1, IL-2, IL-3, IL-6, IL-10, IL-12, IL-18, IL-21, interferon-γ, TNF-α or a combination thereof. Administration of a cytokine prior to, simultaneous with, or subsequent to exposure to a cytotoxic agent that results in myeloid or hematopoietic toxicity is described in U.S. Pat. No. 5,120,525, which is incorporated herein by reference in its entirety.

Also preferred the therapeutic agent is a photoactive therapeutic agent that is a chromogen or dye or an alkylating agent that is dacarbazine.

Also preferred, the therapeutic agent is a radionuclide that has an energy between 20 and 10,000 keV. Preferably, the radionuclide is selected from the group consisting of $^{125}I$, $^{131}I$, $^{90}Y$, $^{88}Y$, $^{225}Ac$, $^{177}Lu$, $^{188}Re$, $^{186}Re$, and combinations thereof.

In another embodiment, an immunomodulator, as described herein, is administered prior to the administration of a therapeutically effective amount of a anti-CEA monoclonal antibody or fragment thereof alone or an immunomodulator is administered prior to the administration of a therapeutically effective amount of a anti-CEA monoclonal antibody and at least one therapeutic agent, wherein any of these components described herein are optionally formulated in a pharmaceutically acceptable vehicle.

BRIEF DESCRIPTION OF THE DRAWINGS

FIG. 1. Graphs comparing tumor volume after treatment with hMN-14 alone, DTIC alone or the combination of hMN-14 and DTIC. FIG. 1A shows DTIC administered alone at 25 and 100 μg/dose or with 250 μg hMN-14 antibody and FIG. 1B shows DTIC administered alone at 50 and 75 μg/dose or with 100 μg hMN-14 antibody.

FIG. 8. Graph comparing the effectiveness of different hMN-14 doses in treating medullary thyroid carcinoma. Animals were given i.v. injections of increasing doses of hMN-14 1 day after s.c. injection of TT cells. Means of respective treametn groups are shown. ♦, untreated; ●, 0.125 mg; ○, 0.25 mg; ■, 0.50 mg; x, 1.0 mg, ▲, 2.0 mg. Error bars represent standard error of the mean and are shown only for the untreated group and the group that received 0.50 mg hMN-14/mouse for clarity.

Figure 11B:
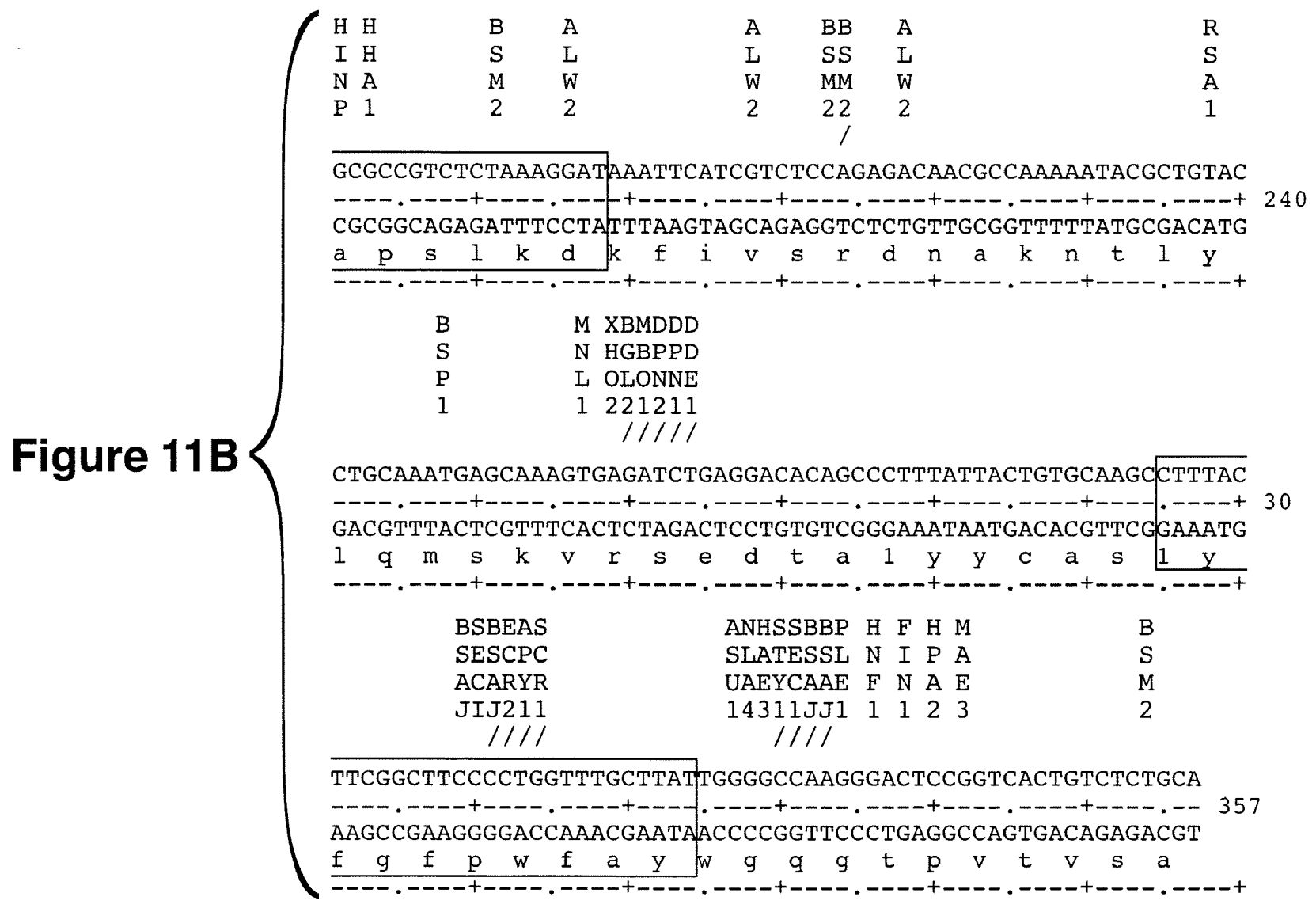

FIG. 11. FIGS. 11A and 11B show the consensus DNA sequence of the murine MN-14 variable region heavy chain (VH) (SEQ ID NO: 1) and the amino acid sequence (SEQ ID NO: 2) encoded by the DNA sequence. The CDRs are enclosed in boxes.

FIG. 12.

FIG. 13.

FIG. 14. FIGS. 14A-14C show a comparison of the amino acid sequence between murine and humanized MN-14 VH framework residues (FR) (SEQ ID NOS 2, 26, 8-11, 27 and 12-15, respectively in order of appearance). Only human FR residues different from the mouse are shown. CDRs for NEWM and KOL are also not shown. The areas of amino acid substitutions in the respective FRs are highlighted in bold, and the position of the substitution indicated according to the Kabat et al. numbering system. The 3 CDRs are boxed.

FIG. 15 shows the effects of naked hMN-14 CEA MAb and DTIC treatment in a human medullary thyroid cancer model.

FIG. 16 shows the effects of naked hMN-14 CEA MAb and CPT-11 treatment in an advanced human colon cancer model.

FIG. 17 shows the effects of naked hMN-14 CEA MAb and CPT-11 treatment in a low tumor burden human colon cancer model.

FIG. 18 shows the effects of pre-treatment with naked hMN-14 CEA MAb given 3 days prior to CPT-11 treatment in a human colon cancer model.

FIG. 19 shows a comparison of various administration sequences of naked hMN-14 CEA Mab and CPT-11 in a human colon cancer model.

FIG. 20 shows the effects of GM-CSF pre-treatment on naked hMN-14 CEA MAb therapy in a human colon cancer model.

FIG. 21 shows a comparison of the effects of naked hMN-14 CEA MAb therapy on both low CEA expression and high (interferon-induced) CEA expression tumor cells in a human colon cancer model.

FIG. 22. FIGS. 22A and 22B show the comparison of the human, murine and humanized sequences of the Vk and VH regions of the human REI and KOL antibodies, respectively with murine and humanized MN-14. The human sequences of the REI Vk (SEQ ID NO: 6) in FIG. 22A are compared with the murine (SEQ ID NO: 4) and humanized (SEQ ID NO: 19) MN-14 Vk sequences. The closed circles indicate sequences retained from the human REI Vk sequences. The CDRs are boxed. The human sequences of the KOL VH (SEQ ID NO: 7) in FIG. 22B are compared with the murine (SEQ ID NO: 2) and humanized (SEQ ID NO: 14) MN-14 VH sequences. The closed circles indicate sequences retained from the human KOL VH sequences. The CDRs are boxed.

FIG. 23. FIGS. 23A and 23B show the Vk, the variable light chain, and the VH, the variable heavy chain sequences of hMN-14, a humanized Class III anti-CEA antibody. The CDR region sequences are shown in bold and underlined. The amino acid residues and the nucleotides are numbered sequentially. The light chain variable region is shown in FIG. 23A (Nucleotide and encoded protein are disclosed as SEQ ID NOS 18 and 19, respectively), and the heavy chain variable region is shown in FIG. 23B (Nucleotide and encoded protein are disclosed as SEQ ID NOS 16 and 17, respectively).

DETAILED DESCRIPTION OF THE PREFERRED EMBODIMENTS

1. Overview

Figure 1B:
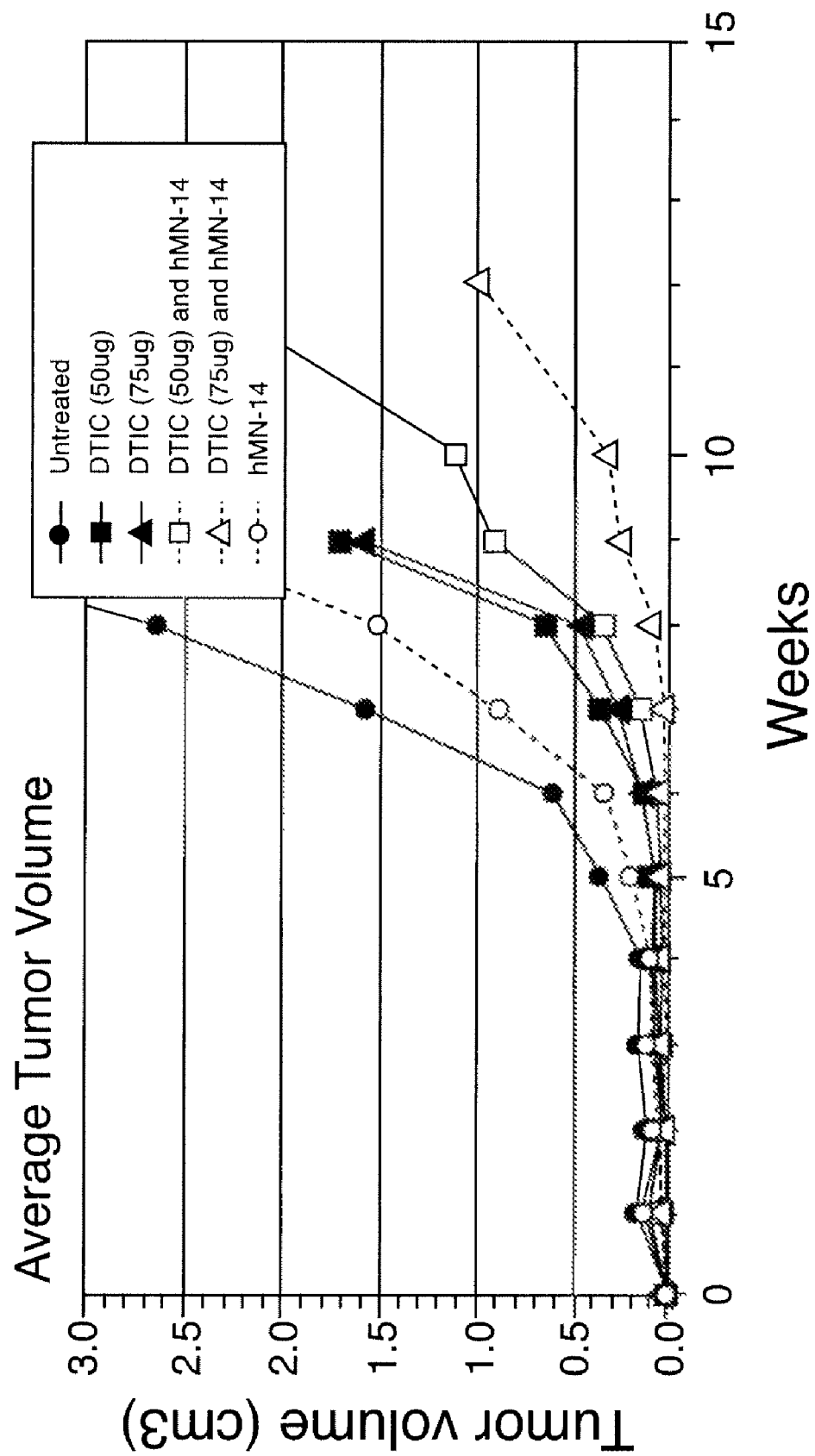

The present invention provides methods of treatment in which a naked anti-CEA antibody or fragment thereof and at least one therapeutic agent are administered either sequentially or concurrently over a treatment period. The method is particularly useful for treating medullary thyroid carcinoma but is surprisingly useful for treating non-medullary thyroid cancers, colorectal cancers, hepatocellular carcinoma, pancreatic, breast, lung, head-and-neck, bladder, uterine and ovarian cancers, and even cancers that do not express CEA at very high levels. For example, treatment is contemplated in cancers that express CEA at levels of at least 100 ng/g of tissue. The present method further provides compositions comprising the anti-CEA antibody, which is preferably a Class III anti-CEA antibody or antibody fragment in which the antibody and the therapeutic agent are not conjugated or linked to each other. As used herein, the phrase "Class III anti-CEA" antibody or antibody fragment means an antibody or fragment that binds the CEA antigen (or CD66e) and is unreactive with normal cross-reactive antigen (NCA), meconium antigen (MA), granulocytes and CD66a-d (see, Primus et al., U.S. Pat. No. 4,818,709, incorporated by reference). The naked Class III anti-CEA antibody or fragment thereof may be a humanized, chimeric, human or murine antibody. In a preferred embodiment, the naked Class III anti-CEA antibody or fragment thereof is a humanized MN-14 antibody or fragment thereof.

Also contemplated for use in the present invention are Class II Mabs that are not CD66a-d cross-reactive. These are Mabs that are reactive with CEA domains N-A1B1, A2B2, which do react with Meconium Antigen, but not with NCA, and do not react with granulocytes. For example, NP-3 and MN-6 are Class II anti-CEA antibodies useful in the present invention. Additionally contemplated for use in the present invention are Class II anti-CEA Mabs or fragments thereof, that may react with CD66a, b and d but not CD66c or Class I Mabs or fragments thereof, that react with CD66a, b, or d as well as CD66c (by definition a Class I Mab binds with CD66c).

Surprisingly, the compositions and methods described herein are also useful for treating non-medullary thyroid carcinoma, including colorectal cancer, pancreatic cancer, breast cancer, lung cancers, hepatocellular carcinoma, urinary bladder cancer, head-and-neck cancers, and ovarian cancer. Because such forms of cancer express less CEA than medullary thyroid cancers, it was unexpected that a naked Class III anti-CEA antibody, in combination with a therapeutic agent, would be useful for treating non-medullary thyroid carcinomas.

The mechanism of tumor cell killing by the naked Class III anti-CEA antibody is not known with certainty and is likely involves several mechanisms. It is hypothesized that the naked antibody alone or in combination with the therapeutic agent may affect tumor growth by blocking biological activities of their respective antigens or by stimulating natural immunological functions, such as antibody-dependent cell-mediated cytotoxicity (ADCC) or complement-mediated lysis. Additionally, the naked antibody alone or in combination with the therapeutic agent may treat and control the cancer by inhibiting cell growth and cell cycle progression, inducing apoptosis, inhibiting angiogenesis, inhibiting metastatic activity, and/or affecting tumor cell adhesion. In fact, the anti-CEA antibody or fragment thereof of the present invention may be more effective in treating metastases than primary cancers, since the metastases may be more susceptible to antagonists of tumor cell adhesion. The present treatment method provides a treatment plan that may be optimized to provide the maximum anti-tumor activity for individual patients by allowing the titration of the antibody and one or more different therapeutic agents to provide an effective treatment regimen.

In one aspect of the present invention, the naked Class III anti-CEA antibody or fragment thereof and therapeutic agent may be supplemented with at least one additional therapeutic agent, such as a naked or conjugated humanized, murine, chimeric or human antibody, fusion protein, or fragment thereof. For example, another class III CEA antibody or antibody fragment that is non-blocking and does not bind granulocytes or CD66a-d; a Class II anti-CEA antibody or antibody fragment that is non-blocking and does not bind granulocytes or CD66a-d; a Class II anti-CEA Mabs or fragments thereof, that may react with CD66a, b and d but not CD66c, Class I Mabs or fragments thereof, that react with CD66a, b, or d as well as CD66c (by definition a Class I Mab binds with CD66c) or an antibody against a different carcinoma-associated epitope or antigen, may be used as the therapeutic agent for combination therapy with the preferred humanized MN-14 antibody. Such an additional antibody, fusion protein or fragment thereof may bind CEA or another cancer or tumor-associated antigen, as described in more detail below.

2. Definitions

In the description that follows, a number of terms are used and the following definitions are provided to facilitate understanding of the present invention.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as $F(ab')_2$, $F(ab)_2$, Fab', Fab, Fv, scFv (single chain Fv) and the like. Regardless of structure, an antibody fragment binds with the same antigen that is recognized by the intact antibody.

The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region. The Fv fragments may be constructed in different ways as to yield multivalent and/or multispecific binding forms. In the former case of multivalent, they react with more than one binding site against the CEA epitope, whereas with multispecific forms, more than one epitope (either of CEA or even against CEA and a different antigen) is bound.

As used herein, the term antibody component includes both an entire antibody, a fusion protein, and fragments thereof.

A naked antibody is generally an entire antibody which is not conjugated to a therapeutic agent. This is so because the Fc portion of the antibody molecule provides effector or immunological functions, such as complement fixation and ADCC (antibody dependent cell cytotoxicity), which set mechanisms into action that may result in cell lysis. However, the Fc portion may not be required for therapeutic function of the antibody, but rather other mechanisms, such as apoptosis, anti-angiogenesis, anti-metastatic activity, anti-adhesion activity, such as inhibition of heterotypic or homotypic adhesion, and interference in signaling pathways, may come into play and interfere with the disease progression. Naked antibodies include both polyclonal and monoclonal antibodies, and fragments thereof, that include murine antibodies, as well as certain recombinant antibodies, such as chimeric, humanized or human antibodies and fragments thereof. As defined in the present invention, "naked" is synonymous with "unconjugated," and means not linked or conjugated to the therapeutic agent with which it administered.

A chimeric antibody is a recombinant protein that contains the variable domains of both the heavy and light antibody chains, including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, is transferred from the heavy and light variable chains of the rodent antibody into human heavy and light variable domains. The constant domains of the antibody molecule is derived from those of a human antibody.

A human antibody is an antibody obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993).

Human antibodies may also be generated by in vitro activated B cells. See U.S. Pat. Nos. 5,567,610 and 5,229,275, which are incorporated in their entirety by reference.

A therapeutic agent is a molecule or atom which is administered separately, concurrently or sequentially with an antibody component, i.e., an antibody or antibody fragment, or a subfragment thereof, and is useful in the treatment of a disease. Examples of therapeutic agents include antibodies, antibody fragments, immunoconjugates, drugs, cytotoxic agents, toxins, nucleases, hormones, immunomodulators, chelators, boron compounds, photoactive agents or dyes, radioisotopes or radionuclides, antisense oligonucleotides, immunoconjugates or combinations thereof.

An immunoconjugate is an antibody component conjugated to a therapeutic agent. Suitable therapeutic agents are described above.

As used herein, the term antibody fusion protein is a recombinantly-produced antigen-binding molecule in which two or more of the same or different natural antibody, single-chain antibody or antibody fragment segments with the same or different specificities are linked. A Class III anti-CEA fusion protein comprises at least one CEA binding site. Preferably, the Class III anti-CEA fusion protein is a MN-14 fusion protein.

Valency of the fusion protein indicates the total number of binding arms or sites the fusion protein has to antigen(s) or epitope(s); i.e., monovalent, bivalent, trivalent or multivalent. The multivalency of the antibody fusion protein means that it can take advantage of multiple interactions in binding to an antigen, thus increasing the avidity of binding to the antigen, or to different antigens. Specificity indicates how many different types of antigen or epitope an antibody fusion protein is able to bind; i.e., monospecific, bispecific, trispecific, multispecific. Using these definitions, a natural antibody, e.g., an IgG, is bivalent because it has two binding arms but is monospecific because it binds to one type of antigen or epitope. A monospecific, multivalent fusion protein has more than one binding site for the same antigen or epitope. For example, a monospecific diabody is a fusion protein with two binding sites reactive with the same antigen. The fusion protein may comprise a multivalent or multispecific combination of different antibody components or multiple copies of the same antibody component. For example, the fusion protein of the present invention may be multispecific, wherein one arm of the fusion protein (e.g., scFv or Fab) is a Class III, anti-CEA mAb that targets CD66e and another arm of the fusion protein is from another CEA crossreactive antibody that targets CD66a-d.

A preferred bispecific fusion protein according to the invention has an arm against a Class III CEA epitope, and a second arm against CD66a-d epitopes (Class II) expressed on granulocytes. In these embodiments, the CD66a-d binding portion should not be able to fix complement or bind to Fc-receptors to effect ADCC (which would result in release of cytokines from granulocytes). Though complement fixation and effecting ADCC are preferred properties for the naked therapy embodiments of the present invention, they should be avoided in the context of the instant embodiments relating to bispecific fusion proteins. On normal colon cells NCA-50/90 and CEA are both expressed, but they are restricted to the apical face of the normal epithelial cell, and this face is presented only to the colon lumen, and not accessible to injected antibody. CEA released from these normal cells as CEA, or bound to dead normal cells is eliminated in the feces. This polarization is lost when a colon cancer develops, and both NCA-50/90 and CEA are then expressed on the cancer cell membrane that is invading the underlying normal basement membrane which anchors the normal epithelial cells. A bispecific antibody such as hMN3/hMN14 is expected to react with both CEA and NCA-50/90 on these invading cells. Furthermore, as NCA50/90 is present on granulocytes this bispecific is expected to direct granulocytes to kill the invading colon cancer cells. An even more preferred construct according to this embodiment is a bispecific, trivalent protein with one arm reactive with NCA50/90 and two arms reactive with only CEA. Another embodiment would be a bispecific protein with two arms that bind to NCA50/90.

A preferred fusion protein also reactive with granulocytes would be a diabody, having one arm against NCA-50/90 (example hMN-3), and one arm against a Class III epitope on CEA (hMN14). These fusion proteins do not have an Fc-domain so they will not activate cytokine release from granulocytes. An even more preferred fusion protein would be a triabody with one hMN-3 arm and two hMN14 arms. The construction of such diabodies and triabodies is disclosed in U.S. application Ser. Nos. 60/404,919 (filed Aug. 22, 2002), 60/345,641 (filed Jan. 8, 2002), 60/328,835 (filed Oct. 15, 2001), and 60/341,881 (filed Dec. 21, 2001).

Any kind of multispecific antibody made with mabs of the hMN14/NP-3 specificities are also preferred and can have an Fc-domain able to fix complement/activate ADCC. For example, a hMN14-IgG1/[NP-3-scFv]2 fusion protein could be used; the making of which is taught in U.S. application Ser. No. 09/337,756.

Yet another preferred type of multispecific antibody according to the present invention is an hMN-3 MAb which has an Fc-domain lacking the ability to fix complement/effect-ADCC.

The fusion protein may additionally comprise a therapeutic agent. For example, where at least one of the antibodies or fragments thereof, such as the Class III, anti-CEA mAb that targets CD66e or its scFv or Fab may be conjugated to cytokines, such as interferon or a colony-stimulating factor, such as GM-CSF or G-CSF or an interleukin, all of which are described herein.

An immunomodulator is a therapeutic agent as defined in the present invention that when present, alters, suppresses or stimulates the body's immune system. Typically, the immunomodulator useful in the present invention stimulates immune cells to proliferate or become activated in an immune response cascade, such as macrophages, B-cells, and/or T-cells. An example of an immunomodulator as described herein is a cytokine, which is a soluble small protein of approximately 5-20 kDa that are released by one cell population (e.g., primed T-lymphocytes) on contact with specific antigens, and which act as intercellular mediators between cells. As the skilled artisan will understand, examples of cytokines include lymphokines, monokines, interleukins, and several related signalling molecules, such as tumor necrosis factor (TNF) and interferons. Chemokines are a subset of cytokines. Certain interleukins and interferons are examples of cytokines that stimulate T cell or other immune cell proliferation.

Preparation of Monoclonal Antibodies, Including Chimeric, Humanized and Human Antibodies Monoclonal antibodies (MAbs) are a homogeneous population of antibodies to a particular antigen and the antibody comprises only one type of antigen binding site and binds to only one epitope on an antigenic determinant. Rodent monoclonal antibodies to specific antigens may be obtained by methods known to those skilled in the art. See, for example, Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

Abs to peptide backbones are generated by well-known methods for Ab production. For example, injection of an immunogen, such as (peptide)$_n$-KLH, wherein KLH is keyhole limpet hemocyanin, and n=1-30, in complete Freund's adjuvant, followed by two subsequent injections of the same immunogen suspended in incomplete Freund's adjuvant into immunocompetent animals. The animals are given a final i.v. boost of antigen, followed by spleen cell harvesting three days later. Harvested spleen cells are then fused with Sp2/0-Ag14 myeloma cells and culture supernatants of the resulting clones analyzed for anti-peptide reactivity using a direct-binding ELISA. Fine specificity of generated Abs can be analyzed for by using peptide fragments of the original immunogen. These fragments can be prepared readily using an automated peptide synthesizer. For Ab production, enzyme-deficient hybridomas are isolated to enable selection of fused cell lines. This technique also can be used to raise antibodies to one or more of the chelates comprising the linker, e.g., In(III)-DTPA chelates. Monoclonal mouse antibodies to an In(III)-di-DTPA are known (U.S. Pat. No. 5,256,395 to Barbet).

Another method for producing antibodies is by production in the milk of transgenic livestock. See, e.g., Colman, A., *Biochem. Soc. Symp.*, 63: 141-147, 1998; U.S. Pat. No. 5,827,690, both of which are incorporated in their entirety by reference. Two DNA constructs are prepared which contain, respectively, DNA segments encoding paired immunoglobulin heavy and light chains. The DNA segments are cloned into expression vectors that contain a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

After the initial raising of antibodies to the immunogen, the variable genes of the monoclonal antibodies can be cloned from the hybridoma cells, sequenced and subsequently prepared by recombinant techniques. General techniques for cloning murine immunoglobulin variable domains are described, for example, by the publication of Orlandi et al., *Proc. Nat'l Acad. Sci. USA* 86: 3833 (1989), which is incorporated by reference in its entirety. Humanization and chimerization of murine antibodies and antibody fragments are well known to those skilled in the art. A chimeric antibody is a recombinant protein that contains the variable domains including the CDRs derived from one species of animal, such as a rodent antibody, while the remainder of the antibody molecule; i.e., the constant domains, is derived from a human antibody. The use of antibody components derived from humanized and chimerized monoclonal antibodies alleviates potential problems associated with the immunogenicity of murine constant regions. Techniques for constructing chimeric antibodies are well known to those of skill in the art. As an example, Leung et al., *Hybridoma* 13:469 (1994), describe how they produced an LL2 chimera by combining DNA sequences encoding the $V_k$ and $V_H$ domains of LL2 monoclonal antibody, an anti-CD22 antibody, with respective human K and IgG$_1$ constant region domains.

A chimeric monoclonal antibody (MAb) can also be humanized by replacing the sequences of the murine FR in the variable domains of the chimeric MAb with one or more different human FR. Specifically, humanized monoclonal antibodies are produced by transferring mouse complementary determining regions from heavy and light variable chains of the mouse immunoglobulin into a human variable domain, and then, substituting human residues in the framework regions of the murine counterparts. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988).

In a preferred embodiment, some human residues in the framework regions of the humanized anti-CEA antibody or fragments thereof are replaced by their murine counterparts. Additionally, knowing that chimeric anti-CEA exhibits a binding affinity comparable to that of its murine counterpart, defective designs, if any, in the original version of the humanized anti-CEA MAb can be identified by mixing and matching the light and heavy chains of the chimeric anti-CEA to those of the humanized version. Preferably, the humanized anti-CEA antibody is a humanized MN-14 antibody, and it preparation and sequences are disclosed in U.S. Pat. No. 5,874,540, which is incorporated in its entirety by reference. Although the two human antibodies are REI and NEWM are the preferred antibodies for preparing both humanized and chimeric MN-14 antibodies, a combination of framework sequences from 2 or more different human antibodies can be used for $V_H$ and $V_K$. The production of humanized MAbs are described, for example, by Jones et al., *Nature* 321: 522 (1986), Riechmann et al., *Nature* 332:323 (1988), Verhoeyen et al., *Science* 239:1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993), each of which is hereby incorporated by reference. Further, the affinity of humanized, chimeric and human MAbs to a specific epitope can be increased by mutagenesis of the CDRs, so that a lower dose of antibody may be as effective as a higher dose of a lower affinity MAb prior to mutagenesis. See for example, WO0029584A1.

In another embodiment, an antibody of the present invention is a human Class III anti-CEA monoclonal antibody. The anti-CEA MAb, or another human antibody, can be obtained from a transgenic non-human animal. See, e.g., Mendez et al., *Nature Genetics*, 15: 146-156 (1997) and U.S. Pat. No. 5,633,425, which are incorporated in their entirety by reference. For example, a human antibody can be recovered from a transgenic mouse possessing human immunoglobulin loci. Preferably, the anti-CEA antibody is an MN-14 antibody. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Unrearranged human immunoglobulin genes also can be introduced into mouse embryonic stem cells via microcell-mediated chromosome transfer (MMCT). See, e.g., Tomizuka et al., *Nature Genetics,* 16: 133 (1997). In this methodology microcells containing human chromosomes are fused with mouse embryonic stem cells. Transferred chromosomes are stably retained, and adult chimeras exhibit proper tissue-specific expression.

As an alternative, an antibody or antibody fragment of the present invention may be derived from human antibody fragments isolated from a combinatorial immunoglobulin library. See, e.g., Barbas et al., *METHODS: A Companion to Methods in Enzymology* 2:119 (1991), and Winter et al., *Ann. Rev. Immunol.* 12: 433 (1994), which are incorporated by reference. Many of the difficulties associated with generating monoclonal antibodies by B-cell immortalization can be overcome by engineering and expressing antibody fragments in *E. coli*, using phage display. To ensure the recovery of high affinity, monoclonal antibodies a combinatorial immunoglobulin library must contain a large repertoire size. A typical strategy utilizes mRNA obtained from lymphocytes or spleen cells of immunized mice to synthesize cDNA using reverse transcriptase. The heavy- and light-chain genes are amplified separately by PCR and ligated into phage cloning vectors. Two different libraries are produced, one containing the heavy-chain genes and one containing the light-chain genes. Phage DNA is isolated from each library, and the heavy- and light-chain sequences are ligated together and packaged to form a combinatorial library. Each phage contains a random pair of heavy- and light-chain cDNAs and upon infection of *E. coli* directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for producing a human immunoglobulin phage library can be obtained, for example, from STRATAGENE Cloning Systems (La Jolla, Calif.).

In one embodiment, the antibodies of the present invention are produced as described in Hansen et al., U.S. Pat. No. 5,874,540; Hansen et al., *Cancer,* 71:3478 (1993); Primus et al., U.S. Pat. No. 4,818,709, and Shively et al., U.S. Pat. No. 5,081,235, which have been incorporated by reference in their entirety.

Production of Antibody Fragments

The present invention contemplates the use of fragments of a Class III anti-CEA antibody, preferably a MN-14 antibody. The Class III anti-CEA antibody or fragment thereof of the present invention does not bind granulocytes or CD66a-d. Antibody fragments which recognize specific epitopes can be generated by known techniques. For example, antibody fragments can be prepared by proteolytic hydrolysis of an antibody or by expression in *E. coli* of the DNA coding for the fragment. The antibody fragments are antigen binding portions of an antibody, such as F(ab')$_2$, Fab', Fab, Fv, scFv and the like, and can be obtained by pepsin or papain digestion of whole antibodies by conventional methods.

For example, an antibody fragment can be produced by enzymatic cleavage of antibodies with pepsin to provide a 100 Kd fragment denoted F(ab')$_2$. This fragment can be further cleaved using a thiol reducing agent, and optionally a blocking group for the sulfhydryl groups resulting from cleavage of disulfide linkages, to produce 50 Kd Fab' monovalent fragments. Alternatively, an enzymatic cleavage using papain produces two monovalent Fab fragments and an Fc fragment directly. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described in Inbar et al., *Proc. Nat'l. Acad. Sci. USA* 69:2659 (1972). Alternatively, the variable chains can be linked by an intermolecular disulfide bond or cross-linked by chemicals such as glutaraldehyde. See, for example, Sandhu, *Crit. Rev. Biotech.* 12:437 (1992).

Preferably, the Fv fragments comprise $V_H$ and $V_L$ chains which are connected by a peptide linker. These single-chain antigen binding proteins (sFv) are prepared by constructing a structural gene comprising DNA sequences encoding the $V_H$ and $V_L$ domains which are connected by an oligonucleotide. The structural gene is inserted into an expression vector that is subsequently introduced into a host cell, such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology*, 2:97 (1991). Also see Bird et al., *Science* 242:423 (1988), Ladner et al., U.S. Pat. No. 4,946,778; Pack et al., *Bio Technology* 11:1271 (1993) and Sandhu, supra.

Another form of an antibody fragment is a peptide coding for a single complementarity-determining region (CDR). A CDR is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2:106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

Humanized, Chimeric and Human Anti-CEA Antibodies for Treatment

Described in the present invention are compositions and methods using murine, chimeric, humanized and human Class III anti-CEA antibodies and fragments thereof for treatment. Preferably, the Class III anti-CEA antibody or fragment thereof is a MN-14 antibody or fragment thereof. The antibodies of the present invention can be used to treat medullary thyroid carcinoma (MTC), as well as non-MTC CEA-expressing carcinomas. Exemplary non-MTC CEA expressing carcinomas include colorectal cancer, pancreatic cancer, hepatocellular carcinoma, gastric cancer, lung cancer, head- and neck cancers, urinary bladder cancer, uterine cancer, breast cancer, and ovarian cancer.

Compositions

Contemplated herein is a composition comprising at least one Class III anti-CEA monoclonal antibody (MAb) or fragment thereof and at least one therapeutic agent, which are not conjugated to each other, and thus are present in the composition as unconjugated forms of each of the components. In compositions comprising more than one antibody or antibody fragments, such as a second Class III anti-CEA antibody, the second antibody is non-blocking (i.e., does not block binding of the first Class III anti-CEA antibody or antibody fragment).

In one embodiment, the Class III anti-CEA monoclonal antibody or fragment thereof is humanized, chimeric, or fully human, wherein the humanized, chimeric, or fully human MAb retains substantially the Class III anti-CEA binding specificity of a murine Class III anti-CEA MAb.

In a preferred embodiment, the Class III anti-CEA monoclonal antibody or fragment thereof is a MN-14 antibody or fragment thereof. Preferably, the MN-14 monoclonal antibody or fragment thereof comprises the complementarity-determining regions (CDRs) of a murine MN-14 monoclonal antibody, wherein the CDRs of the light chain variable region of said MN-14 antibody comprises CDR1 comprising the amino acid sequence KASQDVGTSVA (SEQ ID NO: 20); CDR2 comprising the amino acid sequence WTSTRHT (SEQ ID NO: 21); and CDR3 comprising the amino acid sequence QQYSLYRS (SEQ ID NO: 22); and the CDRs of the heavy chain variable region of said Class III anti-CEA antibody comprises CDR1 comprising TYWMS (SEQ ID NO: 23); CDR2 comprising EIHPDSSTINYAPSLKD (SEQ ID NO: 24); and CDR3 comprising LYFGFPWFAY (SEQ ID NO: 25). Also preferred, the MN-14 monoclonal antibody reacts with CEA and is unreactive with normal cross-reactive antigen (NCA) and meconium antigen (MA). However, antibodies against these cross-reactive determinants may be used in combination therapy with CEA-specific antibodies, such as combined with the MN-14 monoclonal antibody.

Figure 13A:
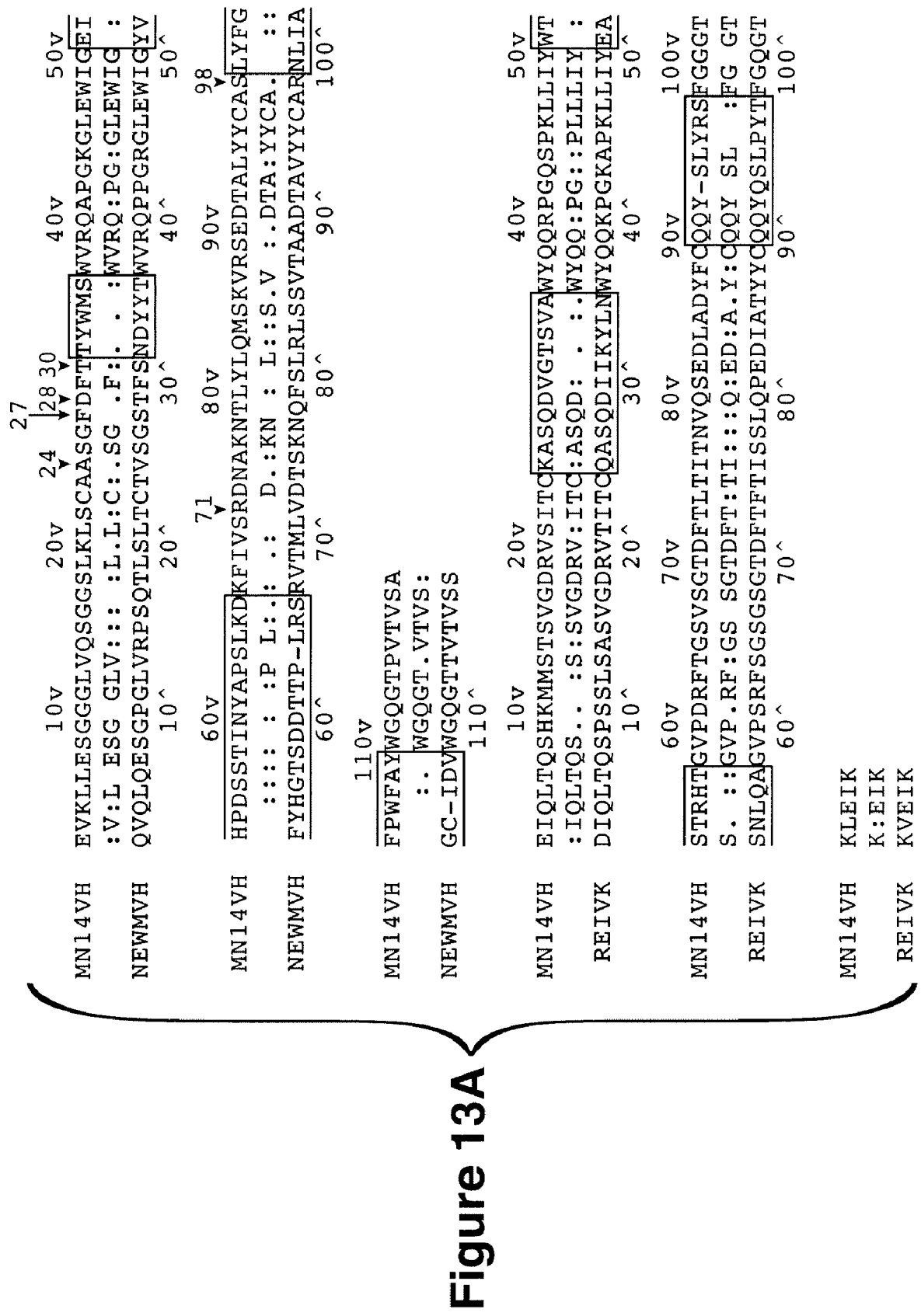
FIGS. 13A and 13B show the alignment of the murine MN-14 variable region (MN14VH is shown in SEQ ID NO: 2, MN14VK is shown in SEQ ID NO: 4) of the with the human variable regions NEWM VH (SEQ ID NO: 5) and REI VK (SEQ ID NO: 6) (FIG. 13A), and with the human KOL VH region (SEQ ID NO: 7) (FIG. 13B). CDRs are boxed, and the murine VH FRs, which are incorporated into the humanized VH, are marked with their positions according to the numbering system of Kabat et al. SEQUENCES OF PROTEINS OF IMMUNOLOGICAL INTEREST, U.S. Government Printing Office, Washington, D.C., 1987. Murine residues outside the CDRs that were included in the KLHuVH are indicated by a filled circle.
Figure 13B:
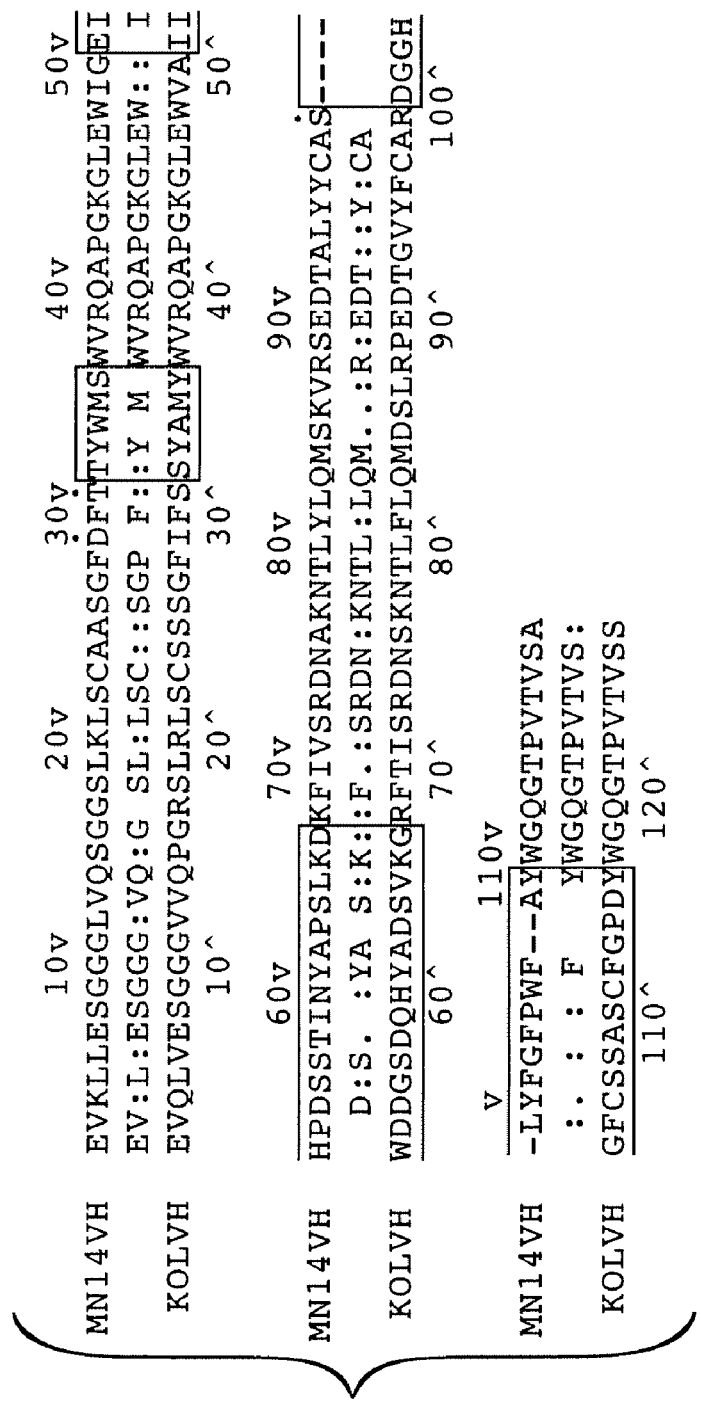
Figure 14C:
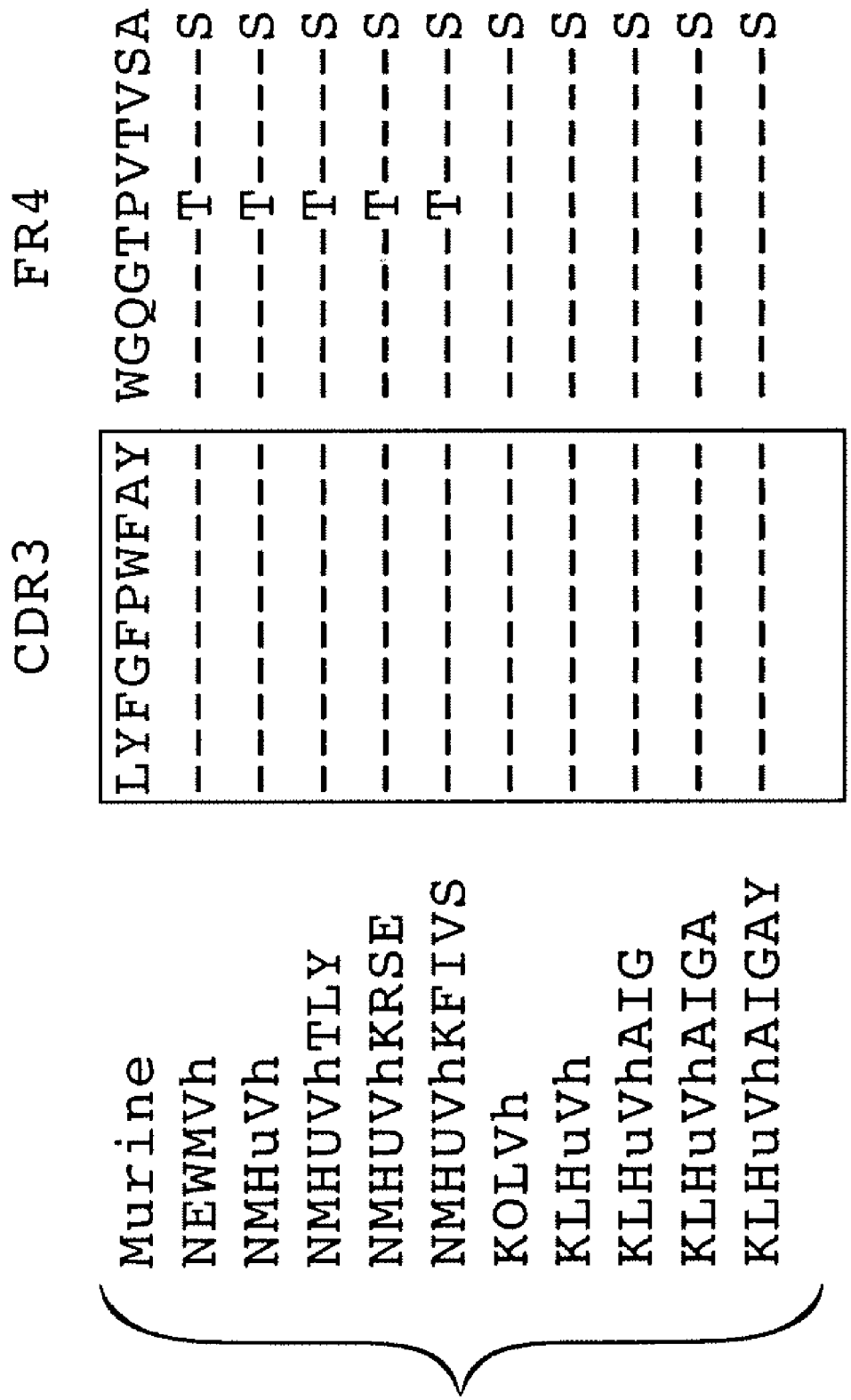

In another embodiment of the present invention, the MN-14 monoclonal antibody or fragment thereof is a humanized or fully human MN-14 antibody or fragment thereof. The framework regions (FRs) of the light and heavy chain variable regions of the humanized MN-14 antibody or fragment thereof preferably comprise at least one amino acid substituted from the corresponding FRs of a murine MN-14 monoclonal antibody. Still preferred, the humanized MN-14 antibody or fragment thereof comprises at least one amino acid from the corresponding FR of the murine MN-14 antibody selected from the group consisting of amino acid residue 24, 28, 30, 48, 49, 74 and 94 of the murine heavy chain variable region (KLHuVhAIGA) of FIG. 14A-C as noted above. The amino acid sequence of a preferred humanized heavy chain variable region is also set forth in Hansen et al., U.S. Pat. No. 5,874,540, which is incorporated by reference in its entirety. Also preferred, the humanized heavy chain variable region comprises the amino acid sequence set forth in FIGS. 14A-C, designated as KLHuVhAIG and KLHuVhAIGAY. In another embodiment, the humanized MN-14 antibody or fragment thereof comprises at least one amino acid from the corresponding FR of the murine MN-14 light chain variable region. Most preferably, the humanized MN-14 antibody or fragment thereof comprises the light chain variable region of FIG. 13A or FIG. 22A or FIG. 23A. Another embodiment of the present invention is a composition comprising a chimeric MN-14 monoclonal antibody or fragment thereof and at least one therapeutic agent, which are not conjugated to each other, and thus are present in the composition as unconjugated forms of each of the components. Preferably, the chimeric MN-14 antibody or fragment thereof comprises the CDRs of the murine MN14 light chain variable region set forth in FIG. 13A or FIG. 22A or FIG. 23A and the CDRs of the murine MN14 heavy chain variable region as set forth in FIGS. 14A-C or FIG. 22B or FIG. 23B.

Also described herein is a composition comprising a naked murine, humanized, chimeric or human Class III anti-CEA antibody or fragment thereof and a therapeutic agent, and a second naked or conjugated Class III anti-CEA antibody or antibody fragment thereof, that is non-blocking, i.e., does not block binding of the first Class III anti-CEA antibody or fragment thereof, and formulated in a pharmaceutically acceptable vehicle. In other words, both Class III anti-CEA antibodies or fragments thereof are non-blocking to each other, thus, allowing both antibodies or fragments thereof to bind to CEA (CD66e). Additionally, the Class III CEA antibody or antibody fragment of the present invention, as well as those for use in combination therapy, do not bind granulocytes or CD66a-d. Other Class III antibodies suitable for combination therapy as a naked antibody or as a component of an immunoconjugate, with the naked Class III anti-CEA antibody of antibody fragment of the present invention include the non-blocking antibodies or fragments thereof described in Kuroki et al., *JP J. Cancer Res.,* 78(4):386 (1987) and Hammarstrom (Cancer Res. 52(8):2329 (1992)), that also do not bind granulocytes or CD66a-d.

Additionally, other anti-CEA antibodies, such as Class II or Class I anti-CEA antibodies, can be used in combination with the Class III anti-CEA antibody of the present invention, in either a naked or conjugated form. Such Class II antibodies or antibody fragments that can be used for combination therapy are non-blocking and do not bind granulocytes or CD66a-d but are reactive with meconium antigen (MA) and CEA. For example, one or more chimeric or humanized Class II anti-CEA antibody or fragment thereof, such as MN-6 or NP-3, may be combined with a Class III anti-CEA antibody or fragment thereof of the present invention. These two antibodies do not react with CD66a-d or with granulocytes (Hansen et al., *Cancer Jun.* 1, 1993; 71(11):3478-85). A number of publications disclose MAbs that recognize CEA and different members of the CEA gene family, such as Thompson et al., *J. Clin. Lab. Anal.* 5:344 (1991); Kuroki et al., *J. Biol. Chem.* 266:11810 (1991); Nagel et al., *Eur. J. Biochem.* 214:27 (1993); Skubitz et al., *J. Immunol.* 155:5382 (1995); Skubitz et al., *J. Leukoc. Biol.* 60:106 (1996); and Chen et al., *Proc. Natl. Acad. Sci. USA* 93:14851 (1996).

Moreover, the second antibody or antibody fragment is either unconjugated (naked) or conjugated to at least one therapeutic agent (immunoconjugate) Immunoconjugates can be prepared by indirectly conjugating a therapeutic agent to an antibody component. General techniques are described in Shih et al., *Int. J. Cancer,* 41:832 (1988); Shih et al., *Int. J. Cancer,* 46:1101 (1990); and Shih et al., U.S. Pat. No. 5,057, 313. The general method involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate. Preferably, the anti-CEA antibody or fragment thereof in the composition for treatment is a MN-14 antibody or fragment thereof. More preferred, the MN-14 antibody or fragment thereof is humanized.

Also contemplated in the present invention is a composition comprising a naked humanized, chimeric, murine or human Class III anti-CEA antibody or fragment thereof and a therapeutic agent, and a conjugated or unconjugated second antibody or antibody fragment thereof. In one embodiment, the second antibody or fragment thereof is unconjugated (naked) or conjugated to at least one therapeutic agent. Non Class I, Class II or Class III anti-CEA antibodies and fragments thereof that are suitable for combination therapy include, but are not limited to, carcinoma-associated antibodies and fragments thereof. Examples of carcinoma associated antibodies and antibody fragments bind EGP-1, EGP-2 (e.g., 17-1A), MUC-1, MUC-2, MUC-3, MUC-4, PAM-4, KC4, TAG-72, EGFR, HER2/neu, BrE3, Le-Y, A3, A33, Ep-CAM, AFP, Tn, Thomson-Friedenreich antigens, tumor necrosis antigens, VEGF, P1GF or other tumor angiogenesis antigens, Ga 733, IL-6, insulin-like growth factor-1, tenascin, fibronectin or a combination thereof. As discussed supra, non-blocking Class II and Class III anti-CEA MAbs that do not bind CD66a-d or granulocytes or alternatively, Class II anti-CEA MAbs that do bind CD66a, b and d or Class I anti-CEA MAbs that bind CD66a, b and d, as well as CD66c, may also be used in combination with Class III CEA antibodies. Other antibodies and antibody fragments suitable for combination therapy also include those targeted against oncogene markers or products, or antibodies against tumor-vasculature markers, such as the angiogenesis factor, Placental Growth Factor (P1GF), and antibodies against certain immune response modulators, such as antibodies to CD40.

Methods

Also described in the present invention are methods for treating medullary thyroid carcinoma and non-medullary thyroid carcinomas. Non-medullary thyroid carcinomas include colorectal cancer and any other CEA expressing tumor, such as pancreatic cancer, breast cancer, hepatocellular carcinoma, ovarian cancer, certain kinds of lung, head-and-neck, endometrial, bladder, and liver cancers that express variable quantities of CEA. The CEA levels in these types of cancers are much lower than present in medullary thyroid carcinomas but all that is necessary is that the CEA levels be sufficiently high so that the Class III anti-CEA therapy provides an effective treatment. Normal colon mucosa has about 100-500 ng/gram but carcinomas expressing CEA at levels of about 5 mcg/gram of tissue are suitable for treatment with the methods described in the instant invention.

For example, contemplated herein is a method for treating medullary thyroid carcinoma or non-medullary thyroid carcinoma comprising administering to a subject, either concurrently or sequentially, a therapeutically effective amount of a Class III anti-CEA monoclonal antibody or fragment thereof and at least one therapeutic agent, and optionally formulated in a pharmaceutically acceptable vehicle. Preferably, the Class III anti-CEA monoclonal antibody or fragment thereof is chimeric, murine, humanized or human, wherein the chimeric, humanized, murine, or human Class III anti-CEA MAb retains substantially the Class III anti-CEA binding specificity of the murine MAb. More preferably, the Class III anti-CEA antibody is humanized, and most preferably, the humanized MN-14 monoclonal antibody, as described herein and in U.S. Pat. No. 5,874,540. Preferably the therapeutic agent is a cytotoxic agent, more preferably an alkylating agent, and most preferably, dacarbazine (DTIC). But in another embodiment, the therapeutic agent may also not be DTIC. Other classes of anti-cancer cytostatic and cytotoxic agents, such as 5-fluorouracil, CPT-11 (which is also known as irinotecan and camptosar) and oxaliplatin can also be used in combinations with these antibodies, especially in the therapy of colorectal cancers. In other cancer types, cancer drugs that are known to be effective are also good candidates for combining with the antibody therapies proposed herein.

Also contemplated herein is a method for treating medullary thyroid carcinoma and non-medullary thyroid carcinoma comprising administering to a subject, either concurrently or sequentially, a therapeutically effective amount of a first Class III anti-CEA monoclonal antibody or fragment thereof and at least one therapeutic agent, and a naked or conjugated second humanized, chimeric, human or murine monoclonal antibody or fragment thereof, and optionally formulated in a pharmaceutically acceptable vehicle. Preferably, the first Class III anti-CEA MAb is a humanized MN-14 antibody or fragment thereof. In one embodiment, the second antibody or fragment thereof is a carcinoma-associated antibody or fragment thereof selected from the group consisting of a monoclonal antibody or fragment thereof reactive with TAG-72, EGFR, HER2/neu, MUC1, MUC2, MUC3, MUC4, EGP-1, EGP-2, AFP, Tn, IL-6, insulin growth factor-1, or another such tumor-associated antigen, as described above. In another embodiment, the second antibody or fragment thereof can be a different Class III anti-CEA antibody or fragment thereof that is non-blocking and does not bind granulocytes or CD66a-d.

In another embodiment, the second anti-CEA antibody is a Class II antibody or fragment thereof, such as those described in Hammarstrom and Kuroki, provided that they do not bind granulocytes or CD66a-d. In another embodiment, this antibody includes Class I MAbs or fragments thereof, that react with CD66a, b, or d as well as CD66c. The antibodies and fragments thereof may be administered either concurrently or sequentially with each other or the therapeutic agent. In one embodiment, the second antibody or fragment thereof is either naked or conjugated to a therapeutic agent.

Accordingly, the present invention contemplates the administration of naked murine, humanized, chimeric and human anti-CEA antibodies and fragments thereof sequentially or concurrently with one or more therapeutic agents, or administered as a multimodal therapy. A Class III, anti-CEA antibody is preferred but any anti-CEA antibody that targets tumor cells are useful in the present invention. A naked Class III anti-CEA antibody as described herein can significantly increase the chemosensitivity of cancer cells to one or more therapeutic agents. For example, treatment of colon cancer cells with a naked Class III, anti-CEA antibody, MN-14 as described herein, either before or concurrently with a therapeutic agent, such as CPT-11, 5'-fluorouracil (5-FU) or oxaliplatin, improves a cell's response to a therapeutic agent, such as a cytotoxic drug. Further, these therapeutic methods of treatment with a naked Class III, anti-CEA antibody alone or in combination with a therapeutic agent can be further enhanced by administering an immunomodulator as described herein, prior to the administration of the naked antibody or the administration of the naked antibody and at least one of the therapeutic agents.

Multimodal therapies of the present invention include immunotherapy with a Class III anti-CEA antibody or fragment thereof, and a therapeutic agent, supplemented with administration of an unconjugated or conjugated antibody, unconjugated or conjugated fusion protein, or fragment thereof. For example, an unconjugated humanized, chimeric, murine or human MN-14 MAb or fragment thereof may be combined with another naked humanized, murine, chimeric or human Class III anti-CEA antibody (such as an antibody against a different epitope on CEA and also does not bind granulocytes or CD66a-d), or a humanized, chimeric, murine or human Class III anti-CEA antibody immunoconjugate conjugated to a radioisotope, chemotherapeutic agent, cytokine, enzyme, enzyme-inhibitor, hormone or hormone antagonist, metal, toxin, antisense oligonucleotide (e.g., anti-bcl-2), or a combination thereof. A naked Class III anti-CEA antibody or fragment thereof may also be combined with a conjugated or unconjugated fusion protein of a murine, humanized, chimeric or human Class III anti-CEA antibody. However, the Class III anti-CEA antibodies for combination therapy are non-blocking to each other and unable to bind granulocytes or CD66a-d. Preferably, the naked Class III anti-CEA antibody is administered sequentially or concurrently with the second naked or conjugated antibody, fusion protein, or fragment thereof. Also preferred, one of the antibodies or antibody fragments for use in combination therapy is a naked humanized MN-14 antibody or fragment thereof. Additionally, the second antibody used as a naked or conjugated antibody, fusion protein, or fragment thereof, may be a human, humanized, chimeric or murine Class II CEA antibody or fragment thereof that is non-blocking and does not bind granulocytes or CD66a-d. A preferred combination of antibodies according to this embodiment would include a naked cross reactive anti-CD66a-d antibody which lacks an effector function, which does not activate complement and does not induce cytokine release. In addition, a cross reactive anti-CD66a-d Fab' or even a F(ab')$_2$ would likely not damage granulocytes and could be used with a Class III anti-CEA MAb or a Class II anti-CEA MAb of the NP-3 type.

In the methods described herein, subjects receive at least one naked Class III anti-CEA antibody or fragment thereof, administered before, after or in conjunction with a therapeutic agent. In one embodiment, a Class III anti-CEA antibody is used for pretreating cells, i.e., administered before a therapeutic agent. Preferably, the class III anti-CEA antibody is an MN-14 antibody, such as a humanized MN-14 (hMN-14) that is administered at least one hour before a therapeutic agent, such as 5-FU or CPT-11.

Preferably, the therapeutic agent is a drug used in standard cancer chemotherapy, such as taxane or platinum drugs in ovarian cancer, fluorouracil, CPT-11, and oxaloplatin drugs in colorectal cancer, gemcitabine in pancreatic and other cancers, or taxane derivatives in breast cancers. COX-2 inhibitors represent still another class of agents that show activity in combination with typical cytotoxic agents in cancer chemotherapy, and can be used in this invention in the same way, but combined in addition with CEA antibodies alone and in combination with other cancer-associated antibodies. Optionally, these drugs can be used in combination with radiolabeled antibodies, either CEA antibody conjugates or radioconjugates with other carcinoma-associated antibodies, of the kinds described above. Also preferred, the Class III anti-CEA antibody or fragment thereof is a MN-14 antibody or fragment thereof. Still preferred, the MN-14 antibody or fragment thereof is humanized.

In a preferred embodiment, a naked Class III anti-CEA antibody or fragment thereof is administered sequentially (either prior to or after) or concurrently with dacarbazine (DTIC), doxorubin, cyclophosphamide or vincristine, or any combination of these. For example, DTIC and cylcophosphamide may be administered sequentially or concurrently with a naked Class III anti-CEA antibody or fragment thereof. Preferably, the anti-CEA antibody or fragment thereof is a humanized MN-14 antibody or fragment thereof. Similarly, 5-fluorouracil in combination with folinic acid, alone or in combination irinotecan (CPT-11) or in combination with oxaliplatin, is a regimen used to treat colorectal cancer. Other suitable combination chemotherapeutic regimens are well known, such as with oxaliplatin alone, or in combination with these other drugs, to those of skill in the art. Accordingly, combination therapy with any of these chemotherapeutic agents and a naked Class III anti-CEA antibody or fragment thereof can be used to treat MTC or non-MTC, depending on the regimen used. In medullary thyroid carcinoma, still other chemotherapeutic agents may be preferred, such as one of the alkylating agents (e.g., DTIC), as well as gemcitabine and other more recent classes of cytotoxic drugs. The chemotherapeutic drugs and a naked Class III anti-CEA antibody or fragment thereof, can be administered in any order, or together. In other words, the antibody and therapeutic agent may be administered concurrently or sequentially. In a preferred multimodal therapy, both chemotherapeutic drugs and naked Class III anti-CEA antibodies or fragments thereof are administered before, after, or co-administered with a conjugated or unconjugated anti-CEA antibody, fusion protein, or fragment thereof, according to the present invention. Preferably, the Class III anti-CEA antibody or fragment thereof is a humanized MN-14 antibody or fragment thereof.

A preferred treatment schedule of multimodal treatment is administering both hMN-14 and DTIC for 3 days, and administering only hMN-14 on days 7, 14, 21 and then every 21 days for a treatment duration of 12 months. The doses of hMN-14 are 0.5-15 mg/kg body weight per infusion, more preferably 2-8, and still more preferably 3-5 mg/kg per infusion, and the doses of DTIC are as currently applied at the preferred dose clinically, but could also be given at two-thirds or less of the maximum preferred dose in use, thereby decreasing drug-related adverse events. Repeated drug cycles can be given, such as every 1-6 months, with continuation of the naked antibody therapy, or with different schedules of radiolabeled antibody, drug-conjugated antibody, and inclusion of certain cytokines, such as G-CSF and/or GM-CSF, each dose adjusted so that toxicity to the patient is not enhanced by the therapeutic combination. The application of a cytokine growth factor, such as G-CSF, may enable even higher doses of myelosuppressive agents, such as radiolabeled antibody or cytotoxic drugs, to be administered, and these schedules and doses will be adjusted for the patients individually, depending on their disease status and prior therapy, all influence bone marrow status and tolerability to additional cytotoxic therapies. In a preferred embodiment, the MN-14 antibody or fragment thereof is administered in a dosage of 100-600 milligrams protein per dose per injection. Still preferred, the MN-14 antibody or fragment thereof is administered in a dosage of 300-400 milligrams of protein per dose per injection, with repeated doses preferred. The preferred antibody schedule is infusing once weekly or even less frequently, such as once every other week or even every third week, depending on a number of factors, including the extent of the disease and the amount of CEA circulating in the patient's blood.

Therapeutic Agents

The therapeutic agents recited here are those agents that also are useful for administration separately with a naked antibody, as described herein. Suitable therapeutic agents can be selected from the group consisting of a cytotoxic agent, a toxin, a hormone, a radionuclide, an immunomodulator, a photoactive therapeutic agent (such as a chromagen or dye), an antisense oligonucleotide, an immunoconjugate, another naked antibody, a hormone, or a combination thereof. Therapeutic agents include, for example, chemotherapeutic drugs such as vinca alkaloids and other alkaloids, anthracyclines, epidophyllotoxins, taxanes, antimetabolites, alkylating agents, antibiotics, COX-2 inhibitors, antimitotics, antiangiogenic and apoptotoic agents, particularly doxorubicin, methotrexate, taxol, CPT-11, camptothecans, and others from these and other classes of anticancer agents, and the like. Other useful cancer chemotherapeutic drugs for the preparation of immunoconjugates and antibody fusion proteins include nitrogen mustards, alkyl sulfonates, nitrosoureas, triazenes, oxaliplatin, folic acid analogs, COX-2 inhibitors, pyrimidine analogs, purine analogs, platinum coordination complexes, hormones, toxins (e.g., RNAse, Psudomonas exotoxin), and the like. Preferred therapeutic agents include DTIC, CPT-11, 5-fluorouracil, taxol, oxaliplatin, doxorubicin, cyclophosphamide and vincristine, or a combination thereof, depending on the malignancy to be treated. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

A toxin, such as *Pseudomonas* exotoxin, may also be administered with a naked Class III anti-CEA antibody or fragment thereof. Preferably, the Class III anti-CEA antibody or fragment thereof is a humanized MN-14 antibody or fragment thereof. Other suitable microbial, plant or animal toxins to be administered unconjugated to, but before, after, or simultaneously with the naked Class III anti-CEA antibody or fragment thereof include ricin, abrin, ribonuclease (RNase), DNase I, Staphylococcal enterotoxin-A, pokeweed antiviral protein, gelonin, diphtherin toxin, *Pseudomonas* exotoxin, and *Pseudomonas* endotoxin. See, for example, Pastan et al., *Cell* 47:641 (1986), and Goldenberg, *CA-A Cancer Journal for Clinicians* 44:43 (1994). Additional toxins suitable for use in the present invention are known to those of skill in the art and are disclosed in U.S. Pat. No. 6,077,499, which is incorporated in its entirety by reference. These can be derived, for example, from animal, plant and microbial sources, or chemically or recombinantly engineered. The toxin can be a plant, microbial, or animal toxin, or a synthetic variation thereof.

An immunomodulator, such as a cytokine may also be administered unconjugated to the chimeric, murine, humanized or human Class III anti-CEA antibody or fragment thereof of the present invention. As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor," erythropoietin and thrombopoietin. Examples of suitable immunomodulator moieties include IL-2, IL-6, IL-10, IL-12, IL-18, IL-21, interferon-γ, TNF-α, and the like. Therefore, subjects can receive a naked Class III anti-CEA antibody or fragment thereof and a separately administered cytokine, which can be administered before, concurrently or after administration of the naked Class III anti-CEA antibody or fragment thereof. Since some antigens may also be immunomodulators, CD40 antigen, for example, may also be administered in combination with a naked Class III anti-CEA antibody or fragment thereof either together, before or after the naked antibody or antibody combinations are administered. Additionally, radionuclides suitable for treating a diseased tissue include, but are not limited to, $^{32}$P, $^{33}$P, $^{47}$Sc, $^{59}$Fe, $^{64}$Cu, $^{67}$Cu, $^{75}$Se, $^{77}$As, $^{89}$Sr, $^{90}$Y, $^{99}$Mo, $^{105}$Rh, $^{109}$Pd, $^{111}$Ag, $^{125}$I, $^{131}$I, $^{142}$Pr, $^{143}$Pr, $^{149}$Pm, $^{153}$Sm, $^{161}$Tb, $^{166}$Ho, $^{169}$Er, $^{177}$Lu, $^{186}$Re, $^{188}$Re, $^{189}$Re, $^{194}$Ir, $^{198}$Au, $^{199}$Au, $^{211}$Pb, $^{212}$Pb, and $^{213}$Bi, $^{58}$Co, $^{67}$Ga, $^{80m}$Br, $^{99m}$Tc, $^{103m}$Rh, $^{109}$Pt, $^{111}$In, $^{119}$Sb, $^{161}$Ho, $^{189m}$Os, $^{192}$Ir, $^{152}$Dy, $^{211}$At, $^{212}$Bi, $^{223}$Ra, $^{219}$Rn, $^{215}$Po, $^{211}$Bi, $^{225}$Ac, $^{221}$Fr, $^{217}$At, $^{213}$Bi, $^{88}$Y and $^{225}$Fm. Preferred radionuclides are $^{125}$I, $^{131}$I, $^{90}$Y, $^{177}$Lu, and $^{225}$Ac. Also preferred, the radionuclide has an energy between 20 and 10,000 keV.

Pharmaceutically Acceptable Vehicles

The naked murine, humanized, chimeric and human Class III anti-CEA MAbs to be delivered to a subject can comprise one or more pharmaceutically acceptable vehicles, one or more additional ingredients, or some combination of these.

The unconjugated Class III anti-CEA antibodies and fragments thereof of the present invention can be formulated according to known methods to prepare pharmaceutically useful compositions. Preferably, the Class III anti-CEA antibody or fragment thereof is a MN-14 antibody or fragment thereof. Sterile phosphate-buffered saline is one example of a pharmaceutically acceptable vehicle. Other acceptable vehicles are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The unconjugated Class III anti-CEA antibody or fragment thereof of the present invention can be formulated for intravenous administration via, for example, bolus injection or continuous infusion. Preferably, the Class III anti-CEA antibody or fragments is a MN-14 antibody or fragment thereof. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the agent and naked antibody or fragment thereof. Control release preparations can be prepared through the use of polymers to complex or adsorb the naked antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10:1446 (1992). The rate of release of an antibody or fragment thereof from such a matrix depends upon the molecular weight of the immunoconjugate or antibody, the amount of antibody within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The unconjugated Class III anti-CEA antibody or fragment thereof may also be administered to a mammal subcutaneously or even by other parenteral routes. Moreover, the administration may be by continuous infusion or by single or multiple boluses. In general, the dosage of an administered naked antibody or fragment thereof for humans will vary depending upon such factors as the patient's age, weight, height, sex, general medical condition and previous medical history. Typically, it is desirable to provide the recipient with a dosage of naked antibody or fragment thereof that is in the range of from about 0.5 mg/kg to 20 mg/kg as a single intravenous infusion, although a lower or higher dosage also may be administered as circumstances dictate. This dosage may be repeated as needed, for example, once per month for 4-10 months, preferably once per every other week for 16 weeks, and more preferably, once per week for 8 weeks. It may also be given less frequently, such as every other week for several months or given more frequently and/or over a longer duration. The dosage may be given through various parenteral routes, with appropriate adjustment of the dose and schedule.

For purposes of therapy, the Class III anti-CEA antibody or fragment thereof is administered to a mammal in a therapeutically effective amount to reduce the size of the tumor as compared to untreated controls. Preferably, the Class III anti-CEA antibody or fragment thereof is a humanized MN-14 antibody or fragment thereof. A suitable subject for the present invention is usually a human, although a non-human mammal or animal subject is also contemplated. An antibody preparation is said to be administered in a "therapeutically effective amount" if the amount administered is physiologically significant. An agent is physiologically significant if its presence results in a detectable change in the physiology of a recipient mammal. In particular, an antibody preparation of the present invention is physiologically significant if its presence invokes an antitumor response. A physiologically significant effect could also be the evocation of a humoral and/or cellular immune response in the recipient mammal.

The present invention further includes the following numbered embodiments:

A composition comprising at least one anti-CEA monoclonal antibody (MAb) or fragment thereof and at least one therapeutic agent. The composition of embodiment 1, wherein said anti-CEA MAb is a Class I, Class II or Class III anti-CEA MAb, and when said MAb is a Class I or Class II MAb and is reactive with granulocytes, said MAb is a monovalent form of the MAb.

2. The composition of embodiment 1, wherein said anti-CEA MAb or fragment thereof is humanized, wherein said humanized MAb retains substantially the anti-CEA binding specificity of a murine anti-CEA MAb.

3. The composition of embodiment 1, wherein said anti-CEA MAb or fragment thereof is a chimeric MAb, and wherein said chimeric MAb retains substantially the anti-CEA binding specificity of murine anti-CEA MAb.

4. The composition of embodiment 1, wherein said anti-CEA MAb or fragment thereof is a fully human MAb, and wherein said fully human MAb retains substantially the anti-CEA binding specificity of murine anti-CEA MAb.

5. The composition of embodiment 1, wherein said anti-CEA monoclonal antibody or fragment thereof is a MN-14 antibody or fragment thereof.

6. The composition of embodiment 5, wherein said MN-14 monoclonal antibody or fragment thereof comprises the complementarity-determining regions (CDRs) of a murine MN-14 monoclonal antibody, wherein the CDRs of the light chain variable region of said MN-14 antibody comprises CDR1 comprising the amino acid sequence KASQD-VGTSVA (SEQ ID NO: 20); CDR2 comprising the amino acid sequence WTSTRHT (SEQ ID NO: 21); and CDR3 comprising the amino acid sequence QQYSLYRS (SEQ ID NO: 22); and the CDRs of the heavy chain variable region of said anti-CEA antibody comprises CDR1 comprising TYWMS (SEQ ID NO: 23); CDR2 comprising EIHPDSSTI-NYAPSLKD (SEQ ID NO: 24); and CDR3 comprising LYF-GFPWFAY (SEQ ID NO: 25).

7. The composition of embodiment 1, wherein said anti-CEA monoclonal antibody reacts with CEA and is unreactive with normal cross-reactive antigen (NCA) and meconium antigen (MA).

8. The composition of embodiment 7, wherein said MN-14 monoclonal antibody or fragment thereof is a humanized MN-14 antibody or fragment thereof.

9. The composition of embodiment 7, wherein said MN-14 monoclonal antibody or fragment thereof is a chimeric MN-14 antibody or fragment thereof.

10. The composition of embodiment 7, wherein said MN-14 monoclonal antibody or fragment thereof is a fully human MN-14 antibody or fragment thereof.

11. The composition of embodiment 8, wherein the framework regions (FRs) of the light and heavy chain variable regions of said humanized MN-14 antibody or fragment thereof comprise at least one amino acid substituted from the corresponding FRs of a murine MN-14 monoclonal antibody.

12. The composition of embodiment 11, wherein said humanized MN-14 antibody or fragment thereof comprises at least one amino acid from said corresponding FR of said murine MN-14 antibody is selected from the group consisting of amino acid residue 24, 28, 30, 48, 49, 74 and 94 of the murine heavy chain variable region (KLHuVhAIGA) of FIG. 14A-C or FIG. 22B (hMn-14) or FIG. 23B.

13. The composition of embodiment 11, wherein said humanized MN-14 antibody or fragment thereof comprises at least one amino acid from said corresponding FR of said murine MN-14 light chain variable region.

14. The composition of embodiment 8, wherein said humanized MN-14 antibody or fragment thereof comprises the light chain variable region as set forth in FIG. 13A or FIG. 22A or FIG. 23A, and the heavy chain variable region set forth in FIG. 14A-C designated as KLHuVhAIGA or FIG. 22B (hMN-14) or FIG. 23B.

15. The composition of embodiment 9, wherein said chimeric MN-14 antibody or fragment thereof comprises the light chain variable region as set forth in FIG. 13A designated as murine MN-14 VK and the heavy chain variable region set forth in FIG. 14A-C designated as murine MN-14 VH.

16. The composition of any of embodiments 1-15, wherein said fragment is selected from the group consisting of F(ab')₂, Fab', Fab, Fv and scFv.

17. The composition of any of embodiments 1-15, wherein said therapeutic agent is selected from the group consisting of a naked antibody, a cytotoxic agent, a drug, a radionuclide, an immunomodulator, a photoactive therapeutic agent, an immunoconjugate, a hormone, a toxin, an antisense oligonucleotide, or a combination thereof, optionally formulated in a pharmaceutically acceptable vehicle.

18. The composition of embodiment 17, wherein said combination thereof comprises vincristine, doxorubicin, oxaliplatin, CPT-11, fluorouracil, DTIC and cyclophosphamide.

19. The composition of embodiment 17, wherein said therapeutic agent is a naked antibody or an immunoconjugate.

20. The composition of embodiment 19, wherein said naked antibody or an antibody portion of said immunoconjugate comprises a humanized, chimeric, human or murine monoclonal antibody or fragment thereof selected from the group consisting of a monoclonal antibody or fragment thereof reactive with EGP-1, EGP-2 (e.g., 17-1A), MUC-1, MUC-2, MUC-3, MUC-4, PAM-4, KC4, TAG-72, EGFR, HER2/neu, BrE3, Le-Y, A3, A33, Ep-CAM, AFP, Tn, Thomson-Friedenreich antigens, tumor necrosis antigens, VEGF, P1GF, or other tumor angiogenesis antigens, Ga 733, IL-6, insulin-like growth factor-1, tenascin, fibronectin or a combination thereof.

21. The composition of embodiment 20, wherein said fragment is selected from the group consisting of F(ab)₂, F(abe)₂, Fab', Fab, Fv and scFv.

22. The composition of any of embodiments 1-15, wherein said therapeutic agent is not DTIC.

23. A method for treating non-medullary thyroid carcinoma comprising administering to a subject, either concurrently or sequentially, a therapeutically effective amount of an anti-CEA antibody or fragment thereof and at least one therapeutic agent, and optionally formulated in a pharmaceutically acceptable vehicle.

24. The method of embodiment 23, wherein said anti-CEA MAb or fragment thereof is humanized, wherein said humanized MAb retains substantially the anti-CEA binding specificity of a murine anti-CEA MAb.

25. The method of embodiment 23, wherein said anti-CEA MAb or fragment thereof is a chimeric MAb, and wherein said chimeric MAb retains substantially the anti-CEA binding specificity of murine anti-CEA MAb.

26. The method of embodiment 23, wherein said anti-CEA monoclonal antibody or fragment thereof is a MN-14 antibody or fragment thereof.

27. The method of embodiment 23, wherein said MN-14 monoclonal antibody or fragment thereof comprises the complementarity-determining regions (CDRs) of a murine MN-14 monoclonal antibody, wherein the CDRs of the light chain variable region of said MN-14 antibody comprises CDR1 comprising the amino acid sequence KASQD-VGTSVA (SEQ ID NO: 20); CDR2 comprising the amino acid sequence WTSTRHT (SEQ ID NO: 21); and CDR3 comprising the amino acid sequence QQYSLYRS (SEQ ID NO: 22); and the CDRs of the heavy chain variable region of said anti-CEA antibody comprises CDR1 comprising TYWMS (SEQ ID NO: 23); CDR2 comprising EIHPDSSTI-NYAPSLKD (SEQ ID NO: 24); and CDR3 comprising LYF-GFPWFAY (SEQ ID NO: 25).

28. The method of embodiment 27, wherein said MN-14 monoclonal antibody reacts with CEA and is unreactive with normal cross-reactive antigen (NCA) and meconium antigen (MA).

29. The method of embodiments 28, wherein said MN-14 monoclonal antibody or fragment thereof is a humanized MN-14 antibody or fragment thereof.

30. The method of embodiments 28, wherein said MN-14 monoclonal antibody or fragment thereof is a chimeric MN-14 antibody or fragment thereof.

31. The method of embodiments 28, wherein said MN-14 monoclonal antibody or fragment thereof is a fully human MN-14 antibody or fragment thereof.

32. The method of embodiment 29, wherein the framework regions (FRs) of the light and heavy chain variable regions of said humanized MN-14 antibody or fragment thereof comprise at least one amino acid substituted from the corresponding FRs of a murine MN-14 monoclonal antibody.

33. The method of embodiment 32, wherein said humanized MN-14 antibody or fragment thereof comprising at least one amino acid from said corresponding FR of said murine MN-14 antibody is selected from the group consisting of amino acid residue 24, 28, 30, 48, 49, 74 and 94 of the murine heavy chain variable region of FIG. 14A-C designated as KLHuVhAIGA or FIG. 22B (hMN-14) or FIG. 23B.

34. The method of embodiment 32, wherein said humanized MN-14 antibody or fragment thereof comprising at least one amino acid from said corresponding FR of said murine MN-14 light chain variable region.

35. The method of embodiment 32, wherein said humanized MN-14 antibody or fragment thereof comprises the light chain variable region as set forth in FIG. 13A or FIG. 22A (hMN-14) or FIG. 23A and the heavy chain variable region set forth in FIG. 14A-C designated as KLHuVhAIGA or FIG. 22B (hMN-14) or FIG. 23B.

36. The method of any of embodiments 23-35, wherein said fragment is selected from the group consisting of F(ab)$_2$, F(ab')$_2$, Fab', Fab, Fv and sFv.

37. The method of any of embodiments 23-35, wherein said therapeutic agent is selected from the group consisting of humanized, chimeric, human or murine monoclonal antibody or fragment thereof selected from the group consisting of a Class I anti-CEA monoclonal antibody, Class II anti-CEA monoclonal antibody, Class III anti-CEA monoclonal antibody, and a fragment thereof, and is administered either concurrently or sequentially in a therapeutically effective amount.

38. The method of embodiment 37, wherein said antibody or fragment thereof is either naked or conjugated to another therapeutic agent.

39. The method of any of embodiments 23-35, wherein said therapeutic agent is selected from the group consisting of a naked antibody, cytotoxic agent, a drug, a radionuclide, an immunomodulator, a photoactive therapeutic agent, an antisense oligonucleotide, an immunoconjugate of a CEA or non-CEA antibody, a hormone, or a combination thereof, optionally formulated in a pharmaceutically acceptable vehicle.

40. The method of embodiment 39, wherein said therapeutic agent is selected from the group consisting of a humanized, chimeric, human or murine monoclonal antibody or fragment thereof reactive with EGP-1, EGP-2 (e.g., 17-1A), IL-6, MUC-1, MUC-2, MUC-3, MUC-4, PAM-4, KC4, TAG-72, EGFR, EGP-2, HER2/neu, BrE3, Le-Y, A3, A33, Ep-CAM, AFP, Tn, Thomson-Friedenreich antigens, tumor necrosis antigens, VEGF, P1GF or other tumor angiogenesis antigens, Ga 733, IL-6, insulin-like growth factor-1, and a combination thereof, and is administered to said subject either concurrently or sequentially in a therapeutically effective amount.

41. The method of embodiment 40, wherein said antibody or fragment thereof is either naked or conjugated to another therapeutic agent.

42. The method of any of embodiments 23-35, wherein said therapeutic agent is not DTIC.

43. The method of embodiment 39, wherein said cytotoxic agent is a drug or a toxin.

44. The method of embodiment 43, wherein said drug possesses the pharmaceutical property selected from the group consisting of antimitotic, alkylating, antimetabolite, antiangiogenic, apoptotic, alkaloid, COX-2, and antibiotic agents and combinations thereof.

45. The method of embodiment 43, wherein said drug is selected from the group consisting of nitrogen mustards, ethylenimine derivatives, alkyl sulfonates, nitrosoureas, triazenes, folic acid analogs, anthracyclines, taxanes, COX-2 inhibitors, pyrimidine analogs, purine analogs, antimetabolites, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, doxorubicins and their analogs, and a combination thereof.

46. The method of embodiment 43, wherein said toxin is a microbial, plant or animal toxin selected from the group consisting of ricin, abrin, alpha toxin, saporin, ribonuclease (RNase), DNase I, Staphylococcal enterotoxin-A, pokeweed antiviral protein, gelonin, diphtherin toxin, *Pseudomonas* exotoxin, and *Pseudomonas* endotoxin.

47. The method of embodiment 39, wherein said immunomodulator is selected from the group consisting of a cytokine, a stem cell growth factor, a lymphotoxin, a hematopoietic factor, a colony stimulating factor (CSF), an interferon (IFN), a stem cell growth factor, erythropoietin, thrombopoietin and a combination thereof.

48. The method of embodiment 47, wherein said lymphotoxin is tumor necrosis factor (TNF), said hematopoietic factor is an interleukin (IL), said colony stimulating factor is granulocyte-colony stimulating factor (G-CSF) or granulocyte macrophage-colony stimulating factor (GM-CSF)), said interferon is interferons-α, -β or -γ, and said stem cell growth factor is designated "S1 factor".

49. The method of embodiment 47, wherein said immunomodulator comprises IL-1, IL-2, IL-3, IL-6, IL-10, IL-12, IL-18, IL-21, interferon-γ, TNF-α or a combination thereof.

50. The method of embodiment 39, wherein said radionuclide has an energy between 20 and 10,000 keV.

51. The method of embodiment 50, wherein said radionuclide is selected from the group consisting of $^{125}$I, $^{131}$I, $^{90}$Y, $^{88}$Y, $^{225}$Ac, $^{177}$Lu, $^{188}$Re, $^{186}$R, and combinations thereof.

52. The method of embodiment 39, wherein said photoactive therapeutic agent is a chromogen or dye.

53. The method of embodiment 44, wherein said alkylating agent is dacarbazine.

54. The method of embodiment 53, wherein said MN-14 antibody or fragment thereof is administered in a dosage of 100 to 600 milligrams protein per dose per injection.

55. The method of embodiment 54, wherein said MN-14 antibody or fragment thereof is administered in a dosage of 300-400 milligrams protein per dose per injection.

56. A method for treating medullary thyroid carcinoma comprising administering to a subject, either concurrently or sequentially, a therapeutically effective amount of an anti-CEA monoclonal antibody or fragment thereof and at least one therapeutic agent, and optionally formulated in a pharmaceutically acceptable vehicle.

57. The method of embodiment 56, wherein said anti-CEA MAb or fragment thereof is humanized, wherein said humanized MAb retains substantially the anti-CEA binding specificity of a murine anti-CEA MAb.

58. The method of embodiment 56, wherein said anti-CEA MAb or fragment thereof is a chimeric MAb, and wherein said chimeric MAb retains substantially the anti-CEA binding specificity of murine anti-CEA MAb.

59. The method of embodiment 56, wherein said anti-CEA monoclonal antibody or fragment thereof is a MN-14 antibody or fragment thereof.

60. The method of embodiment 59, wherein said MN-14 monoclonal antibody or fragment thereof comprises the complementarity-determining regions (CDRs) of a murine MN-14 monoclonal antibody, wherein the CDRs of the light chain variable region of said MN-14 antibody comprises CDR1 comprising the amino acid sequence KASQD-VGTSVA (SEQ ID NO: 20); CDR2 comprising the amino acid sequence WTSTRHT (SEQ ID NO: 21); and CDR3 comprising the amino acid sequence QQYSLYRS (SEQ ID NO: 22); and the CDRs of the heavy chain variable region of said Class III anti-CEA antibody comprises CDR1 comprising TYWMS (SEQ ID NO: 23); CDR2 comprising EIHP-DSSTINYAPSLKD (SEQ ID NO: 24); and CDR3 comprising LYFGFPWFAY (SEQ ID NO: 25).

61. The method of embodiment 60, wherein said MN-14 monoclonal antibody reacts with CEA and is unreactive with normal cross-reactive antigen (NCA) and meconium antigen (MA).

62. The method of embodiments 61, wherein said MN-14 monoclonal antibody or fragment thereof is a humanized MN-14 antibody or fragment thereof.

63. The method of embodiments 61, wherein said MN-14 monoclonal antibody or fragment thereof is a chimeric MN-14 antibody or fragment thereof.

64. The method of embodiments 61, wherein said MN-14 monoclonal antibody or fragment thereof is a fully human MN-14 antibody or fragment thereof.

65. The method of embodiment 62, wherein the framework regions (FRs) of the light and heavy chain variable regions of said humanized MN-14 antibody or fragment thereof comprise at least one amino acid substituted from the corresponding FRs of a murine MN-14 monoclonal antibody.

66. The method of embodiment 65, wherein said humanized MN-14 antibody or fragment thereof comprising at least one amino acid from said corresponding FR of said murine MN-14 antibody is selected from the group consisting of amino acid residue 24, 28, 30, 48, 49, 74 and 94 of the murine heavy chain variable region of FIG. 14A-C or 22B.

67. The method of embodiment 65, wherein said humanized MN-14 antibody or fragment thereof comprising at least one amino acid from said corresponding FR of said murine MN-14 light chain or heavy chain variable region.

68. The method of embodiment 65, wherein said humanized MN-14 antibody or fragment thereof comprises the light chain variable region as set forth in FIG. 13A or 22A (hMN-14) or 23A and the heavy chain variable region set forth in FIG. 14A-C or 22B (hMN-14) or 23B.

69. The method of any of embodiments 56-68, wherein said fragment is selected from the group consisting of F(ab)$_2$, F(ab')$_2$, Fab', Fab, Fv and sFv.

70. The method of any of embodiments 56-68, wherein said therapeutic agent is selected from the group consisting of humanized, chimeric, human or murine monoclonal antibody or fragment thereof selected from the group consisting of a Class I anti-CEA monoclonal antibody, Class II anti-CEA monoclonal antibody, Class III anti-CEA monoclonal antibody, and a fragment thereof, and is administered either concurrently or sequentially in a therapeutically effective amount.

71. The method of embodiment 70, wherein said antibody or fragment thereof is either naked or conjugated to another therapeutic agent.

72. The method of any of embodiments 56-68, wherein said therapeutic agent is selected from the group consisting of a naked antibody, cytotoxic agent, a drug, a toxin, a radionuclide, an immunomodulator, an antisense oligonucleotide, a photoactive therapeutic agent, an immunoconjugate of a CEA or non-CEA antibody, a hormone, or a combination thereof, optionally formulated in a pharmaceutically acceptable vehicle.

73. The method of embodiment 72, wherein said therapeutic agent is selected from the group consisting of a humanized, chimeric, human or murine monoclonal antibody or fragment thereof reactive with EGP-1, EGP-2 (e.g., 17-1A), MUC-1, MUC-2, MUC-3, MUC-4, PAM-4, KC4, TAG-72, EGFR, HER2/neu, BrE3, Le-Y, A3, A33, Ep-CAM, AFP, Tn, Thomson-Friedenreich antigens, tumor necrosis antigens, VEGF, P1GF or other tumor angiogenesis antigens, Ga 733, IL-6, insulin-like growth factor-1, and a combination thereof, and is administered to said subject either concurrently or sequentially in a therapeutically effective amount.

74. The method of embodiment 73, wherein said antibody or fragment thereof is either naked or conjugated to another therapeutic agent.

75. The method of any of embodiments 56-68, wherein said therapeutic agent is not DTIC.

76. The method of embodiment 72, wherein said cytotoxic agent is a drug or a toxin.

77. The method of embodiment 72, wherein said drug possesses the pharmaceutical property selected from the group consisting of antimitotic, alkylating, antimetabolite, antiangiogenic, apoptotic, alkaloid, COX-2, and antibiotic agents and combinations thereof.

78. The method of embodiment 76, wherein said drug is selected from the group consisting of nitrogen mustards, ethylenimine derivatives, alkyl sulfonates, nitrosoureas, triazenes, folic acid analogs, anthracyclines, taxanes, COX-2 inhibitors, pyrimidine analogs, purine analogs, antimetabolites, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, doxorubicins and their analogs, and a combination thereof.

79. The method of embodiment 76, wherein said microbial, plant or animal toxin is selected from the group consisting of ricin, abrin, alpha toxin, saporin, ribonuclease (RNase), DNase I, Staphylococcal enterotoxin-A, pokeweed antiviral protein, gelonin, diphtherin toxin, *Pseudomonas* exotoxin, and *Pseudomonas* endotoxin.

80. The method of embodiment 72, wherein said immunomodulator is selected from the group consisting of a cytokine, a stem cell growth factor, a lymphotoxin, a hematopoietic factor, a colony stimulating factor (CSF), an interferon (IFN), a stem cell growth factor, erythropoietin, thrombopoietin and a combination thereof.

81. The method of embodiment 80, wherein said lymphotoxin is tumor necrosis factor (TNF), said hematopoietic factor is an interleukin (IL), said colony stimulating factor is granulocyte-colony stimulating factor (G-CSF) or granulocyte macrophage-colony stimulating factor (GM-CSF)), said interferon is interferons-α, -β or -γ, and said stem cell growth factor is designated "S1 factor".

82. The method of embodiment 72, wherein said immunomodulator comprises IL-1, IL-2, IL-3, IL-6, IL-10, IL-12, IL-18, IL-21, interferon-γ, TNF-α or a combination thereof.

83. The method of embodiment 72, wherein said radionuclide has an energy between 20 and 10,000 keV.

84. The method of embodiment 83, wherein said radionuclide is selected from the group consisting of $^{125}I$, $^{131}I$, $^{90}Y$, $^{88}Y$, $^{225}Ac$, $^{177}Lu$, $^{188}Re$, $^{186}Re$, and combinations thereof.

85. The method of embodiment 72, wherein said photoactive therapeutic agent is a chromogen or dye.

86. The method of embodiment 77, wherein said alkylating agent is dacarbazine.

87. The method of embodiment 86, wherein said MN-14 antibody or fragment thereof is administered in a dosage of 100 to 600 milligrams protein per dose per injection.

88. The method of embodiment 87, wherein said MN-14 antibody or fragment thereof is administered in a dosage of 300-400 milligrams protein per dose per injection.

89. A method for treating cancer comprising administering to a subject, either concurrently or sequentially, a therapeutically effective amount of an anti-CEA antibody or fragment thereof and at least one therapeutic agent, and optionally formulated in a pharmaceutically acceptable vehicle.

90. The method of embodiment 89, wherein the therapeutic agent is CPT-11.

91. The method of embodiment 90, wherein the anti-CEA antibody or fragment is administered prior to administration of CPT-11.

92. The method of embodiment 91, wherein the anti-CEA antibody or fragment is administered around 3 days prior to administration of CPT-11.

93. The method of embodiment 89, wherein the therapeutic agent is DTIC.

94. The method of embodiment 89, wherein the therapeutic agent is oxaliplatin.

95. The method of embodiment 89, wherein the therapeutic agent is 5-fluorouracil/leucovorin.

96. In a method of treating cancer with a non-antibody therapeutic agent, the improvement comprising pre-treating a subject suffering from cancer with an anti-CEA antibody or a fragment thereof prior to administration of the non-antibody therapeutic agent.

97. The method of embodiment 96, wherein the anti-CEA antibody is hMN-14.

98. The method of embodiment 96, wherein the therapeutic agent is CPT-11.

99. A method of treating cancer with an antibody comprising administering to a subject suffering from cancer, prior to administration of the antibody, an agent that activates granulocytes and/or NK cells in order to increase effector function of the antibody.

100. The method of embodiment 99, wherein the agent is GM-CSF.

101. The method of embodiment 99, wherein the antibody is an anti-CEA antibody.

102. The method of embodiment 101, wherein the antibody is hMN-14.

103. A method of treating cancer with an anti-CEA antibody or fragment, comprising administering to a subject suffering from cancer, prior to administration of the anti-CEA antibody or fragment, an amount of interferon effective to up regulate CEA expression in tumor cells.

104. The method of embodiment 103, wherein the anti-CEA antibody is hMN-14.

105. An antibody fusion protein comprising at least one CEA binding site and at least one other binding site for the same or different antigen.

106. The antibody fusion protein according to embodiment 105, wherein the CEA binding site binds to the same site as an MN-14 antibody.

107. The antibody fusion protein according to embodiment 105, which is bivalent and trivalent.

108. The antibody fusion protein according to embodiment 105, wherein one arm of the fusion protein is a Class III, anti-CEA MAb that targets CD66e and another arm of the fusion protein is from another CEA crossreactive antibody that targets CD66a-d.

109. The antibody fusion protein according to embodiment 105, wherein the binding arms are scFv or Fab regions.

110. An antibody fusion protein according to embodiment 105, which is a bispecific, trivalent protein comprising one arm reactive with CD66a-d and two arms reactive with only CEA (CD66e).

111. An antibody fusion protein according to embodiment 105, which is a bispecific protein comprising two arms that bind to NCA50/90.

112. An antibody fusion protein according to embodiment 105, which is a diabody comprising one arm that binds to NCA50/90 and a second arm that binds to a Class III epitope of CEA.

113. An antibody fusion protein according to embodiment 112, wherein the NCA-50/90 arm is obtained from an hMN-3 antibody and the second arm that binds to a Class III epitope of CEA is obtained from hMN-14.

114. An antibody fusion protein according to embodiment 113, wherein the fusion protein lacks an Fc-domain to prevent activation of cytokine release from granulocytes or which has an Fc-domain that has been modified to prevent complement fixation and ADCC.

115. An antibody fusion protein according to embodiment 104, which is a triabody comprising one hMN-3 arm and two hMN14 arms. 115a. An antibody fusion protein according to embodiment 104, which is a triabody comprising one hMN-15 arm and two hMN14 arms.

116. An antibody fusion protein according to embodiment 104, comprising at least one hMN-14 arm and at least one NP-3 arm.

117. An antibody fusion protein according to embodiment 116, which comprises an Fc-domain to enable complement fixation and activation of ADCC.

118. An antibody fusion protein according to embodiment 104, further comprising a therapeutic agent.

119. An antibody fusion protein according to embodiment 118, wherein the therapeutic agent is a cytokine.

120. An antibody fusion protein according to embodiment 119, wherein the cytokine is interferon, a colony-stimulating factor, or an interleukin.

121. An antibody fusion protein according to embodiment 120, wherein the colony-stimulating factor is GM-CSF or G-CSF.

The invention is further illustrated by, though in no way limited to, the following examples.

EXAMPLE 1

Materials and Methods

Monoclonal Antibodies and Cell Lines

TT, a human medullary thyroid cell line, was purchased from the American Type Culture Collection. The cells were grown as monolayers in DMEM (Life Technologies, Gaithersburg, Md.) supplemented with 10% fetal bovine serum, penicillin (100 U/ml), streptomycin (100 µg/ml), and L-glutamine (2 mM). The cells were routinely passaged after detachment with trypsin, 0.2% EDTA.

MN-14 is a Class III anti-CEA MAb, reacting with CEA and unreactive with the normal cross reactive antigen, NCA, and meconium antigen (Hansen et al., *Cancer*, 71:3478 (1993)). The construction and characterization of the humanized forms of MN-14 and LL2, the anti-CD22 MAb used here as a negative control, have been previously described. (Sharkey et al., *Cancer Res.*, 55:5935s (1995); Leung et al., *Mol. Immunol.*, 32:1416 (1995)). P3x63Ag8 (MOPC-21) is an irrelevant mouse myeloma $IgG_1$ obtained from the American Type Culture collection (Rockville, Md.). The antibodies were purified by protein A chromatography.

In Vivo Studies

Tumors were propagated in female nu/nu mice (Taconic Farms, Germantown, N.Y.) at 6-8 weeks of age by s.c. injection of $2\times10^8$ washed TT cells, which had been propagated in tissue culture. Antibodies were injected i.v., via the lateral tail vein, into the tumor-bearing animals. Details on the quantities of antibodies injected and the time of administration are indicated in the Results section for each study. Results are given as tumor volumes of individual animals as well as the mean±SE. Tumor size was monitored by weekly measurements of the length, width, and depth of the tumor using a caliper. Tumor volume was calculated as the product of the three measurements. Statistical comparisons were made using the Student's T-test to compare tumor volumes and area under the growth curves.

EXAMPLE 2

Combination Therapy of Naked hMN-14 and DTIC Delivered 2 Days After Injection of TT (Human Medullary Thyroid) Tumor Cells In a previous study, naked hMN-14 and dacarbazine (DTIC) were given in combination to TT 2 days after tumor implantation, using 100 µg and 25 µg doses of DTIC (days 2, 3, and 4) and 250 µg doses of hMN-14 given on day 2, then weekly. The 100 µg DTIC dose combined with hMN-14 was more effective than either treatment alone (FIG. 1A). However, the 100 µg DTIC dose yielded too strong a response, while the 25 µg dose was not effective. Surprisingly, the effects of MN-14 alone and DTIC alone were not additive. In other words, given the results of treatment with 250 µg hMN-14 alone and 100 µg DTIC alone, one would not predict that the combination of 250 µg hMN-14 and 100 µg DTIC would have such a pronounced effect. See FIG. 1A.

In this study, treatment began 2 days after TT cell injection, as in the previous study. hMN-14 was given at 100 µg/dose on days 2, 3, 4, 5, 7, 8, 9, 10, 11, 15 and 22, then every 7 days until the animal died, the tumor attained a volume of 2.0 $cm^3$ or the study terminated for humane reasons. Doses of DTIC were 50 and 75 µg per dose, which is between the doses given in the previous study. TT cells were injected subcutaneously in 60 nude mice. The day of injection was Monday, day 0, See FIG. 1B.

Results demonstrate that significant delays in tumor growth were caused by either MAb therapy alone or chemotherapy alone (FIG. 1B). The 75 µg dose of DTIC in combination with this schedule of hMN-14 antibody was significantly more effective than either treatment alone (p<0.02). Unexpectedly, the results of combined DTIC and MAb therapy were not additive. At 7 weeks, 8/10 mice in the 75 µg DTIC and MAb group had no palpable tumor, compared to 1/10 mice in the 75 µg DTIC only group and 0/10 mice in the untreated and MAb group.

Mean tumor volumes at 7 weeks were 0.018±0.039 $cm^3$ (75 µg DTIC plus MN-14), 0.284+0.197 $cm^3$ (75 µg DTIC only), 0.899±0.545 $cm^3$ (hMN-14 only) and 1.578±0.959 $cm^3$ (untreated). Combined therapy of the naked anti-CEA antibody with DTIC augments the anti-tumor effects of antibody or chemotherapy alone, without increased toxicity. The superiority of the combined modality treatment was surprising.

Dosing Summary: (1) hMN-14 was given daily (i.p.), except Sundays, at 100 µg/dose/mouse on days 2 through 11. The antibody treatment was initiated on the same day as DTIC treatment. (2) DTIC was given on days 2, 3, and 4 at 50 and 75 µg/dose, which corresponded to 5% and 7.5% of the MTD. Only one course of DTIC was given.

Groups: 6 groups of mice, each group containing 10 mice.

Group 1: Untreated.

Group 2. DTIC at 50 µg/dose, days 2, 3, and 4 (Wednesday, Thursday, and Friday).

Group 3. DTIC at 75 µg/dose, days 2, 3, and 4.

Group 4. DTIC at 50 µg/dose, days 2, 3, and 4, plus hMN-14 (100 µg/dose) day 2, 3, 4, 5, 7, 8, 9, 10, 11, 15 and 22, then every 7 days until the animal died, the tumor attained a volume of 2.0 $cm^3$, or the study terminated.

Group 5. DTIC at 25 µg/dose, days 2, 3, and 4, plus hMN-14 (100 µg/dose) day 2, 3, 4, 5, 7, 8, 9, 10, 11, 15 and 22, then every 7 days until the animal died, the tumor attained a volume of 2.0 $cm^3$, or the study terminated.

Group 6. hMN-14 (confirm 100 µg/dose), days 2, 3, 4, 5, 7, 8, 9, 10, 11, 15 and 22, then every 7 days until the animal died, the tumor attained a volume of 2.0 $cm^3$, or the study terminated.

Animals were monitored for survival. Tumor and body weight were measured weekly.

Protocol: On day 2, 200 mg/vial DTIC was reconstituted with 19.7 ml sterile water for injection. The resulting solution contained 10 mg/ml of dacarbazine with a pH range of 3.0-4.0. The solution was used as needed for the dilutions described below and the remainder was frozen in 1 ml aliquots for subsequent use.

Groups 2 and 4: 5 ml of 0.5 mg/ml solution was prepared. 100 µl of 0.5 mg/ml/mouse was injected i.v.

Groups 3 and 5: 5 ml of 0.75 mg/ml solution was prepared. 100 µl of 0.75 mg/ml/mouse was injected i.v.

Quantity of hMN-14 was estimated. 100 µl of 1 mg/ml hMN-14 was injected i.p. in mice in Groups 4, 5 and 6.

EXAMPLE 3

Radioimmunotherapy Studies in a Human MTC Xenograft Model

Applicants developed a model for experimental radioimmunotherapy of MTC with radiolabeled anti-CEA MAbs using human MTC xenografts of the CEA- and calcitonin producing human MTC cell line designated TT ([Stein, 1999 #82], see Appendix). MTC tumors were established in nude mice by a s.c. inoculation of $2\times10^8$ cells and allowed to grow for 2-5 weeks before injection of MAbs. Biodistribution and RAIT studies were then carried out with MN-1 4, which was shown by flow cytometry to react with TT cells. Both Ag8 and Mu-9 were used as negative control MAbs in these studies. Preliminary studies using smaller tumors of ~0.08 g showed that 7 days after the injection of $^{131}$I-MN-14, the percent of injected dose per gram of tumor (% ID/g) was 68.9% compared with only 12.6% ID/g for the co-injected $^{125}$I-Ag8 control. Using larger tumors, (grown for five weeks in nude mice; mean tumor weight=0.404 g), the % ID/g of tumor observed at seven days post injection of $^{125}$I-MN-14 was 12.4%. However, the % ID/g of the co-injected $^{88}$Y-MN-14 was 50.5%, or 4.1-fold higher than $^{125}$I-MN-14. The tumor-to-blood, lungs, liver, spleen, and kidneys were also higher with $^{88}$Y-MN-14 than with $^{125}$I-MN-14, while the tumor-to-bone ratios were equal with both agents. When $^{125}$I-MN-14 and $^{88}$Y-MN-14 biodistribution data were used to predict the tumor dosimetry with $^{131}$I-MN-14 and $^{90}$Y-MN-14, respectively, the radiation absorbed dose delivered at the MTD of $^{90}$Y-MN-14 (115 µCi) was 1.75-fold higher than that delivered at the MTD of $^{131}$I-MN-14 (275 µCi) (4900 cGy vs. 2800 cGy).

Figure 2:
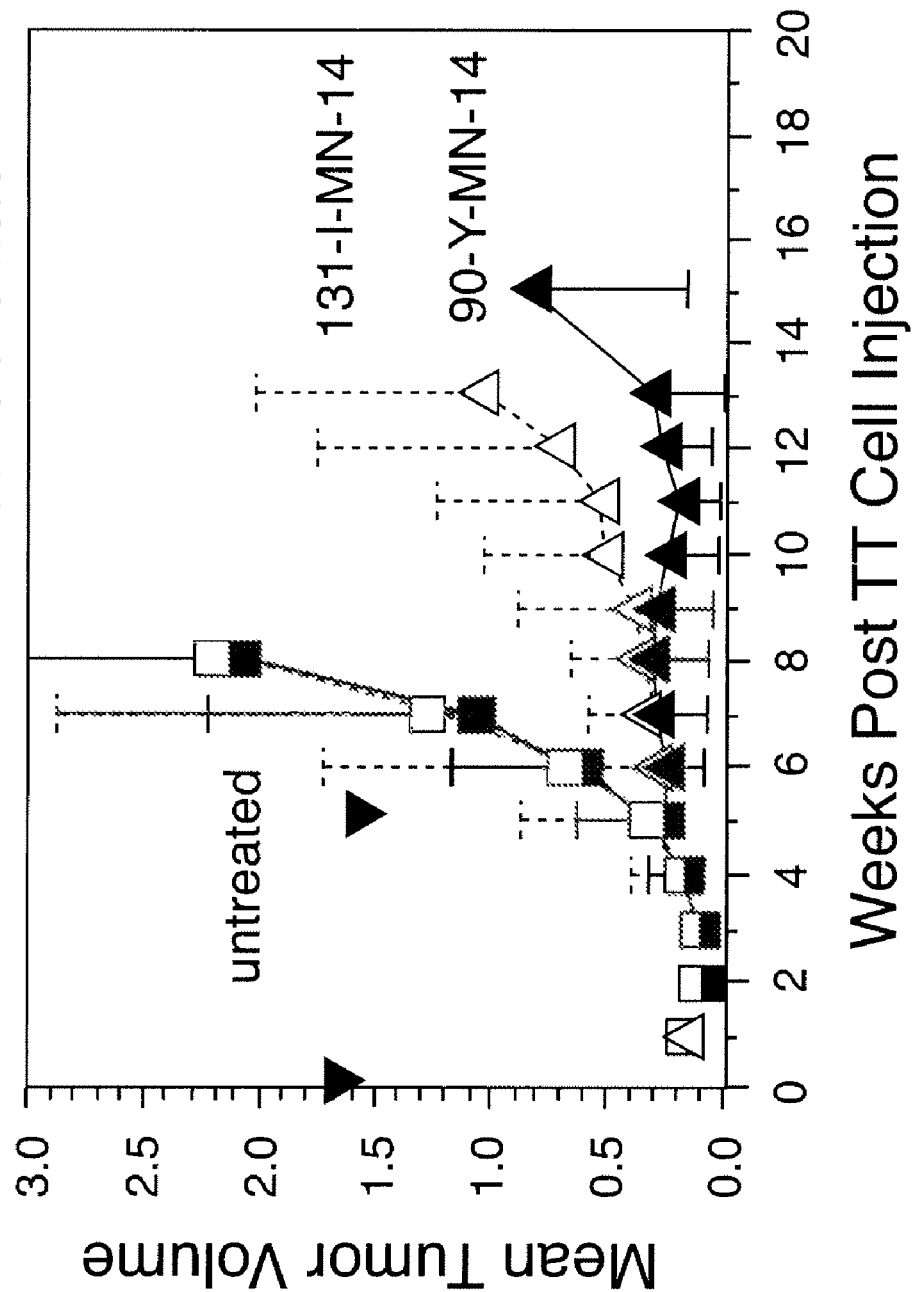
FIG. 2. Graph comparing tumor volume after radioimmunotherapy (RAIT) with $^{131}I$ and $^{90}Y$-MN-14.

Therapy studies in this model confirmed that $^{90}$Y-MN-14 is a better therapeutic agent than $^{131}$I-MN-14. In 5-week-old tumors, a 5-week complete inhibition of tumor growth was seen at the MTD of $^{90}$Y-MN 14 compared to only a tumor growth delay with $^{131}$I-MN-14 (FIG. 2). Moreover, when smaller 2-week old tumors were treated, an average of 60% tumor volume reduction, with some complete tumor regressions, was seen at the MTD of $^{90}$Y-MN-14. These anti-tumor effects were very significant compared with the relatively rapid tumor growth in untreated animals or those treated at the MTD of control MAbs. Thus, our preclinical studies demonstrated that this animal model is exquisitely suitable for experimental RAIT with anti-CEA MAbs.

The longer path length and higher energy of $^{90}$Y compared with $^{131}$I, in addition to the fact that $^{90}$Y is retained longer by target cells led to delivery of an increased radiation dose to tumor and thus more effective therapy at equitoxic doses. If our results with residualizing $^{131}$I (refs) can be generalized to MN-14 in MTC, we would expect that residualizing $^{131}$I would be at least equally effective to $^{90}$Y in tumors of the size studied here, and most likely superior in the setting of micrometastatic disease or as adjuvant therapy following surgery.

EXAMPLE 4

Chemotherapy

Figure 3:
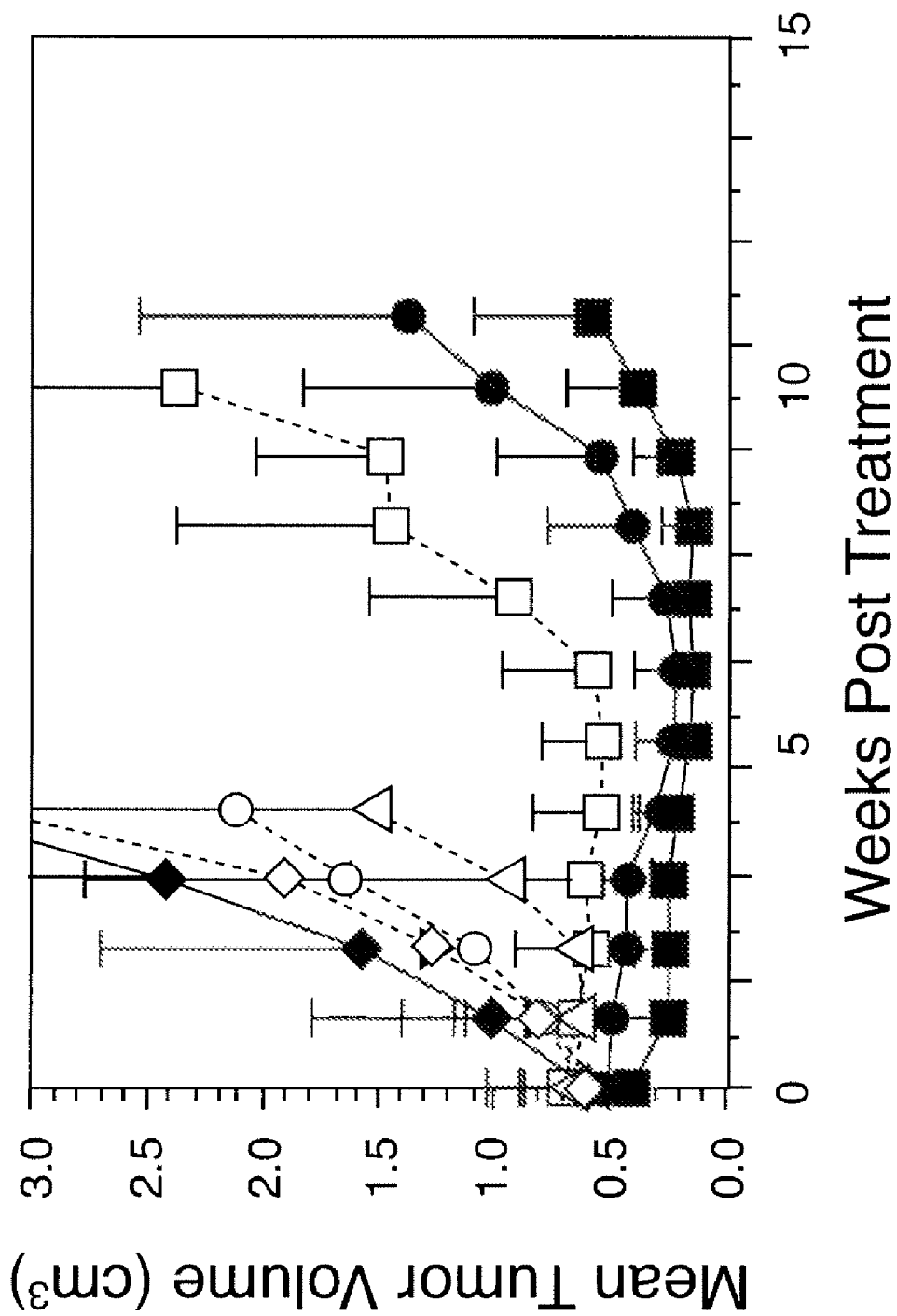
FIG. 3. Graph comparing the therapeutic efficacy of several chemotherapeutic drugs on tumor volume in TT bearing mice. TT bearing mice were given doxorubicin @ 20 mg/m$^2$; days 0, 1, and 2, (70 μg/dose) (O); DTIC @ 300 mg/m$^2$; days 0, 1, and 2, (1.08 mg/dose) (□); doxorubicin and DTIC as above (●); cyclophosphamide @ 600 mg/m$^2$; day 0 (2.16 mg/dose) (Δ); vincristine @ 4.2 μg/dose; day 0 (x); all 4 drugs (doxorubicin, DTIC, cyclophosphamide, and vincristine) at the doses described for each above (■); or left untreated (◆). Groups consisted of 6-9 nude mice bearing established TT tumors. Mean tumor volume at time of treatment was 0.51+/−0.33 cm$^3$. Points: mean tumor size. Error bars: std dev, and are shown only above the symbol for clarity.

Four drugs, doxorubicin, DTIC (dacarbazine), cyclophosphamide, and vincristine, were evaluated, singly and in combination, for their effect on the growth of TT MTC xenografts in nude mice. Doses were selected based on the doses of each drug given clinically to humans on a mg/m$^2$ basis. Animals were monitored for survival, and tumor volumes and body weights were measured weekly. FIG. 3 shows the tumor growth curve for animals in this study. Given individually, doxorubicin, DTIC and cyclophosphamide, but not vincristine, yielded significant growth inhibition, although the growth delay caused by DTIC was markedly longer than that of the other drugs. Approximate mean time to doubling for each group was: untreated, 1 week; doxorubicin, 2.5 weeks; DTIC, 7.5 weeks; cyclophosphamide, 3 weeks; and vincristine, 1.5 weeks. Combining doxorubicin and DTIC improved the efficacy compared to either drug alone, increasing the mean time to doubling to 10 weeks. However, the increased efficacy of doxorubicin and DTIC combination did not reach the 95% confidence level in comparison to DTIC alone. The P values for AUC comparisons were as follows: P<0.01 for doxorubicin+DTIC versus doxorubicin, and P<0.1 for doxorubicin+DTIC versus DTIC. The 4-drug regimen extended the mean time to doubling to 12 weeks; P<0.01 for comparisons to both doxorubicin and DTIC.

Log rank analysis of survival data for the individual drugs versus the untreated group indicated a significant difference only for DTIC and cyclophosphamide. Mean survival time for the untreated control group was 4 weeks compared to 11 weeks and 8 weeks for DTIC and cyclophosphamide treatment groups, respectively, and greater than 12 weeks for the drug combinations. Toxicity, as measured by body weight loss, was within the acceptable range for all study groups. Maximum weight loss was observed 1 week after treatment in the mice treated with all 4 drugs, ranging from 3-12% loss of body weight.

EXAMPLE 5

Combining Radioimmunotherapy and Chemotherapy for Treatment of MTC

RAIT Plus 4-Drug Combination.

Figure 4:
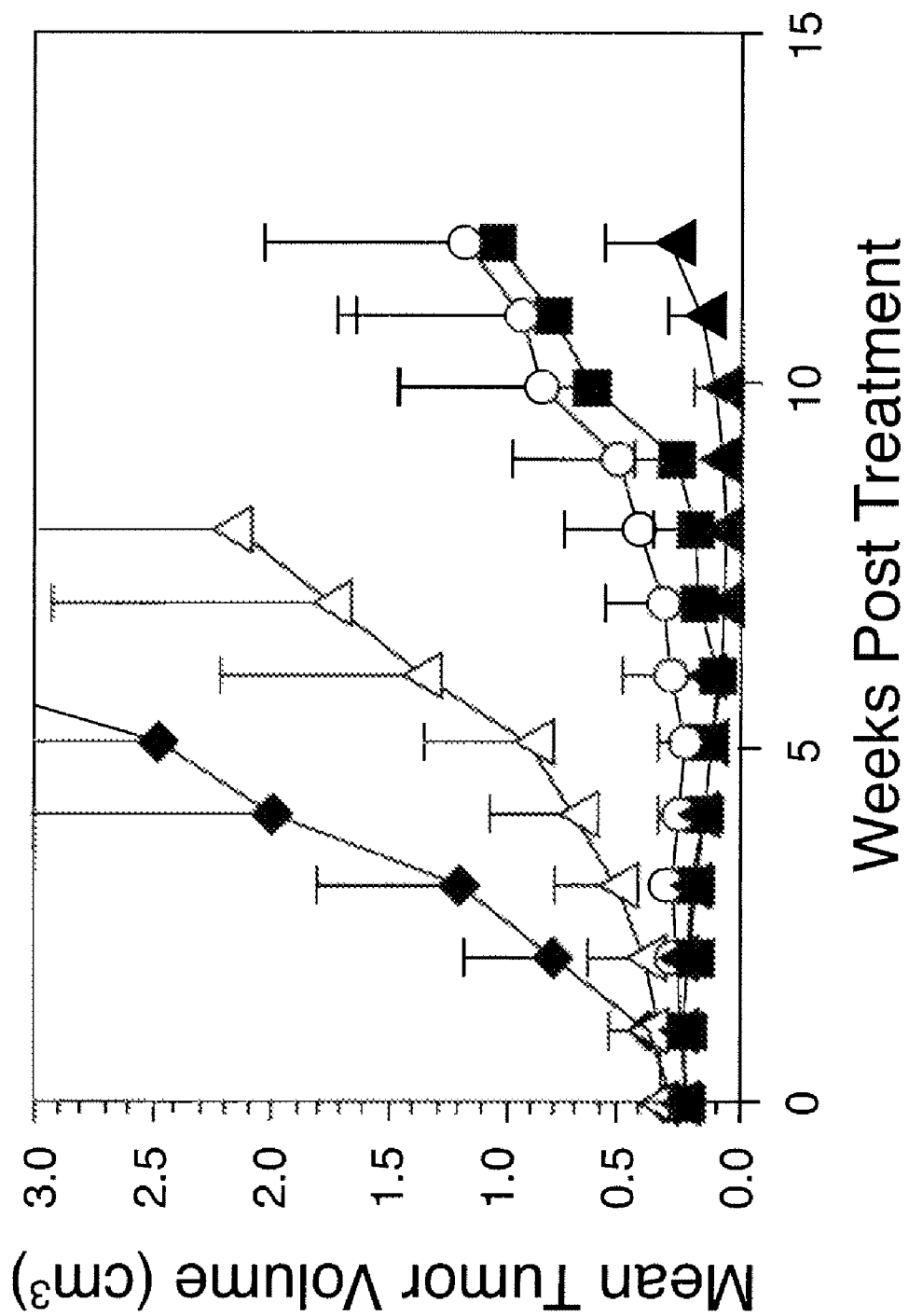
FIG. 4. Graph comparing the therapeutic efficacy of combination therapy of RAIT with $^{90}Y$-labeled anti CEA MAb MN-14 and a 4-drug combination initiated 24 hours after RAIT on tumor volume in mice. Tumor bearing animals were either left untreated (◆); given the 4-drug regimen described in FIG. 1, administered on days 1, 2, and 3 (■); 52.5 μCi $^{90}Y$-MN-14 day on 0, followed by the 4-drug regimen administered on days 1, 2, and 3 (▲); 52.5 μCi $^{90}Y$-MN-14 on day 0 (Δ); or 105 μCi $^{90}Y$-MN-14 on day 0 (O). N=5 for the untreated group, and n=9-10 in the treatment groups. Mean tumor volume at time of treatment was 0.28+/−0.12 cm$^3$. Points: mean tumor size. Error bars: std dev, and are shown only above the symbol for clarity.

The effect of combining RAIT with $^{90}$Y-anti CEA MAb MN-14 and the 4-drug combination was evaluated by comparing the growth of TT in untreated mice to those treated with the 4-drug regimen described above (doxorubicin, DTIC, cyclophosphamide, and vincristine), 100% of the maximum tolerated dose (MTD) of RAIT (105 µCi), 50% of the MTD of RAIT, and 50% of the MTD of RAIT combined with the 4 drugs. FIG. 4 shows the growth curves of TT tumors in mice given the various treatment regimens. All four of the treatment groups yielded significant improvement in efficacy compared to the untreated animals. Whereas the approximate mean time to doubling in the untreated animals was 1.5 weeks, chemotherapy with the 4 drugs extended the mean doubling time to 10 weeks and RAIT alone yielded 4-week and 8-week doubling times at 50% and 100% of the MTD, respectively. As expected, both the 100% RAIT group and the 4-drug therapy regimen were significantly better than the 50% RAIT group. Most importantly, combining 50% RAIT and the 4-drug regimen yielded improved results, compared to either therapy alone, further extending the mean doubling time to approximately 12.5 weeks. For the comparison of the combined treatment to the 4-drug regimen, P<0.02, and for the comparison to 100% RA11, P<0.01.

Mean weight loss 1 week post treatment (nadir) was 9% for the 100% RAIT and the 4-drug regimens, but 15% for combined 50% RAIT plus 4-drug treatment. In addition, in the combined therapy group, one animal died three weeks post treatment and a second animal had a weight loss greater than 20%. Thus, this treatment exceeded the maximum tolerated dose.

RAIT Plus Chemotherapy with 2-Drug Regimens.

The effect of combining RAIT with $^{90}$Y-anti CEA MAb MN-14 and chemotherapy with a 2-drug combination, consisting of doxorubicin and DTIC, was also evaluated in this MTC xenograft model. Approximate doubling times for the groups were: untreated, 1.5 weeks; doxorubicin plus DTIC, 8 weeks; the MTD of RAIT, 10 weeks; and the MTD of RAIT combined with 25-75% of the 2-drug regimen, greater than 12 weeks. Thus, RAIT alone was more effective than the 2-drug regimen and, most significantly, combining RAIT and the 2-drug regimen yielded improved results compared to either therapy alone. For the comparison of the combined treatment to the 2-drug regimen, P<0.005, for the comparison to RAIT alone, P<0.02.

Mean weight loss 1-2 weeks post treatment (nadir) was 2-8% for all groups, except the 100% RAIT plus 75% 2-drug chemotherapy group, where a 13% loss was observed at 2 weeks. In addition, in this combined therapy group, two animals died 3-4 weeks post treatment and one experienced a weight loss greater than 20%. Thus, addition of the 75% dose level of doxorubicin and DTIC to 100% RAIT treatment exceeded the MTD, whereas 50% of this 2-drug combination can be tolerated in combination with 100% RAIT.

RAIT Plus Doxorubicin.

Because previous publications have reported the combination of RAIT with doxorubicin in this model (Stein et al., *Clin Cancer Res.*, 5:3199s (1999); Behr et al., *Cancer Res.*

57:5309 (1997)), a direct comparison was made to the RAIT plus doxorubicin regimen. A direct comparison was also made to RAIT plus the 4-drug regimen. All treatments yielded significant efficacy compared to the untreated animals. The mean doubling time for the RAIT plus doxorubicin group was 12 weeks. In this study combining the full MTD of RAIT with either 50% of doxorubicin and DTIC or the 4-drug regimen extended the mean doubling time to greater than 15 weeks, with no statistically significant difference between these two groups. A substantial number of objective responses were observed in these studies. Following treatment with RAIT plus doxorubicin there were 3 complete responses, 2 partial responses, and 5 animals with stable disease for at least 4 weeks, out of a total of 10 mice. The RAIT plus 2-drug protocol increased the objective responses to 10 complete responses and 2 partial responses of 12 animals, and the RAIT plus 4-drug treatment protocol led to 7 complete responses and 2 partial responses out of 9 mice.

RAIT Plus DTIC.

Figure 5:
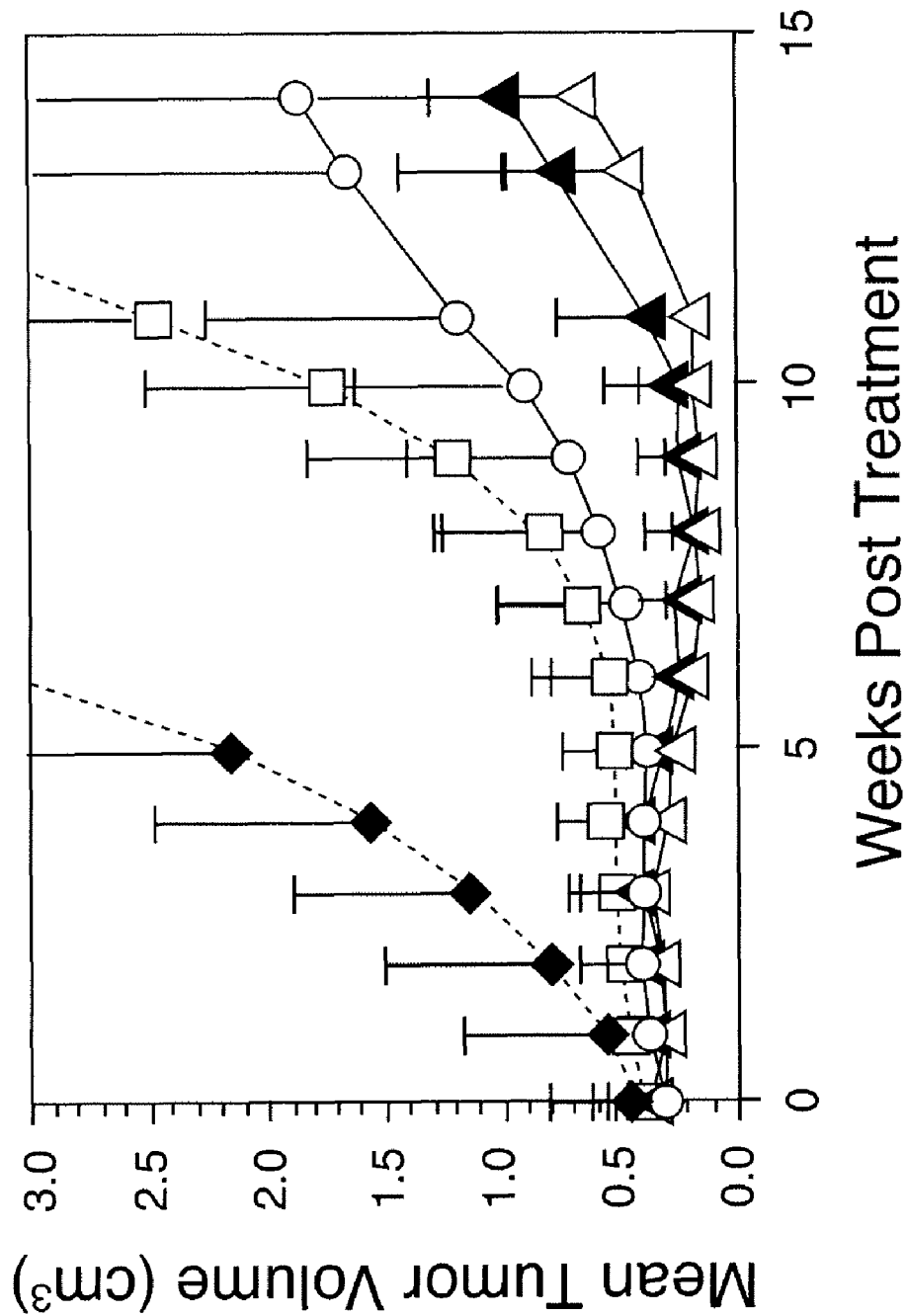
FIG. 5. Graph comparing the efficacy of RAIT plus DTIC and RAIT plus doxorubicin and DTIC in TT bearing mice. TT bearing mice were either left untreated (◆); given 105 μCi $^{90}Y$-MN-14 on day 0 (O); 105 μCi $^{90}Y$-MN-14 on day 0, followed by the doxorubicin and DTIC regimen administered at 50% the full dosage on days 1, 2, and 3 (▲); 105 μCi $^{90}Y$-MN-14 day on 0, followed by DTIC at 75% of the full dosage on days 1, 2, and 3 (x); or the full dosage of DTIC, 300 mg/m$^2$ on days 1, 2, and 3, (1.08 mg/dose) (□). N=5 for the untreated group, and n=8-9 in the treatment groups. Mean tumor volume at time of treatment was 0.39+/−0.20 cm$^3$. Points: mean tumor size. Error bars: std dev, and are shown only above the symbol for clarity.

Because DTIC was the most effective chemotherapeutic agent when administered alone, the efficacy of RAIT plus DTIC was evaluated in comparison to that of RAIT plus doxorubicin and DTIC. Omitting doxorubicin from the treatment protocol will be important for clinical application in order to avoid the added toxicity of this drug, especially the known cardiac toxicity. As shown in FIG. 5, the two study groups which received the chemotherapy in combination with RAIT, either doxorubicin and DTIC or DTIC only, are approximately equal to each other, and both are more effective than the single modality treatments. P values for AUC comparisons were as follows: P<0.01 for RAIT+DTIC versus DTIC, and P<0.05 for RAIT+DTIC versus RAIT. The mean doubling time for the RAIT plus DTIC, and RAIT plus doxorubicin and DTIC groups were 15.5 weeks and 14 weeks, respectively, compared to 7.5 weeks and 9 weeks for DTIC and RAIT alone, respectively. Thus, the combined modality treatment of RAIT plus DTIC extended the mean time to doubling by 100% over the DTIC chemotherapy. No significant difference was observed by either AUC or log rank analyses between the RAIT plus DTIC, and RAIT plus doxorubicin and DTIC groups.

EXAMPLE 6

Studies with Naked Anti-CEA Alone

Therapy with Naked hMN-14

Figure 6:
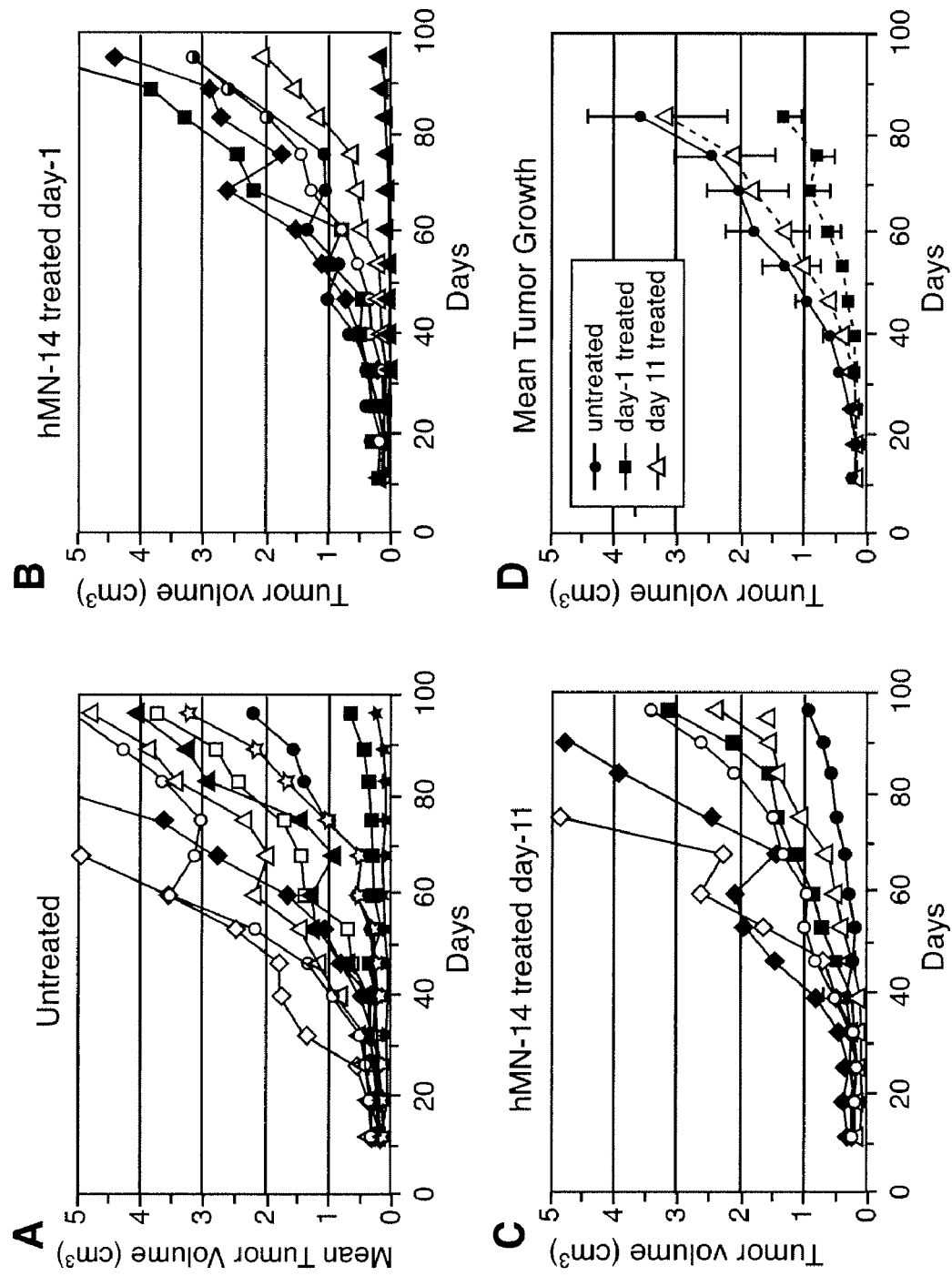
FIG. 6. Graph comparing the effectiveness of naked hMN-14 with treatment regimens in mice bearing TT xenografts. Animals were given s.c. injections of TT cells, and either left untreated (A) or given an i.v. injection of 0.5 mg hMN-14 1 day (B) or 11 days (C) later. Lines in panels A, B, and C represent tumor volumes of individual animals. Means of respective treatment groups are shown in panel D. Error bars represent standard error of the mean and are shown only in one direction for clarity. ♦, untreated; □, day-1 treated; Δ, day-11 treated.

To study the effect of unlabeled hMN-14 on the growth of TT tumors in nude mice, a single injection of hMN-14 was administered i.v. either one day or eleven days post tumor cell injection. FIG. 6 shows the tumor growth curves of animals treated with 0.5 mg hMN-14/mouse compared to untreated controls. The untreated group contained 16 animals; the two treatment groups contained 10 animals each. A significant growth delay was observed between the untreated group and the group treated on day-1 post tumor injection. Significant differences in the mean tumor sizes (p<0.05) were observed from day-32 through day-93. Between day-32 and day-60 there was a 64-70% inhibition of tumor size in the MN-14 treated group compared to the untreated animals. There were no significant differences between the mean tumor sizes in the day-11 group and untreated animals. Significant delay in tumor growth was also seen by t-test analysis of the area under the growth curves. P<0.05 for the untreated group compared to the group treated one day following tumor injection, but not for the group treated eleven days following tumor injection.

Specificity of Treatment

Figure 7:
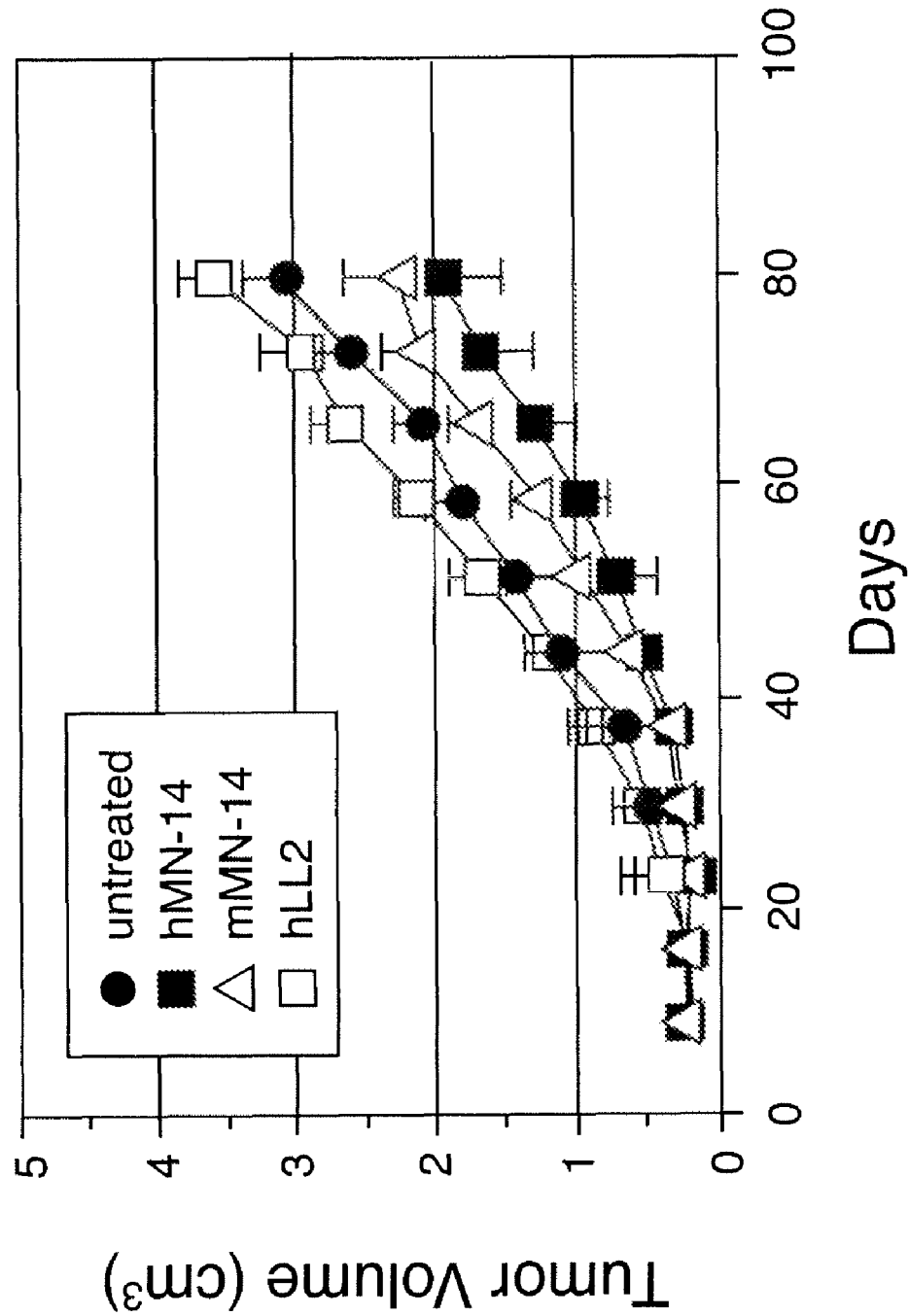
FIG. 7. Graph comparing the effectiveness of humanized and murine MN-14 antibodies in treating medullary thyroid carcinoma. Animals were given s.c. injections of TT cells, and either left untreated or given an i.v. injection of MAb (0.5 mg) 1 day later. Means of respective treatment groups are shown. Error bars represent standard error of the mean and are shown only in one direction for clarity. ♦, untreated; □, hMN-14; Δ, murine MN-14; x, hLL2.

FIG. 7 summarizes the results of a study on the specificity of the anti-tumor response. The effect of unlabeled hMN-14 on the growth of TT tumors in nude mice was compared to that of a negative control humanized MAb, hLL2 (anti-CD22), and the murine MN-14. MAbs (0.5 mg/mouse) were administered (i.v.) one day after TT cells, then three additional weekly doses of 0.5 mg/mouse were given. Groups of 15 animals were studied. The growth inhibition observed in the first study from treatment with 0.5 mg hMN-14 was confirmed in this study. Significant differences in mean tumor sizes (p<0.05) between the hMN-14 and the untreated group were observed starting at day-23. At day-37 the mean tumor volume in the group treated with hMN-14 was 42.7% of the untreated control animals. Treatment with murine MN-14 yielded results similar to the hMN-14. Treatment with hLL2 did not slow tumor growth; instead there was a small (not significant) increase in growth rate. For example, at day-37 87% of the tumors treated with hMN-14 were less than 0.5 $cm^3$, compared to 40% of the untreated and 29% of the hLL2 treated group. T-test analysis of the area under the growth curves demonstrated significant differences (p<0.05) between the untreated group and the groups treated with either hMN-14 or murine MN-14, but not the group treated with hLL2. In addition, the hMN-14 group was significantly different from the hLL2 group but not the murine MN-14 treated animals.

Effect of Dose

To study the effect of dose of unlabeled hMN-14 on the growth of TT tumors in nude mice, increasing doses of hMN-14 were evaluated. Antibody doses were administered 1 day after TT cells, then weekly until the termination of the study. Weekly doses ranged from 0.125 mg to 2.0 mg hMN-14/mouse in groups of six mice. Significant differences in mean tumor sizes and area under the growth curves between the untreated group and all treatment groups were observed (FIG. 8). For example, between day-21 and day-49 mean tumor volume in the 2 lowest hMN-14 treatment groups were 27-40% of the size of tumors in the untreated animals. Treatment with the lower doses, 0.125 mg and 0.25 mg, appeared to be more effective than treatment with the higher doses, although the difference did not reach statistical significance.

Timing

Figure 9:
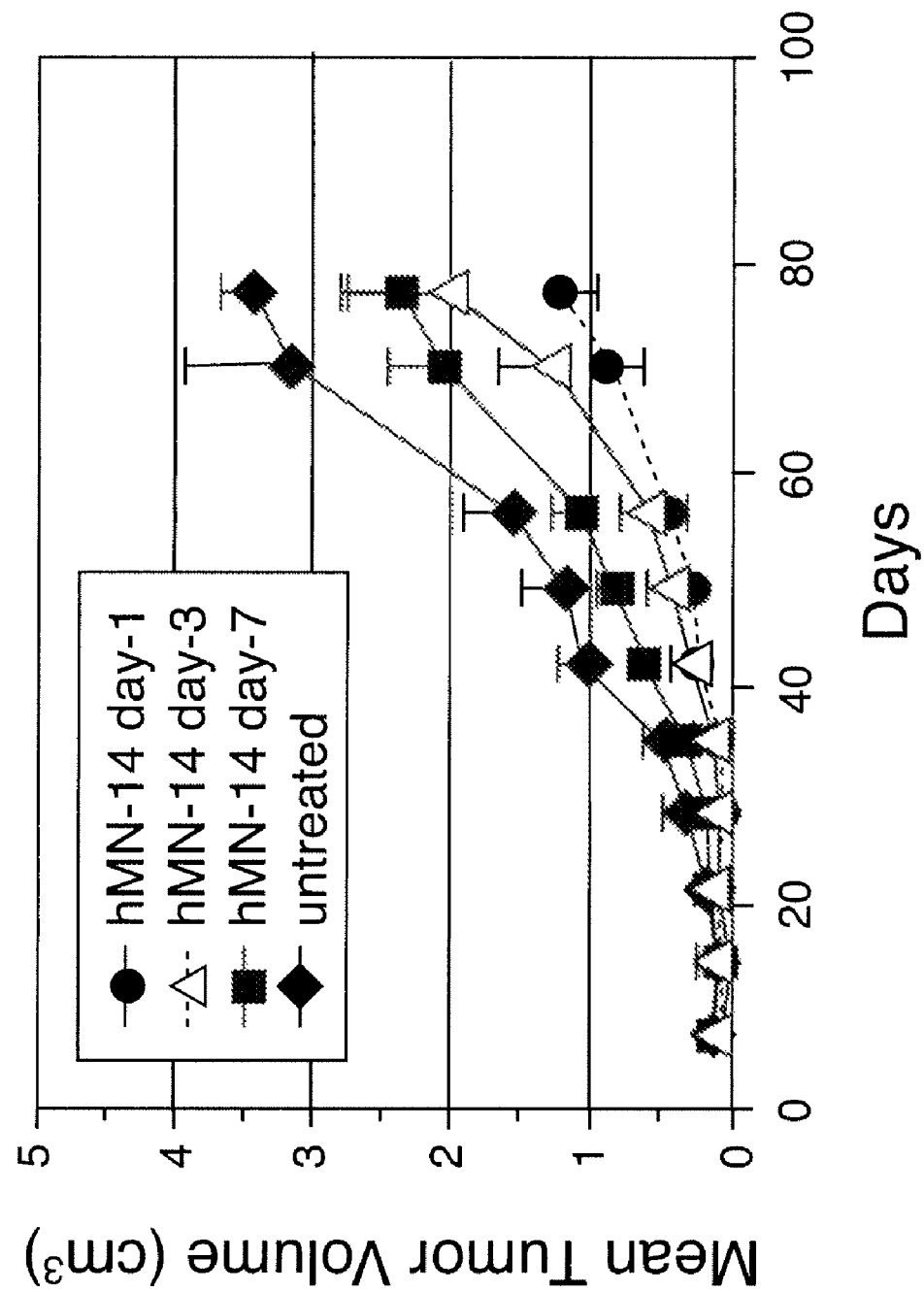
FIG. 9. Graph comparing the effectiveness of different treatment times in TT bearing nude mice. Animals were given i.v. injections of 0.25 hMN-14 either 1 (●), 3 (▲), or 7 (■) days after s.c. injection of TT cells, or left untreated (♦). Means of respective treatment groups are shown. Error bars represent standard error of the mean and are shown only in one direction for clarity.

The effect of time between TT injection and initial dose of hMN-14 on the growth of TT tumors in nude mice was evaluated by varying the day of administration of MAb. hMN-14 (0.25 mg) was administered either 1, 3, or 7 days after TT cells, then weekly until termination of the study. Groups of 7-8 animals were studied. Results are summarized in FIG. 9. Significant differences in mean tumor sizes (p<0.05) between the untreated group and all three treatment groups were observed. However, the difference in mean tumor size between the untreated mice and the day-7 treatment group was only significant at one time point, day-28. Day-1 treated mice yielded significant differences from 21-77 days, and day-3 treated mice yielded significant differences from 21-70 days. T-test analysis of the area under the growth curves indicated significant growth inhibition for the groups treated with hMN-14 either 1 or 3 days after TT cell administration compared to untreated group. This analysis did not reach the 95% confidence limit for difference between the untreated group and the group treated on day-7 (p=0.057 at 5 weeks).

EXAMPLE 7

Combined Naked Anti-CEA Plus DTIC Therapy of MTC

Figure 10:
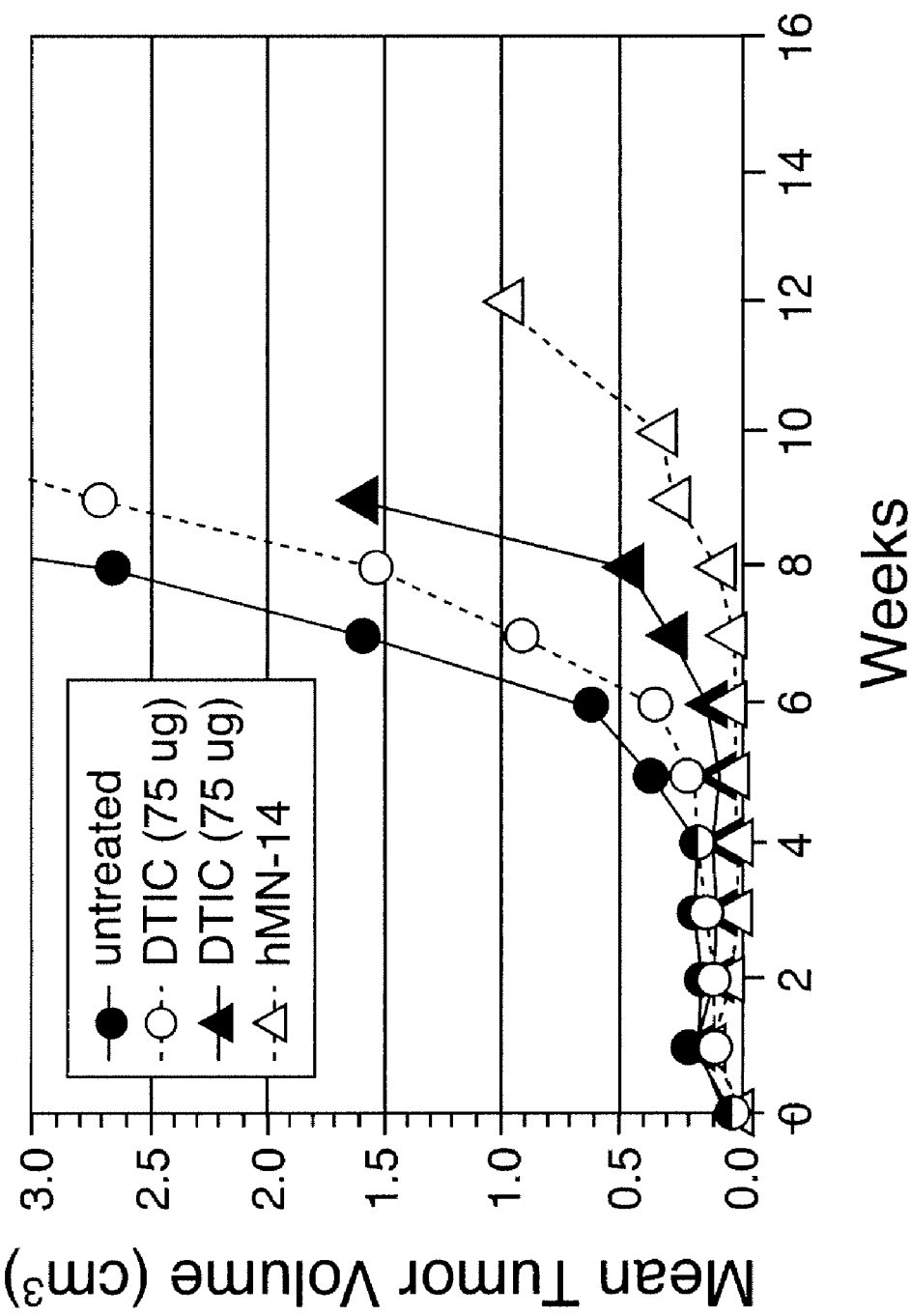
FIG. 10. Graph comparing treatment of TT bearing nude mice with hMN-14 plus DTIC, DTIC alone, hMN-14 alone, and untreated mice. Animals were given i.p. injections of hMN-14 at 100 µg/dose on days 2, 3, 4, 5, 7, 8, 9, 10 and 11, 15, and 22, then every 7 days (○); DTIC, 75 µg/dose on days 2, 3, and 4 (▲); the combination of these hMN-14 and DTIC regimens (Δ); or left untreated (♦). Means of respective treatment groups are shown; 10 animals/group.
Figure 12A:
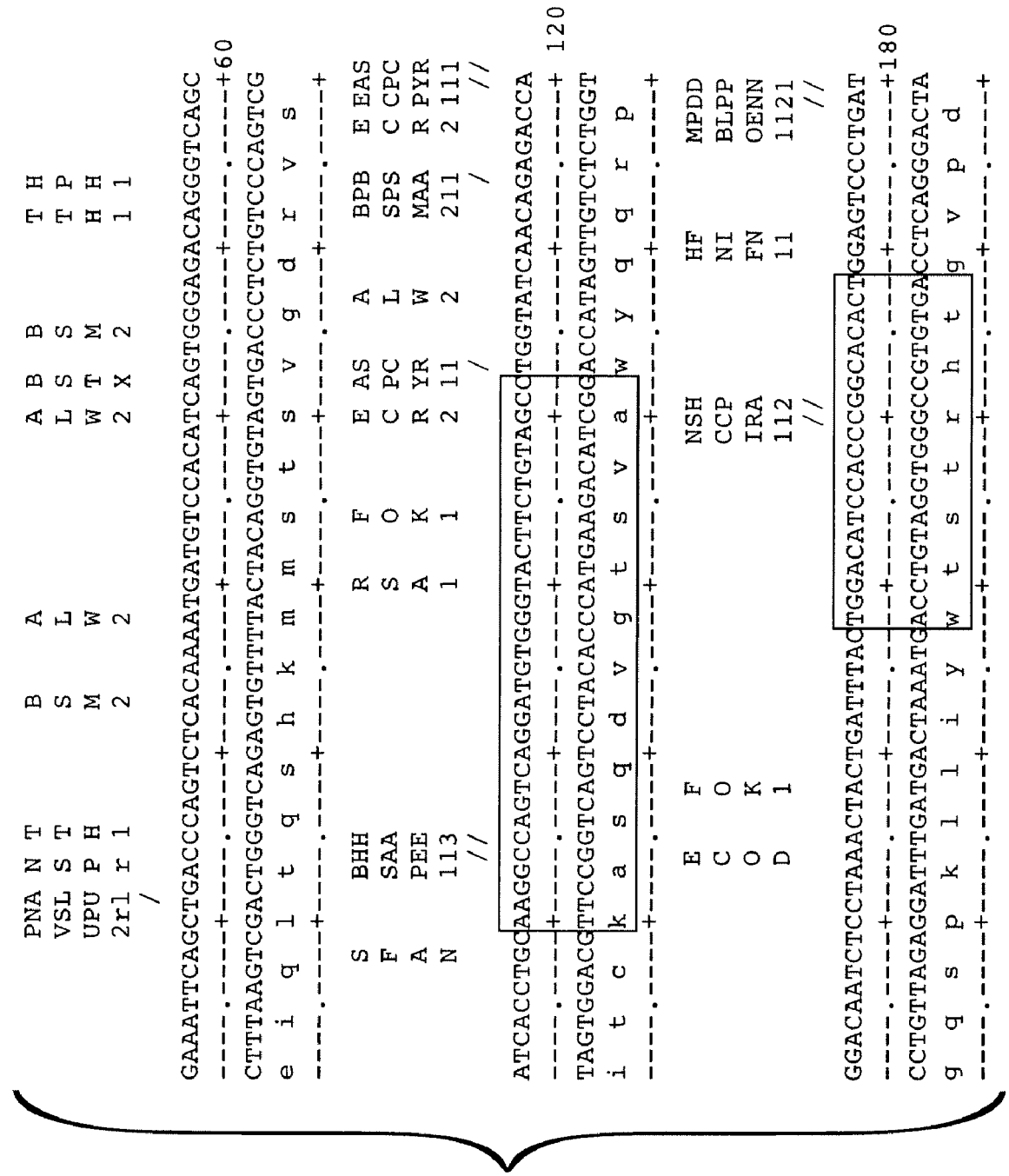
FIGS. 12A and 12B show the consensus DNA sequence of the murine MN-14 variable region light chain (VK) (SEQ ID NO: 3) and the amino acid sequence (SEQ ID NO: 4) encoded by the DNA sequence. The CDRs are enclosed in boxes.
Figure 12B:
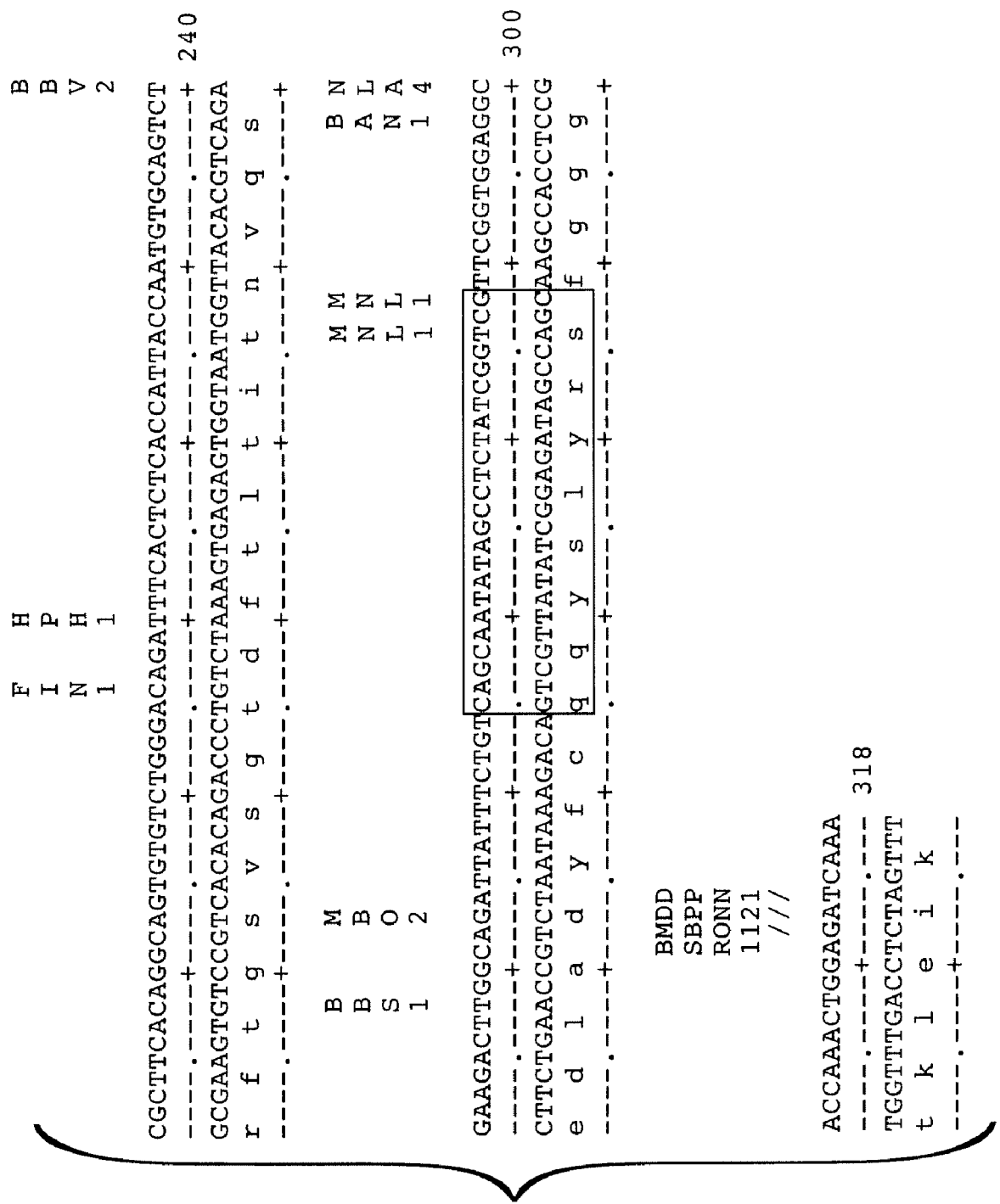

To study whether naked hMN-14 can add to the efficacy of DTIC, TT bearing nude mice were given DTIC (75 µg/dose)

in combination with a course of treatment of the unlabeled MAb. DTIC was administered for 3 consecutive days at 75 µg/dose as one course, beginning 2 days after s.c. injection of TT cells. hMN-14 MAb treatment was initiated on the same day as the first dose of DTIC, at 100 µg/dose/day for 5 days in the first two weeks, then twice weekly. Significant delays in tumor growth were caused by these schedules of either MAb therapy or chemotherapy alone (FIG. 10). The 75 µg dose of DTIC in combination with this schedule of hMN-14 was significantly more effective than either treatment alone ($P<0.02$). At 7 weeks, 8/10 mice in the 75 µg DTIC+MAb group had no palpable tumor, compared to 1/10 in the 75 µg DTIC-only group and 0/10 in the untreated and MAb-only groups. Mean tumor volumes at 7 weeks were 0.018+0.039 $cm^3$ (75 µg DTIC+hMN-14), 0.284+0.197 $cm^3$ (75 µg DTIC), 0.899+0.545 $cm^3$ (hMN-14) and 1.578+0.959 $cm^3$ (untreated).

The anti-CEA MAb MN-14 has shown unexpected antitumor efficacy in MTC without conjugation to a cytotoxic agent. Differences in mean tumor sizes between the hMN-14 treated and the untreated groups were observed beginning at 3 weeks and lasting at least 2 months. Treatment with isotype matched negative control MAbs did not slow tumor growth. This is the first evidence of tumor suppression with a "naked" anti-CEA MAb. However, combined therapy of the naked anti-CEA MAb with DTIC augments the anti-tumor effects of antibody or chemotherapy alone, without increased toxicity. The superiority of the combined modality treatment argues for the integration of CEA-MAb therapy into chemotherapeutic regimens for MTC management.

EXAMPLE 8

Figure 15:
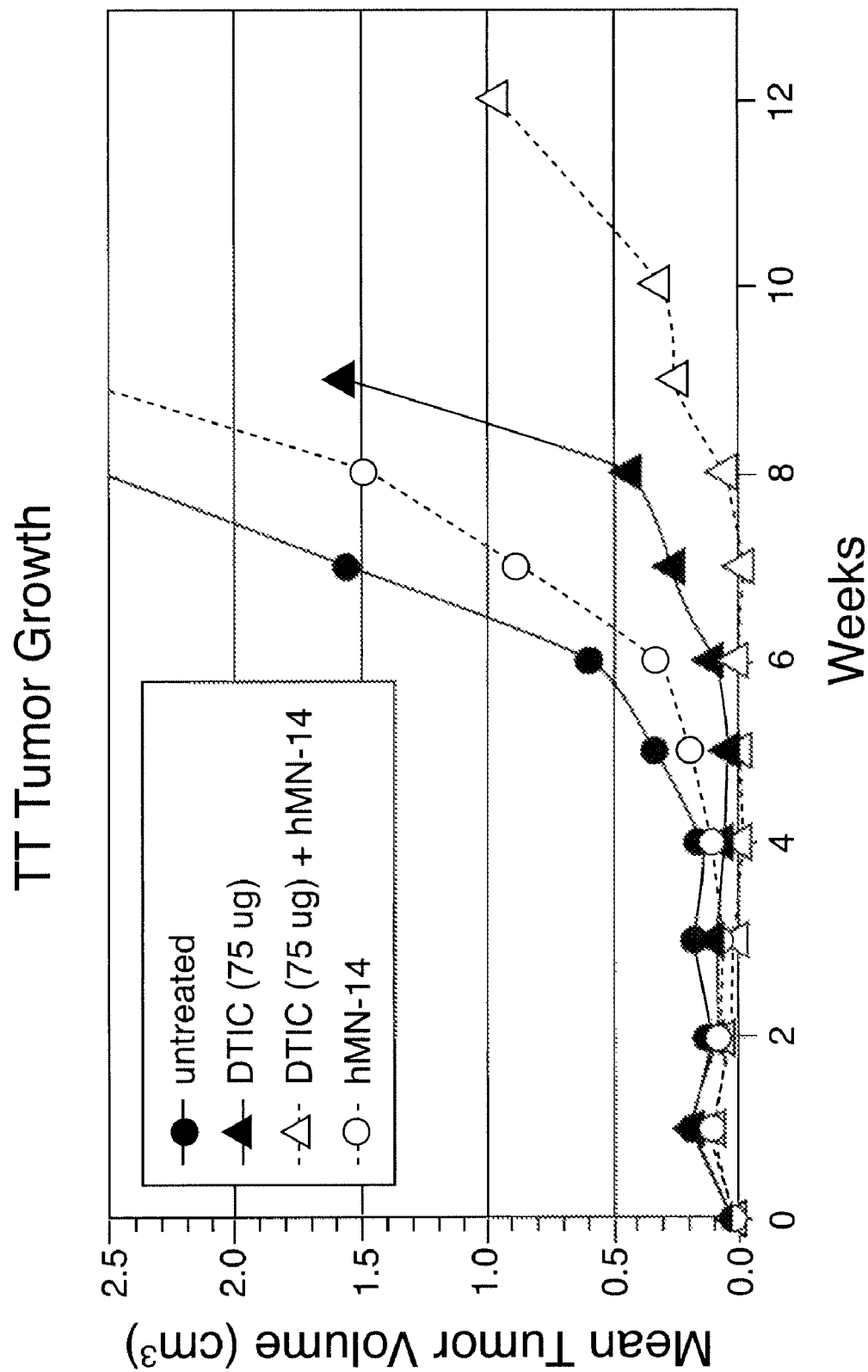
FIG. 15.

FIG. 15 shows the effects of naked hMN-14 CEA MAb and DTIC treatment in a medullary thyroid cancer model. Treatment was initiated 2-days after tumor transplantation. DTIC was administered at ~75 µg on days 2, 3, and 4 at 7.5% of the MTD to mice. hMN-14 was administered at 100 µg/day on days 2-5, 7-10, 11, 15, 22, and then once per week. The results show a statistically significant difference ($P<0.05$) between the areas under the curve for all groups. Naked hMN-14 CEA MAb treatment showed a significant effect on inhibiting tumor growth. When combined with DTIC, a surprisingly enhanced level of inhibition of tumor growth occurred relative to either treatment alone.

EXAMPLE 9

Naked Anti-CEA Antibody Treatment Plus CPT-11 or 5-FU in Colon Cancer Cells

The present experiment discloses the in vitro and in vivo effect of a humanized, naked anti-CEA, hMN-14 antibody (hMN-14) alone, and in combination with chemotherapy on colon cancer growth.

Methods and Materials

Antibody Production. The CDR-grafted (humanized) MN-14 (hMN-14) anti-carcinoembryonic antigen (CEA) (Sharkey, R. M., et al., *Cancer Res*, 55: 5935-5945, 1995) along with the murine MN-14 and other antibodies targeting different CEA epitopes (NP1, NP3, MN3, MN15; (Sharkey, R. M., et al., *Cancer Res*, 50: 2823-2831, 1990) were purified by protein A and ion-exchange chromatography (Q-Sepharose; Pharmacia, Piscataway, N.J.). Purity was tested by immunoelectrophoresis, polyacrylamide gel electrophoresis using reducing and non-reducing conditions and size-exclusion high-pressure liquid chromatography.

In Vivo Therapy Studies. Survival therapy studies were performed using a CEA-positive GW-39 intrapulmonary micrometastasis model (Sharkey, R. M., et al., *J Natl Cancer Inst.*, 83: 627-632, 1991; Blumenthal, R. D., et al., *Cancer Res*, 52: 6036-6044, 1992). Stock subcutaneous GW-39 human colorectal tumors were used to prepare a 10% or 5% cell suspension. Cells (30 µl) were injected i.v. into the caudal vein. HuMN-14 IgG was initiated on either day 0 or day 3 after cell implantation and administered daily×14 days and twice weekly thereafter for the duration of the study at a dose of 100 µg/d. CPT-11 was administered at a dose of 160 µg daily for 5 days i.p. (20% of the MTD) starting on day 0 or day 3 after cell implantation. For some studies, the stock GW-39 tumor came from mice that received 100,000 U of IFNγ twice daily for 4 days to upregulate CEA expression (Greiner, J. W., et al., 16: 2129-2133, 1996), which was confirmed by immunohistology as previously described (Blumenthal, R. D., et al., *Int. J. Cancer*, 51: 935-941, 1992). Body weight was monitored weekly and animal survival recorded. Results were analyzed with the Kaplan-Meir test and median survival time determined.

In Vivo Effects of Antibody-Induced Chemosensitization of Cancer Cells.

The effect of hMN14-induced chemosensitization was apparent in vivo as well as in vitro. Survival curves for mice bearing GW-39 intrapulmonary micrometastases, as described above, and untreated or treated with hMN14 alone (100 µg/d×14 d and twice weekly for the duration of the study), a 10% MTD of CPT-11 (80 µg/d×5 days) alone or both modalities together. Treatment was initiated the day of cell implantation (30 µl of a 10% GW-39 cell suspension). Each treatment group started with 10 mice and the study was repeated twice. The results show that co-administration of hMN-14 and CPT-11 to nude mice bearing GW-39 lung micrometastases increases survival beyond the effect of either modality alone. Administration of a 10% MTD of CPT-11 resulted in a 1-week increase in median survival from 56 days to 63 days ($p<0.05$). Median survival time of animals dosed with both hMN-14 and CPT-11 on day 0 increased by an additional 2 weeks to 77 days ($p<0.005$ compared with untreated mice). Since maximal antibody accretion occurs 3 days post injection, hMN-14 treatments were initiated 3-days before CPT-11 to determine whether such dosing would further enhance the therapeutic effect of the combined modality treatment approach by allowing high antibody uptake and chemosensitization in vivo. The results demonstrate that the 3-day pretreatment with hMN-14 followed by CPT-11 increased median survival to 105 days ($p<0.001$), compared with CPT-11 alone on day 3, with a median survival of 70 days. In this study, co-treatment of hMN-14 and CPT-11 was superior, as evidenced by a median survival of 70 days vs. CPT-11 alone on day 0, with a median survival of 63 days or untreated mice with a median survival of 35 days. The results were similar for a further experiment where a 5% GW-39 cell suspension was used instead of the 10% GW-39 cell suspension.

EXAMPLE 10

In Vivo Effect of Pretreatment with an Immunomodulator Prior to Treatment with hMN-14 and CPT-11 on Tumor Cell Chemosensitivity A further experiment evaluated the combined treatment of hMN-14 with CPT-11, initiated together in mice with GW-39 tumors expressing higher CEA levels, as a result of pretreatment of GW-39 stock tumors (10% GW-39 cell suspension) with interferon-γ (IFNγ). The experiments involving interferon-gamma enhancing the antitumor effects of naked CEA antibody (hMN-14) were conducted as follows.

First, GW-39 human colon cancer was grown subcutaneously in a mouse that received 100,000 units of IFN-gamma twice a day for 4 days. A control mouse with GW-39 tumor was not given IFN. Experimental mice were injected i.v. with a 5% suspension of GW-39 (w/v) from either of the two mice (i.e., with or without IFN treatment) into two groups of eight. Four of each received tumor from the IFN-treated mice and four from the untreated mice. One group of 8 mice then received hMN-14 (100 ug per day×14 days and then twice weekly thereafter until expt was ended), another group CPT-11 at 160 ug/day×5 days (=20% of maximum tolerated dose), a third group received the same doses of antibody+drug combined, and a fourth group that was not treated at all. Animal weights were measured and survival determined weekly. Also, samples of stock tumor treated with IFN in the mice that were later implanted were also processed for immunohistology to assess increase in CEA expression in the tumors from mice treated with IFN-gamma, and this was controlled by also treating the suspensions by immunohistology with an irrelevant IgG, such as Ag8, which showed no CEA staining.

EXAMPLE 11

Figure 21:
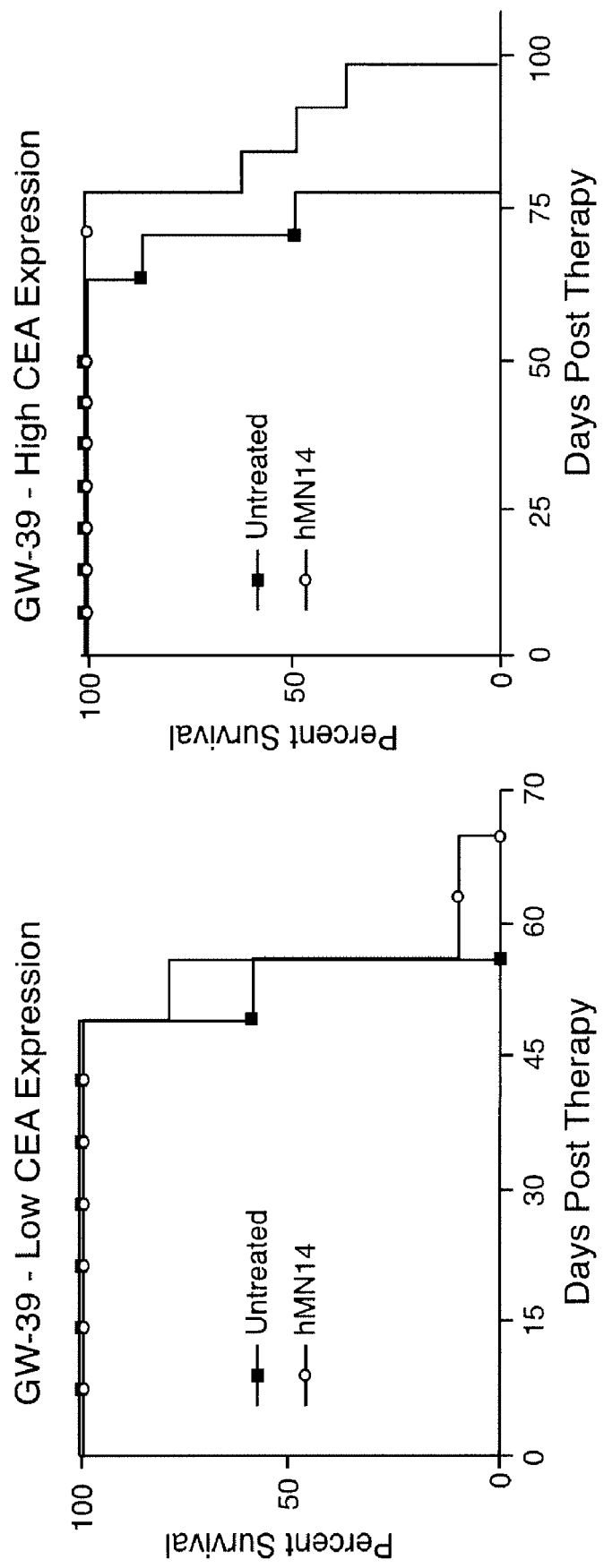
FIG. 21.

A comparison was performed of the effects of naked hMN-14 CEA Mab on low and high (induced by interferon-gamma, as described earlier) CEA-expressing tumor cells in an animal model. The results demonstrate that increased expression of CEA antigen on tumor cells correlates with improved efficacy of anti-CEA antibody. The results of the comparison study are shown in FIG. 21. Thus, interferon-gamma pretreatment is useful to boost the efficacy of anti-CEA antibody therapy in the treatment of cancer.

EXAMPLE 12

Sigmoid Colon Cancer Therapy with CEA Antibody and GM-CSF

J. R. is a 62-year-old man who is refractive to chemotherapy with 5-fluorouracil and leukovorin to reduce his metastases to the liver found at the time of discovery and removal of his sigmoid colon cancer. H is plasma titer of carcinoembryonic antigen (CEA) at presentation is 34 ng/mL, and computed tomography of the liver shows several small lesions measuring between 2 and 4 cm in diameter in the right lobe; other radiological studies appear to be normal. Immunotherapy with humanized anti-CEA IgG$_1$, hMN-14, monoclonal antibody is begun on a weekly basis for 4 weeks, at an intravenous dose of 300 mg/m$^2$ infused over 2 hours. One week prior to hMN-14 therapy, the patient receives 2 subcutaneous injections of 200 mcg/m$^2$ GM-CSF (sargamostim, Leukine®), 3 days apart, and continued twice weekly during the 4 weeks of hMN-14 therapy. After these four weeks, both hMN-14 and GM-CSF are given at the same doses every other week for an additional 3 months, but the dose of GM-CSF is increased to 250 mcg/m$^2$. Prior to each administration of the humanized CEA antibody, the patient is given diphenhydramine (Benadryl®), 50 mg orally, and acetaminophen (Tylenol®), 500 mg orally. At this time, the patient is restaged, with CT measurements made of the liver metastases and diverse radiological scans of the rest of the body. Blood is also taken for chemistries and for determination of his blood CEA titer. No areas of disease outside of the liver are noted, but the sum of the diameters of the measurable tumors in the liver appear to decrease by 40 percent, and the patient's blood CEA titer decreases to 18 ng/mL, thus indicating a therapeutic response. Immunotherapy with hMN-14 and GM-CSF, given once every other week at 200 mg/m$^2$ for hMN-14 and 250 mcg/m$^2$ for GM-CSF, are administered for another 2 months, and restaging shows additional decrease in the sum of the diameters of the liver tumors and a fall in the CEA titer to 10 ng/mL. Since tumor decrease is measured as being >65% over the pre-therapy baseline, the therapy is considered to have provided a partial response. After this, the doses were made less frequent, once every month for the next six months, and all studies indicate no change in disease. The patient is then followed for another 10 months, and remains in a partial remission, with no adverse reactions to the therapy, and generally without any symptoms of disease.

EXAMPLE 13

Combined Immunotherapy and Chemotherapy of Metastatic Colon Cancer

S. T. is a 52-year-old woman presenting with liver and lung metastases of colon cancer following resection of the primary tumor. She is placed on a combined chemotherapy and immunotherapy protocol based on the Gramont schedule (A. de Gramont et al., *J Clin Oncol.* 2000; 18:2938-1947), but with the addition of humanized anti-CEA monoclonal antibody IgG$_1$. Prior to infusions of the antibody, she receives 50 mg orally of diphenhydramine (Benadryl®) and 500 mg orally of acetaminophen (Tylenol®). She receives a 2-hr infusion of leucovorin (200 mg/m$^2$/day) followed by a bolus of 5-fluorouracil (400 mg/m$^2$/day) and 22-hour continuous infusion of 5-fluorouracil (600 mg/m$^2$/day) for 2 consecutive days every 2 weeks, together with oxaliplatin at 85 mg/m$^2$ as a 2-hr infusion in 250 mL of dextrose 5%, concurrent with leukocorin on day 1 (FOLFOX4 schedule). The patient also receives anti-emetic prophylaxis with a 5-hydroxyltryptamine-3-receptor antagonist. One week prior to this 2-week chemotherapy cycle, hMN-14 monoclonal anti-CEA antibody is infused over 2 hrs at a dose of 200 mg/m$^2$, and repeated each week of the 2-week chemotherapy cycle, and every week thereafter for the next month with another chemotherapy cycle. Also, a subcutaneous dose of 5 mcg/kg/day of G-CSF (filgrastim, Neupogen®) is administered once weekly beginning with the second chemotherapy cycle, and continued at this dose for the duration of immunotherapy with hMN-14 antibody, over the next 3 months. A total of 5 cycles of chemotherapy with continued administration of hMN-14 antibody and filgrastim. Thereafter, hMN-14 and filgrastim therapy is given, at the same doses, every other week for the next 3 months, without chemotherapy. The patient is staged 2 months later, and her liver and lung metastases show shrinkage by computed tomography measurements of >80 percent of disease measured in the liver and lungs, as compared to the measurements made prior to therapy. Her blood CEA titer also shows a drop from the pre-therapy level of 63 ng/mL to 9 ng/mL. She is followed over the next 6 months, and her disease appears to be stable, with no new lesions found and no increase in the disease remaining in the liver and lungs. The patient's predominant toxicity is peripheral sensory neuropathy, which consists of laryngeopharyngeal dysesthesia. The patient also experiences diarrhea, mucositis, nausea and vomiting during the chemotherapy cycles, but these are not excessive. She does not experience any adverse events when only immunotherapy is administered, and is able to return to full-time activities without any significant restrictions.

EXAMPLE 14

Figure 16:
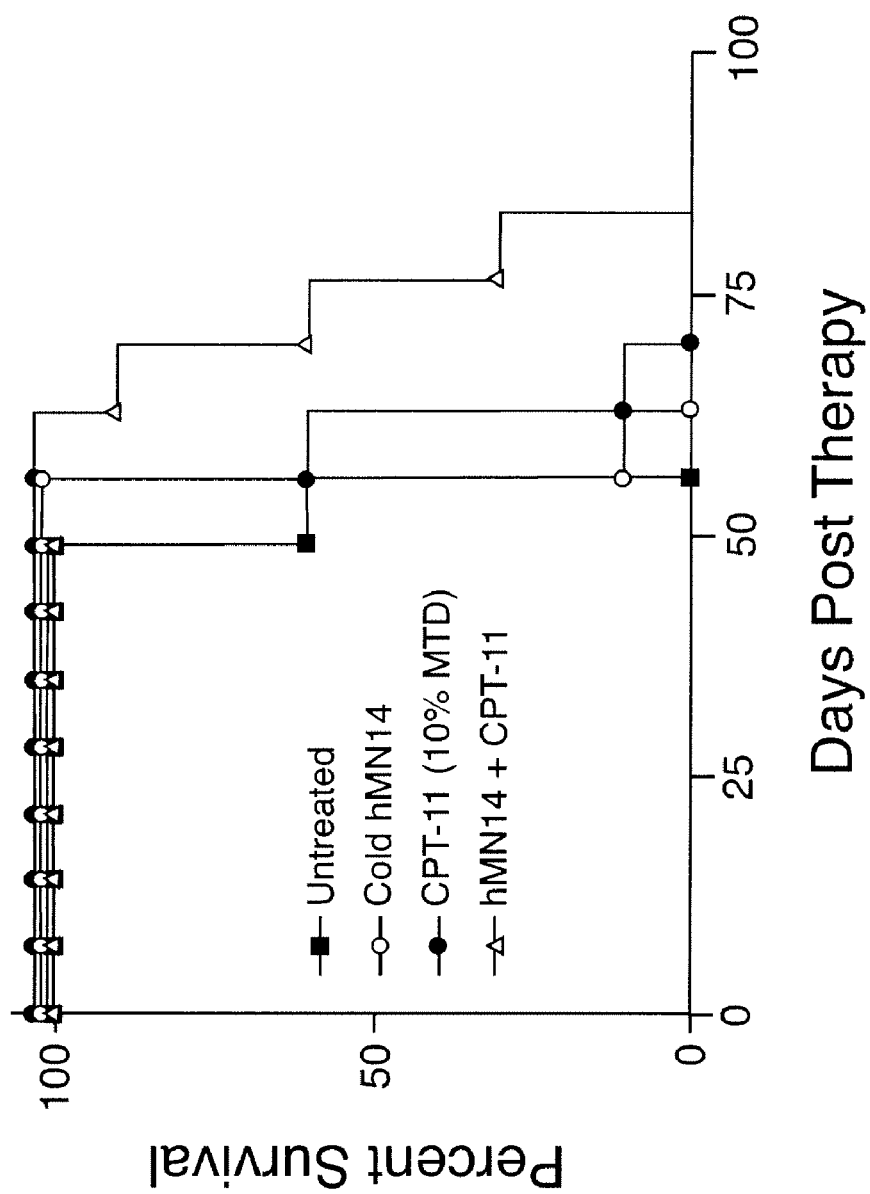
FIG. 16.

FIG. 16 shows the effects of naked hMN-14 CEA Mab and CPT-11 treatment in an advanced colon cancer model. hMN-14 was given to mice at a dose of 100 µg/day over 14 days and then 2 times/week thereafter, starting on day 0 after tumor implantation. CPT-11 was given at 60 µg/day over 5 days. No effect of hMN-14 by itself is apparent under these conditions, and only a modest effect of CPT-11 ($p<0.05$) was observed. However, hMN-14 increases the effect of CPT-11, as seen by comparing the CPT-11 median survival of 63 days vs. combination therapy median survival of 77 days ($p<0.005$). Combination therapy with hMN-14 CEA Mab and CPT-11 significantly prolongs survival of an animal with advanced human colonic tumor metastasis.

EXAMPLE 15

Figure 17:
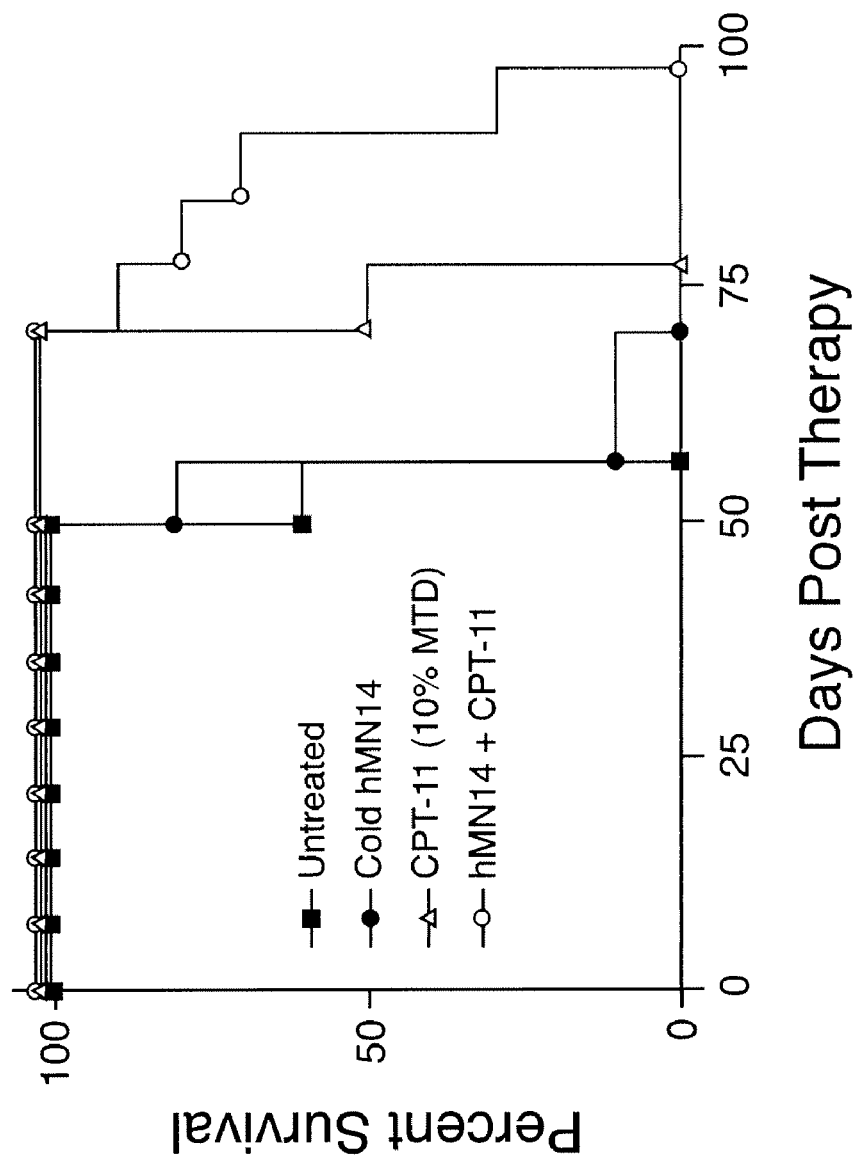
FIG. 17.

FIG. 17 shows the effects of naked hMN-14 CEA MAb and CPT-11 treatment in a low tumor burden cancer model. In a reduced tumor burden model utilizing a 5% tumor cell suspension, CPT-11, hMN-14 alone, and combination therapy of hMN-14+CPT-11 were compared. Dosages were as indicated in Example 14. There was no apparent effect of hMN-14 alone under these conditions. CPT 11 alone resulted in a median survival time of 70 days. By contrast, the combination therapy produced a median survival time of 91 days ($p<0.025$). The combination of hMN-14 and CPT-11 significantly prolongs survival of animals with low tumor burden in a metastatic model of human colonic cancer.

EXAMPLE 16

Figure 18:
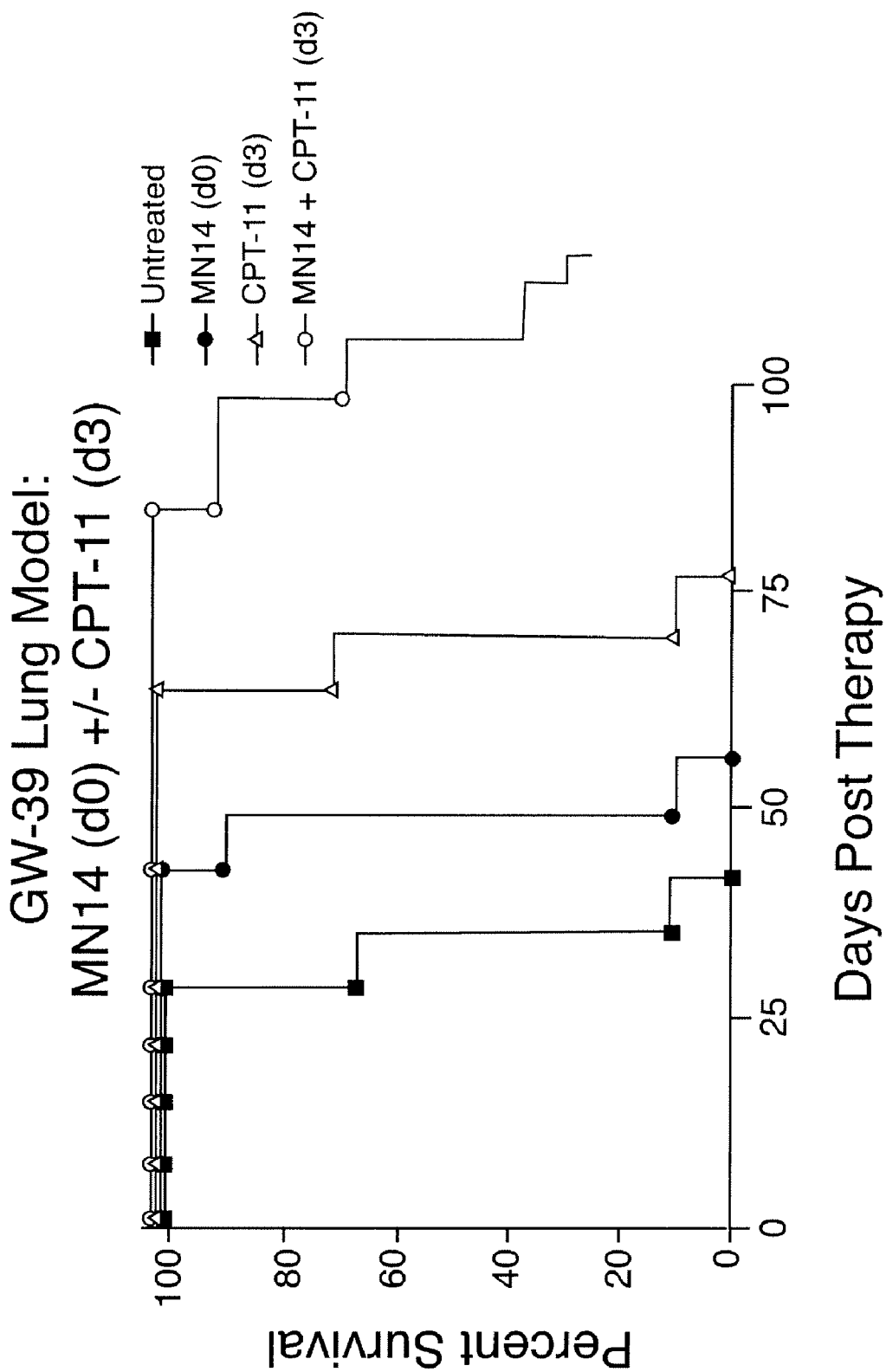
FIG. 18.

FIG. 18 shows the effects of pre-treatment with naked hMN-14 CEA Mab given 3 days prior to CPT-11 treatment in a cancer model. In a reduced tumor burden model utilizing a 5% tumor cell suspension, CPT-11, hMN-14 alone, and combination therapy of hMN-14+CPT-11 where the hMN-14 was administered 3 days prior to the CPT-11 were compared. Dosages were as indicated in Example 14. hMN-14 alone increased median survival time by 21% ($p<0.05$) under these conditions. CPT 11 alone increased survival by 76% ($p<0.001$). By contrast, the combination therapy where hMN-14 is administered 3 days prior to CPT-11 produced a median survival time increase of an additional 58% above CPT-11 alone ($p<0.001$ compared with CPT-11 alone). Pre-treatment with hMN-14 significantly prolongs survival of animals with low tumor burden in a metastatic model of human colonic cancer.

EXAMPLE 17

Figure 19:
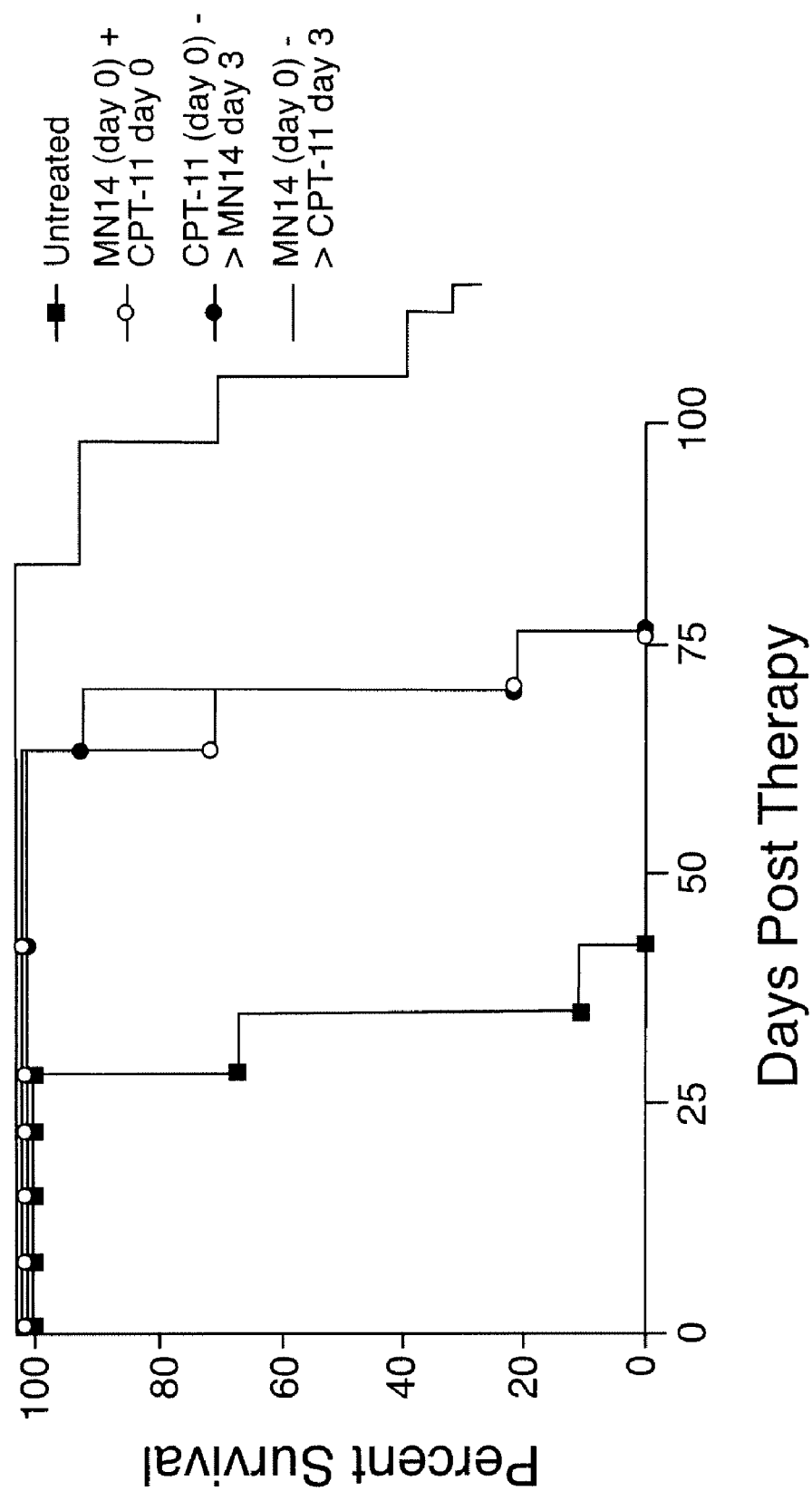
FIG. 19.

FIG. 19 shows a comparison of various administration schedules of naked hMN-14 CEA MAb and CPT-11 in a human colon cancer model. Giving hMN-14 3 days before CPT-11 is the most effective. Dosages were as indicated Example 14. When the order is reversed (CPT-11 is given 3 days before hMN-14) or when both are given together at the same time, median survival time of 70 days was an increase over the untreated control group (35 days) but was still significantly less than the median survival time of 105 days with the hMN-14 pre-treatment 3 days before CPT-11.

EXAMPLE 18

Figure 20:
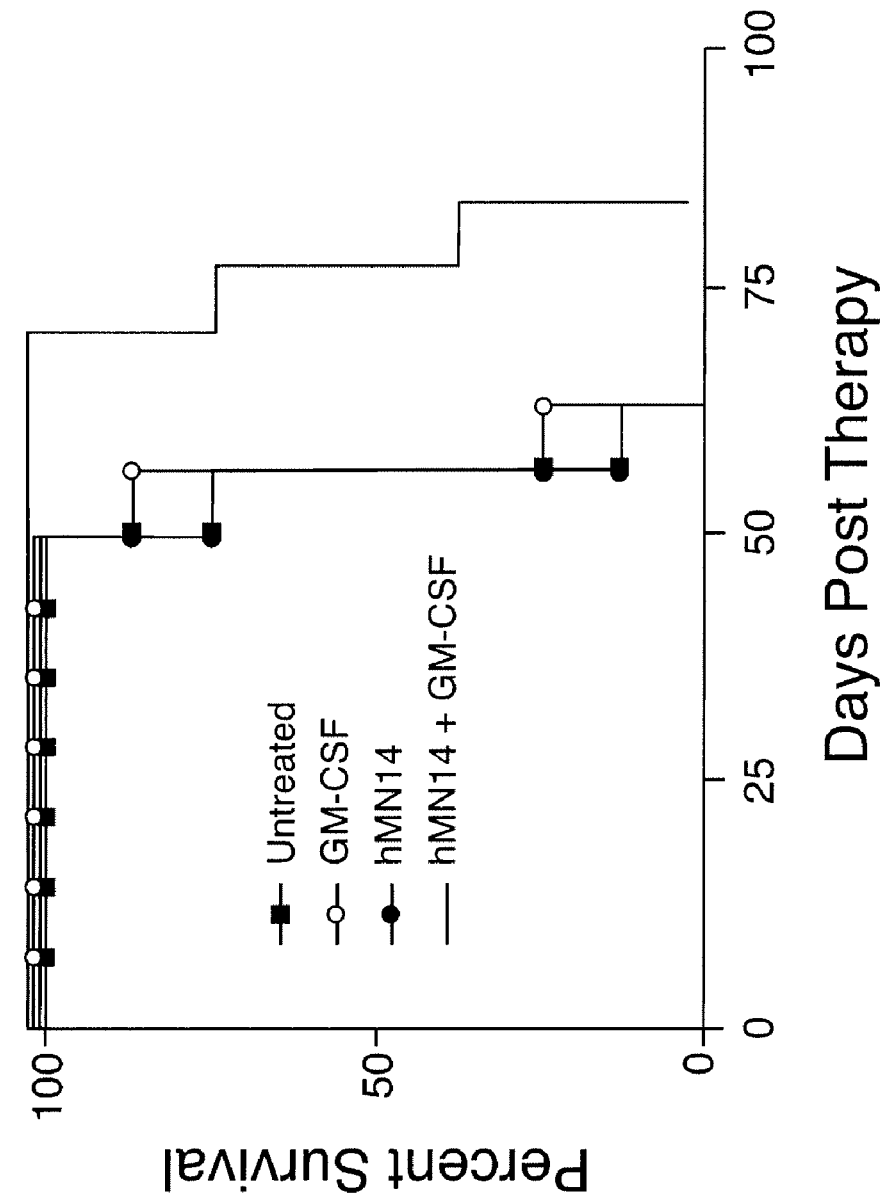
FIG. 20.

FIG. 20 shows the effects of GM-CSF pre-treatment on naked hMN-14 CEA Mab therapy in a human colon cancer model. GM-CSF was administered at a dose of 1 µg/mouse/day on days −4, −3, −2, and −1. Tumor cells were implanted at day 0 along with hMN-14 treatments. Other dosages were as indicated Example 14. The GM-CSF pre-treatment resulted in a statistically significant increase in median survival time ($p<0.002$) over either GM-CSF alone or hMN-14 alone.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications and patent applications and patents cited in this specification are herein incorporated in their entirety by reference.

What is claimed is:

1. A method for treating a CEA and/or NCA expressing cancer comprising:
   a) administering to a subject with a CEA and/or NCA expressing cancer a naked monovalent Class I anti-CEA monoclonal antibody (MAb) or antigen-binding fragment thereof; and
   b) administering either concurrently or sequentially at least one anti-cancer therapeutic agent.

2. The method of claim 1, wherein the therapeutic agent is selected from the group consisting of a second antibody or fragment thereof, an immunoconjugate, a cytotoxic agent, a chemotherapeutic agent, a radionuclide, an immunomodulator, a photoactive therapeutic agent, an antisense oligonucleotide and a hormone.

3. The method of claim 2, wherein the therapeutic agent comprises vincristine, doxorubicin, DTIC, cyclophosphamide, CPT-11, oxaliplatin, gemcitabine and 5-fluorouracil/leucovorin.

4. The method of claim 2, wherein the therapeutic agent is selected from the group consisting of vincristine, doxorubicin, DTIC, cyclophosphamide, CPT-11, oxaliplatin, gemcitabine and 5-fluorouracil/leucovorin.

5. The method of claim 2, wherein the therapeutic agent is a second naked antibody or an immunoconjugate.

6. The method of claim 5, wherein the second naked antibody or immunoconjugate comprises a Class II or Class III anti-CEA antibody or fragment thereof.

7. The method of claim 5, wherein said second naked antibody or immunoconjugate comprises a humanized, chimeric, human or murine antibody or fragment thereof reactive with an antigen selected from the group consisting of EGP-1, EGP-2, MUC-1, MUC-2, MUC-3, MUC-4, antigen bound by PAM4 antibody, KC4, TAG-72, EGFR, HER2/neu, BrE3, Le-Y, A3, A33, Ep-CAM, AFP, Tn, Thomson-Friedenreich antigens, tumor necrosis antigens, VEGF, a tumor angiogenesis antigen, Ga 733, tenascin and fibronectin.

8. The method of claim 1, wherein the cancer is medullary thyroid carcinoma or colon cancer.

9. The method of claim 2, wherein the cytotoxic agent is a drug or toxin.

10. The method of claim 9, wherein the drug possesses a pharmaceutical property selected from the group consisting of antimitotic, alkylating, antimetabolite, antiangiogenic, apoptotic, alkaloid, COX-2, and antibiotic agents and combinations thereof.

11. The method of claim 9, wherein the drug is selected from the group consisting of nitrogen mustards, ethylenimine derivatives, alkyl sulfonates, nitrosoureas, triazenes, folic acid analogs, anthracyclines, taxanes, COX-2 inhibitors, pyrimidine analogs, purine analogs, antimetabolites, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, doxorubicins and a combination thereof.

12. The method of claim 9, wherein the toxin is a microbial, plant or animal toxin selected from the group consisting of ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin and *Pseudomonas* endotoxin.

13. The method of claim 2, wherein the immunomodulator is selected from the group consisting of a cytokine, a stem cell growth factor, a lymphotoxin, a hematopoietic factor, a colony stimulating factor (CSF), an interferon (IFN), erythropoietin, thrombopoietin, tumor necrosis factor (TNF), an interleukin (IL), granulocyte-colony stimulating factor (G-CSF), granulocyte macrophage-colony stimulating factor (GM-CSF), interferon-alpha., interferon-beta, interferon-gamma, a stem cell growth factor designated "S1 factor," IL-1, IL-2, IL-3, IL-6, IL-10, IL-12, IL-18 and IL-21.

14. The method of claim 2, wherein the immunomodulator comprises IL-1, IL-2, IL-3, IL-6, IL-10, IL-12, IL-18, interferon-γ, TNF-α or a combination thereof.

15. The method of claim 1, wherein combination of naked Class I anti-CEA antibody and therapeutic agent is more effective for therapy of a CEA-expressing cancer than either antibody or therapeutic agent alone or the sum of the effects of naked anti-CEA antibody and therapeutic agent.

16. The method of claim 2, wherein the radionuclide is selected from the group consisting of $^{32}$P, $^{33}$P, $^{47}$Sc, $^{59}$Fe, $^{64}$Cu, $^{67}$Cu, $^{75}$Se, $^{77}$As, $^{89}$Sr, $^{90}$Y, $^{99}$Mo, $^{105}$Rh, $^{109}$Pd, $^{111}$Ag, $^{125}$I, $^{131}$I, $^{142}$Pr, $^{143}$Pr, $^{149}$Pm, $^{153}$Sm, $^{161}$Tb, $^{166}$Ho, $^{169}$Er, $^{177}$Lu, $^{186}$Re, $^{188}$Re, $^{189}$Re, $^{194}$Ir, $^{198}$Au, $^{199}$Au, $^{211}$Pb, $^{212}$Pb, $^{213}$Bi, $^{58}$Co, $^{67}$Ga, $^{80m}$Br, $^{99m}$Tc, $^{103m}$Rh, $^{109}$Pt, $^{111}$In, $^{119}$Sb, $^{161}$Ho, $^{189m}$Os, $^{192}$Ir, $^{152}$Dy, $^{211}$At, $^{212}$Bi, $^{223}$Ra, $^{219}$Rn, $^{215}$Po, $^{211}$Bi, $^{225}$Ac, $^{211}$Fr, $^{217}$At, $^{213}$Bi, $^{88}$Y and $^{255}$Fm.

17. The method of claim 1, wherein the subject has a colon, rectal, ancreatic, breast, ovarian, thyroid or lung cancer.

18. The method of claim 1, wherein said antibody fragment is selected from the group consisting of a F(ab')$_2$, a Fab', a Fab, an Fv and an scFv.

19. The method of claim 1, wherein the Class I anti-CEA antibody is MN-3 or MN-15.

* * * * *

SEQUENCE LISTING

```
<160> NUMBER OF SEQ ID NOS: 27

<210> SEQ ID NO 1
<211> LENGTH: 357
<212> TYPE: DNA
<213> ORGANISM: Mus sp.
<220> FEATURE:
<221> NAME/KEY: CDS
<222> LOCATION: (1)..(357)

<400> SEQUENCE: 1 gag gtg aag ctt ctc gag tct gga ggt ggc ctg gtg cag tct gga gga      48
Glu Val Lys Leu Leu Glu Ser Gly Gly Gly Leu Val Gln Ser Gly Gly
  1               5                  10                  15 tcc ctg aaa ctc tcc tgt gca gcc tca gga ttc gat ttt act aca tat      96
Ser Leu Lys Leu Ser Cys Ala Ala Ser Gly Phe Asp Phe Thr Thr Tyr
             20                  25                  30 tgg atg agt tgg gtc cgg cag gct cca ggg aaa ggc cta gaa tgg att     144
Trp Met Ser Trp Val Arg Gln Ala Pro Gly Lys Gly Leu Glu Trp Ile
         35                  40                  45
```

```
gga gaa att cat cca gat agc agt acg att aac tat gcg ccg tct cta    192
Gly Glu Ile His Pro Asp Ser Ser Thr Ile Asn Tyr Ala Pro Ser Leu
 50                  55                  60 aag gat aaa ttc atc gtc tcc aga gac aac gcc aaa aat acg ctg tac    240
Lys Asp Lys Phe Ile Val Ser Arg Asp Asn Ala Lys Asn Thr Leu Tyr
 65                  70                  75                  80 ctg caa atg agc aaa gtg aga tct gag gac aca gcc ctt tat tac tgt    288
Leu Gln Met Ser Lys Val Arg Ser Glu Asp Thr Ala Leu Tyr Tyr Cys
                 85                  90                  95 gca agc ctt tac ttc ggc ttc ccc tgg ttt gct tat tgg ggc caa ggg    336
Ala Ser Leu Tyr Phe Gly Phe Pro Trp Phe Ala Tyr Trp Gly Gln Gly
            100                 105                 110 act ccg gtc act gtc tct gca                                        357
Thr Pro Val Thr Val Ser Ala
        115
```

```
<210> SEQ ID NO 2
<211> LENGTH: 119
<212> TYPE: PRT
<213> ORGANISM: Mus sp.

<400> SEQUENCE: 2

Glu Val Lys Leu Leu Glu Ser Gly Gly Gly Leu Val Gln Ser Gly Gly
 1               5                  10                  15

Ser Leu Lys Leu Ser Cys Ala Ala Ser Gly Phe Asp Phe Thr Thr Tyr
                 20                  25                  30

Trp Met Ser Trp Val Arg Gln Ala Pro Gly Lys Gly Leu Glu Trp Ile
             35                  40                  45

Gly Glu Ile His Pro Asp Ser Ser Thr Ile Asn Tyr Ala Pro Ser Leu
         50                  55                  60

Lys Asp Lys Phe Ile Val Ser Arg Asp Asn Ala Lys Asn Thr Leu Tyr
 65                  70                  75                  80

Leu Gln Met Ser Lys Val Arg Ser Glu Asp Thr Ala Leu Tyr Tyr Cys
                 85                  90                  95

Ala Ser Leu Tyr Phe Gly Phe Pro Trp Phe Ala Tyr Trp Gly Gln Gly
            100                 105                 110

Thr Pro Val Thr Val Ser Ala
        115
```

```
<210> SEQ ID NO 3
<211> LENGTH: 318
<212> TYPE: DNA
<213> ORGANISM: Mus sp.
<220> FEATURE:
<221> NAME/KEY: CDS
<222> LOCATION: (1)..(318)

<400> SEQUENCE: 3 gaa att cag ctg acc cag tct cac aaa atg atg tcc aca tca gtg gga     48
Glu Ile Gln Leu Thr Gln Ser His Lys Met Met Ser Thr Ser Val Gly
 1               5                  10                  15 gac agg gtc agc atc acc tgc aag gcc agt cag gat gtg ggt act tct     96
Asp Arg Val Ser Ile Thr Cys Lys Ala Ser Gln Asp Val Gly Thr Ser
                 20                  25                  30 gta gcc tgg tat caa cag aga cca gga caa tct cct aaa cta ctg att    144
Val Ala Trp Tyr Gln Gln Arg Pro Gly Gln Ser Pro Lys Leu Leu Ile
             35                  40                  45 tac tgg aca tcc acc cgg cac act gga gtc cct gat cgc ttc aca ggc    192
Tyr Trp Thr Ser Thr Arg His Thr Gly Val Pro Asp Arg Phe Thr Gly
         50                  55                  60 agt gtg tct ggg aca gat ttc act ctc acc att acc aat gtg cag tct    240
```

```
Ser Val Ser Gly Thr Asp Phe Thr Leu Thr Ile Thr Asn Val Gln Ser
 65                  70                  75                  80 gaa gac ttg gca gat tat ttc tgt cag caa tat agc ctc tat cgg tcg      288
Glu Asp Leu Ala Asp Tyr Phe Cys Gln Gln Tyr Ser Leu Tyr Arg Ser
                 85                  90                  95 ttc ggt gga ggc acc aaa ctg gag atc aaa                              318
Phe Gly Gly Gly Thr Lys Leu Glu Ile Lys
100                 105
```

<210> SEQ ID NO 4
<211> LENGTH: 106
<212> TYPE: PRT
<213> ORGANISM: Mus sp.

<400> SEQUENCE: 4

```
Glu Ile Gln Leu Thr Gln Ser His Lys Met Met Ser Thr Ser Val Gly
  1               5                  10                  15

Asp Arg Val Ser Ile Thr Cys Lys Ala Ser Gln Asp Val Gly Thr Ser
                 20                  25                  30

Val Ala Trp Tyr Gln Gln Arg Pro Gly Gln Ser Pro Lys Leu Leu Ile
             35                  40                  45

Tyr Trp Thr Ser Thr Arg His Thr Gly Val Pro Asp Arg Phe Thr Gly
 50                  55                  60

Ser Val Ser Gly Thr Asp Phe Thr Leu Thr Ile Thr Asn Val Gln Ser
 65                  70                  75                  80

Glu Asp Leu Ala Asp Tyr Phe Cys Gln Gln Tyr Ser Leu Tyr Arg Ser
                 85                  90                  95

Phe Gly Gly Gly Thr Lys Leu Glu Ile Lys
100                 105
```

<210> SEQ ID NO 5
<211> LENGTH: 117
<212> TYPE: PRT
<213> ORGANISM: Homo sapiens

<400> SEQUENCE: 5

```
Gln Val Gln Leu Gln Glu Ser Gly Pro Gly Leu Val Arg Pro Ser Gln
  1               5                  10                  15

Thr Leu Ser Leu Thr Cys Thr Val Ser Gly Ser Thr Phe Ser Asn Asp
                 20                  25                  30

Tyr Tyr Thr Trp Val Arg Gln Pro Pro Gly Arg Gly Leu Glu Trp Ile
             35                  40                  45

Gly Tyr Val Phe Tyr His Gly Thr Ser Asp Asp Thr Pro Leu Arg
 50                  55                  60

Ser Arg Val Thr Met Leu Val Asp Thr Ser Lys Asn Gln Phe Ser Leu
 65                  70                  75                  80

Arg Leu Ser Ser Val Thr Ala Ala Asp Thr Ala Val Tyr Tyr Cys Ala
                 85                  90                  95

Arg Asn Leu Ile Ala Gly Cys Ile Asp Val Trp Gly Gln Gly Thr Thr
                100                 105                 110

Val Thr Val Ser Ser
        115
```

<210> SEQ ID NO 6
<211> LENGTH: 107
<212> TYPE: PRT
<213> ORGANISM: Homo sapiens

<400> SEQUENCE: 6

-continued

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Ile Lys Tyr
            20                  25                  30

Leu Asn Trp Tyr Gln Gln Lys Pro Gly Lys Ala Pro Lys Leu Leu Ile
        35                  40                  45

Tyr Glu Ala Ser Asn Leu Gln Ala Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Gln Ser Leu Pro Tyr
                85                  90                  95

Thr Phe Gly Gln Gly Thr Lys Val Glu Ile Lys
            100                 105

<210> SEQ ID NO 7
<211> LENGTH: 126
<212> TYPE: PRT
<213> ORGANISM: Homo sapiens

<400> SEQUENCE: 7

Glu Val Gln Leu Val Glu Ser Gly Gly Gly Val Val Gln Pro Gly Arg
1               5                   10                  15

Ser Leu Arg Leu Ser Cys Ser Ser Gly Phe Ile Phe Ser Ser Tyr
            20                  25                  30

Ala Met Tyr Trp Val Arg Gln Ala Pro Gly Lys Gly Leu Glu Trp Val
        35                  40                  45

Ala Ile Ile Trp Asp Asp Gly Ser Asp Gln His Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg Asp Gly Gly His Gly Phe Cys Ser Ser Ala Ser Cys Phe Gly
            100                 105                 110

Pro Asp Tyr Trp Gly Gln Gly Thr Pro Val Thr Val Ser Ser
        115                 120                 125

<210> SEQ ID NO 8
<211> LENGTH: 119
<212> TYPE: PRT
<213> ORGANISM: Homo sapiens

<400> SEQUENCE: 8

Gln Val Gln Leu Gln Glu Ser Gly Pro Gly Leu Val Arg Pro Ser Gln
1               5                   10                  15

Thr Leu Ser Leu Thr Cys Thr Ala Ser Gly Phe Asp Phe Thr Thr Tyr
            20                  25                  30

Trp Met Ser Trp Val Arg Gln Pro Pro Gly Arg Gly Leu Glu Trp Ile
        35                  40                  45

Gly Glu Ile His Pro Asp Ser Ser Thr Ile Asn Tyr Ala Pro Ser Leu
    50                  55                  60

Lys Asp Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Ser Leu Tyr Phe Gly Phe Pro Trp Phe Ala Tyr Trp Gly Gln Gly

```
                    100                 105                 110

Thr Thr Val Thr Val Ser Ser
        115

<210> SEQ ID NO 9
<211> LENGTH: 119
<212> TYPE: PRT
<213> ORGANISM: Homo sapiens

<400> SEQUENCE: 9

Gln Val Gln Leu Gln Glu Ser Gly Pro Gly Leu Val Arg Pro Ser Gln
 1               5                  10                  15

Thr Leu Ser Leu Thr Cys Thr Ala Ser Gly Phe Asp Phe Thr Thr Tyr
            20                  25                  30

Trp Met Ser Trp Val Arg Gln Pro Pro Gly Arg Gly Leu Glu Trp Ile
        35                  40                  45

Gly Glu Ile His Pro Asp Ser Ser Thr Ile Asn Tyr Ala Pro Ser Leu
    50                  55                  60

Lys Asp Arg Val Thr Met Leu Arg Asp Thr Ser Lys Asn Thr Leu Tyr
65                  70                  75                  80

Leu Arg Leu Ser Ser Val Thr Ala Ala Asp Thr Ala Val Tyr Tyr Cys
                85                  90                  95

Ala Ser Leu Tyr Phe Gly Phe Pro Trp Phe Ala Tyr Trp Gly Gln Gly
            100                 105                 110

Thr Thr Val Thr Val Ser Ser
        115

<210> SEQ ID NO 10
<211> LENGTH: 119
<212> TYPE: PRT
<213> ORGANISM: Homo sapiens

<400> SEQUENCE: 10

Gln Val Gln Leu Gln Glu Ser Gly Pro Gly Leu Val Arg Pro Ser Gln
 1               5                  10                  15

Thr Leu Ser Leu Thr Cys Thr Ala Ser Gly Phe Asp Phe Thr Thr Tyr
            20                  25                  30

Trp Met Ser Trp Val Arg Gln Pro Pro Gly Arg Gly Leu Glu Trp Ile
        35                  40                  45

Gly Glu Ile His Pro Asp Ser Ser Thr Ile Asn Tyr Ala Pro Ser Leu
    50                  55                  60

Lys Asp Arg Val Thr Met Leu Arg Asp Thr Ser Lys Asn Gln Phe Ser
65                  70                  75                  80

Leu Arg Leu Ser Lys Val Arg Ser Glu Asp Thr Ala Val Tyr Tyr Cys
                85                  90                  95

Ala Ser Leu Tyr Phe Gly Phe Pro Trp Phe Ala Tyr Trp Gly Gln Gly
            100                 105                 110

Thr Thr Val Thr Val Ser Ser
        115

<210> SEQ ID NO 11
<211> LENGTH: 119
<212> TYPE: PRT
<213> ORGANISM: Homo sapiens

<400> SEQUENCE: 11

Gln Val Gln Leu Gln Glu Ser Gly Pro Gly Leu Val Arg Pro Ser Gln
 1               5                  10                  15
```

```
Thr Leu Ser Leu Thr Cys Thr Ala Ser Gly Phe Asp Phe Thr Thr Tyr
            20                  25                  30

Trp Met Ser Trp Val Arg Gln Pro Gly Arg Gly Leu Glu Trp Ile
        35                  40                  45

Gly Glu Ile His Pro Asp Ser Ser Thr Ile Asn Tyr Ala Pro Ser Leu
    50                  55                  60

Lys Asp Lys Phe Ile Val Ser Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                85                  90                  95

Ala Ser Leu Tyr Phe Gly Phe Pro Trp Phe Ala Tyr Trp Gly Gln Gly
            100                 105                 110

Thr Thr Val Thr Val Ser Ser
            115
```

<210> SEQ ID NO 12
<211> LENGTH: 119
<212> TYPE: PRT
<213> ORGANISM: Homo sapiens

<400> SEQUENCE: 12

```
Glu Val Gln Leu Val Glu Ser Gly Gly Gly Val Val Gln Pro Gly Arg
 1               5                  10                  15

Ser Leu Arg Leu Ser Cys Ser Ser Gly Phe Asp Phe Thr Thr Tyr
            20                  25                  30

Trp Met Ser Trp Val Arg Gln Ala Pro Gly Lys Gly Leu Glu Trp Val
        35                  40                  45

Ala Glu Ile His Pro Asp Ser Ser Thr Ile Asn Tyr Ala Pro Ser Leu
    50                  55                  60

Lys Asp Arg Phe Thr Ile Ser Arg Asp Asn Ser Lys Asn Thr Leu Phe
 65                  70                  75                  80

Leu Gln Met Asp Ser Leu Arg Pro Glu Asp Thr Gly Val Tyr Phe Cys
                85                  90                  95

Ala Ser Leu Tyr Phe Gly Phe Pro Trp Phe Ala Tyr Trp Gly Gln Gly
            100                 105                 110

Thr Pro Val Thr Val Ser Ser
            115
```

<210> SEQ ID NO 13
<211> LENGTH: 119
<212> TYPE: PRT
<213> ORGANISM: Homo sapiens

<400> SEQUENCE: 13

```
Glu Val Gln Leu Val Glu Ser Gly Gly Gly Val Val Gln Pro Gly Arg
 1               5                  10                  15

Ser Leu Arg Leu Ser Cys Ser Ala Ser Gly Phe Asp Phe Thr Thr Tyr
            20                  25                  30

Trp Met Ser Trp Val Arg Gln Ala Pro Gly Lys Gly Leu Glu Trp Ile
        35                  40                  45

Gly Glu Ile His Pro Asp Ser Ser Thr Ile Asn Tyr Ala Pro Ser Leu
    50                  55                  60

Lys Asp Arg Phe Thr Ile Ser Arg Asp Asn Ser Lys Asn Thr Leu Phe
 65                  70                  75                  80

Leu Gln Met Asp Ser Leu Arg Pro Glu Asp Thr Gly Val Tyr Phe Cys
                85                  90                  95

Ala Ser Leu Tyr Phe Gly Phe Pro Trp Phe Ala Tyr Trp Gly Gln Gly
```

Thr Pro Val Thr Val Ser Ser
        115

<210> SEQ ID NO 14
<211> LENGTH: 119
<212> TYPE: PRT
<213> ORGANISM: Homo sapiens

<400> SEQUENCE: 14

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Asp Phe Thr Thr Tyr
            20                  25                  30

Trp Met Ser Trp Val Arg Gln Ala Pro Gly Lys Gly Leu Glu Trp Ile
        35                  40                  45

Gly Glu Ile His Pro Asp Ser Ser Thr Ile Asn Tyr Ala Pro Ser Leu
    50                  55                  60

Lys Asp Arg Phe Thr Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Ser Leu Tyr Phe Gly Phe Pro Trp Phe Ala Tyr Trp Gly Gln Gly
            100                 105                 110

Thr Pro Val Thr Val Ser Ser
        115

<210> SEQ ID NO 15
<211> LENGTH: 119
<212> TYPE: PRT
<213> ORGANISM: Homo sapiens

<400> SEQUENCE: 15

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Asp Phe Thr Thr Tyr
            20                  25                  30

Trp Met Ser Trp Val Arg Gln Ala Pro Gly Lys Gly Leu Glu Trp Ile
        35                  40                  45

Gly Glu Ile His Pro Asp Ser Ser Thr Ile Asn Tyr Ala Pro Ser Leu
    50                  55                  60

Lys Asp Arg Phe Thr Ile Ser Arg Asp Asn Ala Lys Asn Thr Leu Tyr
65                  70                  75                  80

Leu Gln Met Asp Ser Leu Arg Pro Glu Asp Thr Gly Val Tyr Phe Cys
                85                  90                  95

Ala Ser Leu Tyr Phe Gly Phe Pro Trp Phe Ala Tyr Trp Gly Gln Gly
            100                 105                 110

Thr Pro Val Thr Val Ser Ser
        115

<210> SEQ ID NO 16
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 16

```
gag gtc caa ctg gtg gag agc ggt gga ggt gtt gtg caa cct ggc cgg      48
Glu Val Gln Leu Val Glu Ser Gly Gly Gly Val Val Gln Pro Gly Arg
 1               5                  10                  15 tcc ctg cgc ctg tcc tgc tcc gca tct ggc ttc gat ttc acc aca tat      96
Ser Leu Arg Leu Ser Cys Ser Ala Ser Gly Phe Asp Phe Thr Thr Tyr
             20                  25                  30 tgg atg agt tgg gtg aga cag gca cct gga aaa ggt ctt gag tgg att     144
Trp Met Ser Trp Val Arg Gln Ala Pro Gly Lys Gly Leu Glu Trp Ile
         35                  40                  45 gga gaa att cat cca gat agc agt acg att aac tat gcg ccg tct cta     192
Gly Glu Ile His Pro Asp Ser Ser Thr Ile Asn Tyr Ala Pro Ser Leu
     50                  55                  60 aag gat aga ttt aca ata tcg cga gac aac gcc aag aac aca ttg ttc     240
Lys Asp Arg Phe Thr Ile Ser Arg Asp Asn Ala Lys Asn Thr Leu Phe
 65                  70                  75                  80 ctg caa atg gac agc ctg aga ccc gaa gac acc ggg gtc tat ttt tgt     288
Leu Gln Met Asp Ser Leu Arg Pro Glu Asp Thr Gly Val Tyr Phe Cys
                 85                  90                  95 gca agc ctt tac ttc ggc ttc ccc tgg ttt gct tat tgg ggc caa ggg     336
Ala Ser Leu Tyr Phe Gly Phe Pro Trp Phe Ala Tyr Trp Gly Gln Gly
            100                 105                 110 acc ccg gtc acc gtc tcc tca                                         357
Thr Pro Val Thr Val Ser Ser
        115

<210> SEQ ID NO 17
<211> LENGTH: 119
<212> TYPE: PRT
<213> ORGANISM: Homo sapiens

<400> SEQUENCE: 17

Glu Val Gln Leu Val Glu Ser Gly Gly Gly Val Val Gln Pro Gly Arg
 1               5                  10                  15

Ser Leu Arg Leu Ser Cys Ser Ala Ser Gly Phe Asp Phe Thr Thr Tyr
             20                  25                  30

Trp Met Ser Trp Val Arg Gln Ala Pro Gly Lys Gly Leu Glu Trp Ile
         35                  40                  45

Gly Glu Ile His Pro Asp Ser Ser Thr Ile Asn Tyr Ala Pro Ser Leu
     50                  55                  60

Lys Asp Arg Phe Thr Ile Ser Arg Asp Asn Ala Lys Asn Thr Leu Phe
 65                  70                  75                  80

Leu Gln Met Asp Ser Leu Arg Pro Glu Asp Thr Gly Val Tyr Phe Cys
                 85                  90                  95

Ala Ser Leu Tyr Phe Gly Phe Pro Trp Phe Ala Tyr Trp Gly Gln Gly
            100                 105                 110

Thr Pro Val Thr Val Ser Ser
        115

<210> SEQ ID NO 18
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 18 gac atc cag ctg acc cag agc cca agc agc ctg agc gcc agc gtg ggt      48
Asp Ile Gln Leu Thr Gln Ser Pro Ser Ser Leu Ser Ala Ser Val Gly
 1               5                  10                  15 gac aga gtg acc atc acc tgt aag gcc agt cag gat gtg ggt act tct      96
Asp Arg Val Thr Ile Thr Cys Lys Ala Ser Gln Asp Val Gly Thr Ser
```

```
Asp Arg Val Thr Ile Thr Cys Lys Ala Ser Gln Asp Val Gly Thr Ser
            20                  25                  30 gta gct tgg tac cag cag aag cca ggt aag gct cca aag ctg ctg atc       144
Val Ala Trp Tyr Gln Gln Lys Pro Gly Lys Ala Pro Lys Leu Leu Ile
         35                  40                  45 tac tgg aca tcc acc cgg cac act ggt gtg cca agc aga ttc agc ggt       192
Tyr Trp Thr Ser Thr Arg His Thr Gly Val Pro Ser Arg Phe Ser Gly
     50                  55                  60 agc ggt agc ggt acc gac ttc acc ttc acc atc agc agc ctc cag cca       240
Ser Gly Ser Gly Thr Asp Phe Thr Phe Thr Ile Ser Ser Leu Gln Pro
 65              70                  75                  80 gag gac atc gcc acc tac tac tgc cag caa tat agc ctc tat cgg tcg       288
Glu Asp Ile Ala Thr Tyr Tyr Cys Gln Gln Tyr Ser Leu Tyr Arg Ser
                 85                  90                  95 ttc ggc caa ggg acc aag gtg gaa atc aaa                               318
Phe Gly Gln Gly Thr Lys Val Glu Ile Lys
             100                 105

<210> SEQ ID NO 19
<211> LENGTH: 106
<212> TYPE: PRT
<213> ORGANISM: Homo sapiens

<400> SEQUENCE: 19

Asp Ile Gln Leu Thr Gln Ser Pro Ser Ser Leu Ser Ala Ser Val Gly
 1               5                  10                  15

Asp Arg Val Thr Ile Thr Cys Lys Ala Ser Gln Asp Val Gly Thr Ser
            20                  25                  30

Val Ala Trp Tyr Gln Gln Lys Pro Gly Lys Ala Pro Lys Leu Leu Ile
         35                  40                  45

Tyr Trp Thr Ser Thr Arg His Thr Gly Val Pro Ser Arg Phe Ser Gly
     50                  55                  60

Ser Gly Ser Gly Thr Asp Phe Thr Phe Thr Ile Ser Ser Leu Gln Pro
 65              70                  75                  80

Glu Asp Ile Ala Thr Tyr Tyr Cys Gln Gln Tyr Ser Leu Tyr Arg Ser
                 85                  90                  95

Phe Gly Gln Gly Thr Lys Val Glu Ile Lys
             100                 105

<210> SEQ ID NO 20
<211> LENGTH: 11
<212> TYPE: PRT
<213> ORGANISM: Mus sp.

<400> SEQUENCE: 20

Lys Ala Ser Gln Asp Val Gly Thr Ser Val Ala
 1               5                  10

<210> SEQ ID NO 21
<211> LENGTH: 7
<212> TYPE: PRT
<213> ORGANISM: Mus sp.

<400> SEQUENCE: 21

Trp Thr Ser Thr Arg His Thr
 1               5

<210> SEQ ID NO 22
<211> LENGTH: 8
<212> TYPE: PRT
<213> ORGANISM: Mus sp.
```

-continued

```
<400> SEQUENCE: 22

Gln Gln Tyr Ser Leu Tyr Arg Ser
  1               5

<210> SEQ ID NO 23
<211> LENGTH: 5
<212> TYPE: PRT
<213> ORGANISM: Mus sp.

<400> SEQUENCE: 23

Thr Tyr Trp Met Ser
  1               5

<210> SEQ ID NO 24
<211> LENGTH: 17
<212> TYPE: PRT
<213> ORGANISM: Mus sp.

<400> SEQUENCE: 24

Glu Ile His Pro Asp Ser Ser Thr Ile Asn Tyr Ala Pro Ser Leu Lys
  1               5                  10                  15

Asp

<210> SEQ ID NO 25
<211> LENGTH: 10
<212> TYPE: PRT
<213> ORGANISM: Mus sp.

<400> SEQUENCE: 25

Leu Tyr Phe Gly Phe Pro Trp Phe Ala Tyr
  1               5                  10

<210> SEQ ID NO 26
<211> LENGTH: 119
<212> TYPE: PRT
<213> ORGANISM: Homo sapiens

<400> SEQUENCE: 26

Gln Val Gln Leu Gln Glu Ser Gly Pro Gly Leu Val Arg Pro Ser Gln
  1               5                  10                  15

Thr Leu Ser Leu Thr Cys Thr Val Ser Gly Ser Thr Phe Ser Thr Tyr
                 20                  25                  30

Trp Met Ser Trp Val Arg Gln Pro Pro Gly Arg Gly Leu Glu Trp Ile
             35                  40                  45

Gly Glu Ile His Pro Asp Ser Ser Thr Ile Asn Tyr Ala Pro Ser Leu
         50                  55                  60

Lys Asp Arg Val Thr Met Leu Val Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Leu Tyr Phe Gly Phe Pro Trp Phe Ala Tyr Trp Gly Gln Gly
                100                 105                 110

Thr Thr Val Thr Val Ser Ser
            115

<210> SEQ ID NO 27
<211> LENGTH: 119
<212> TYPE: PRT
<213> ORGANISM: Homo sapiens

<400> SEQUENCE: 27
```

-continued

```
Glu Val Gln Leu Val Glu Ser Gly Gly Val Val Gln Pro Gly Arg
 1           5                   10                  15

Ser Leu Arg Leu Ser Cys Ser Ser Ser Gly Phe Ile Phe Ser Thr Tyr
            20                  25                  30

Trp Met Ser Trp Val Arg Gln Ala Pro Gly Lys Gly Leu Glu Trp Val
        35                  40                  45

Ala Glu Ile His Pro Asp Ser Ser Thr Ile Asn Tyr Ala Pro Ser Leu
    50                  55                  60

Lys Asp Arg Phe Thr Ile Ser Arg Asp Asn Ser Lys Asn Thr Leu Phe
 65             70                  75                      80

Leu Gln Met Asp Ser Leu Arg Pro Glu Asp Thr Gly Val Tyr Phe Cys
            85                  90                  95

Ala Arg Leu Tyr Phe Gly Phe Pro Trp Phe Ala Tyr Trp Gly Gln Gly
            100                 105                 110

Thr Pro Val Thr Val Ser Ser
            115
```